United States Patent
Taber et al.

(10) Patent No.: US 9,636,155 B2
(45) Date of Patent: May 2, 2017

(54) METHOD AND APPARATUS FOR AN INTRAMUDULLARY IMPLANT AND METHOD OF IMPLANTATION THEREOF

(71) Applicant: BioMedical Enterprises, Inc., San Antonio, TX (US)

(72) Inventors: Joseph H. Taber, San Antonio, TX (US); Daniel F. Cheney, San Antonio, TX (US); Joe Ritz, San Antonio, TX (US); Don Peterson, San Antonio, TX (US); Bernard Humes, San Antonio, TX (US)

(73) Assignee: BioMedical Enterprises, Inc., San Antonio, TX (US)

( * ) Notice: Subject to any disclaimer, the term of this patent is extended or adjusted under 35 U.S.C. 154(b) by 29 days.

(21) Appl. No.: 14/804,826

(22) Filed: Jul. 21, 2015

(65) Prior Publication Data

US 2015/0320460 A1    Nov. 12, 2015

Related U.S. Application Data

(63) Continuation-in-part of application No. 14/487,315, filed on Sep. 16, 2014.
(Continued)

(51) Int. Cl.
*A61B 17/72* (2006.01)
*A61B 17/88* (2006.01)
(Continued)

(52) U.S. Cl.
CPC ...... *A61B 17/7266* (2013.01); *A61B 17/7291* (2013.01); *A61B 17/8872* (2013.01);
(Continued)

(58) Field of Classification Search
CPC ............ A61B 17/7266; A61B 17/7291; A61B 17/7258; A61B 17/7233; A61B 17/7283;
(Continued)

(56) References Cited

U.S. PATENT DOCUMENTS 5,120,175 A    6/1992  Arbegast et al.
5,171,252 A    12/1992 Friedland
(Continued)

FOREIGN PATENT DOCUMENTS

CN    87101011 A    2/1988
EP    0326426 B1    12/1994
(Continued)

OTHER PUBLICATIONS

Prandi, Bernard, Development of a New Nitinol Implant for Hand Surgery, Proceedings of the International Conference of Shape Memory and Superelastic Technologies, Oct. 3-7, 2004, Kurhaus BadeBaden, Baden-Baden, Germany.
(Continued)

*Primary Examiner* — Julianna N Harvey
(74) *Attorney, Agent, or Firm* — Christopher L. Makay

(57) ABSTRACT

A method of loading an implant inserter with an implant tab and an intramedullary orthopedic implant includes placing the intramedullary orthopedic implant engaged with the implant tab in an implant tab press tool. The implant tab press tool closes the implant tab, which is then moved to a locked position. The implant press tool opens, and the implant tab coupled with the intramedullary orthopedic implant is removed therefrom. The implant tab coupled with the intramedullary orthopedic implant and the implant inserter are placed in an inserter press tool. The inserter press tool closes the implant inserter, which is then moved to a locked position. The inserter press tool opens, and the implant inserter loaded with the implant tab and the
(Continued)

intramedullary orthopedic implant coupled therewith is removed from the inserter press tool.

21 Claims, 64 Drawing Sheets

Related U.S. Application Data

(60) Provisional application No. 61/998,037, filed on Jun. 16, 2014, provisional application No. 61/962,914, filed on Nov. 18, 2013.

(51) Int. Cl.
*A61B 50/30* (2016.01)
*A61B 50/33* (2016.01)
*A61B 17/56* (2006.01)
*A61B 90/00* (2016.01)

(52) U.S. Cl.
CPC .............. *A61B 50/30* (2016.02); *A61B 50/33* (2016.02); *A61B 2017/564* (2013.01); *A61B 2050/3008* (2016.02); *A61B 2090/033* (2016.02); *A61B 2090/034* (2016.02); *A61B 2090/062* (2016.02)

(58) Field of Classification Search
CPC .... A61B 17/72; A61B 17/8872; A61B 17/564
See application file for complete search history.

(56) References Cited

U.S. PATENT DOCUMENTS

| | | | |
|---|---|---|---|
| 5,179,915 A | 1/1993 | Cohen et al. |
| 5,281,225 A | 1/1994 | Vicenzi |
| 5,358,405 A | 10/1994 | Imai |
| 5,474,557 A | 12/1995 | Mai |
| 5,882,351 A | 3/1999 | Fox |
| 6,203,545 B1 | 3/2001 | Stoffella |
| 6,281,262 B1 | 8/2001 | Shikinami |
| 6,290,719 B1 | 9/2001 | Garberoglio |
| 6,332,885 B1 | 12/2001 | Martella |
| 6,592,370 B2 | 7/2003 | Morgan |
| 6,626,910 B1 | 9/2003 | Hugues |
| 7,052,498 B2 | 5/2006 | Levy et al. |
| 7,918,879 B2 | 4/2011 | Yeung et al. |
| 8,162,942 B2 | 4/2012 | Coati et al. |
| 8,262,712 B2 | 9/2012 | Coilard-Lavirotte et al. |
| 8,394,097 B2 | 3/2013 | Peyrot et al. |
| 8,475,456 B2 | 7/2013 | Augoyard et al. |
| 8,834,483 B2 | 9/2014 | Cheney et al. |
| 2002/0165544 A1 | 11/2002 | Perren et al. |
| 2004/0230193 A1 | 11/2004 | Cheung et al. |
| 2005/0010228 A1 | 1/2005 | Medoff |
| 2005/0043757 A1 | 2/2005 | Arad et al. |
| 2005/0055027 A1 | 3/2005 | Yeung et al. |
| 2005/0283159 A1 | 12/2005 | Amara |
| 2012/0083791 A1* | 4/2012 | Cheney .............. A61B 17/8872 606/99 |
| 2015/0073413 A1 | 3/2015 | Palmer et al. |

FOREIGN PATENT DOCUMENTS

| | | |
|---|---|---|
| EP | 0821923 A1 | 2/1998 |
| EP | 0896813 A3 | 8/1999 |
| EP | 1079752 B1 | 1/2005 |
| EP | 1582164 A1 | 10/2005 |
| FR | 2787313 A1 | 12/1998 |
| JP | 1057398 A | 3/1998 |

OTHER PUBLICATIONS

A.W Anson, D.H.R. Jenkins, and S. Andrews, Development of a Nickel Titanium Shape Memory Alloy Bone Repair Staple and Other In-Vivo Orthopaedic and Cardio-Vascular Devices, Proceedings of tthe Technology Transfer Workshop, held at ESA/ESTEC, Noordwijk, The Netherlands, May 25-27, 1994 (ESA SP-364, Aug. 1994).

ARIM Soft Tissue Reattachment Anchor Brochure, MemoMetal, Inc., Oct. 26, 2008.

Smart Toe Orthopedic Implant Brochure, MemoMetal, Inc., Oct. 26, 2008.

X-Fuse Orthopedic Implant Brochure, MemoMetal, Inc., Oct. 26, 2008.

\* cited by examiner

METHOD AND APPARATUS FOR AN INTRAMUDULLARY IMPLANT AND METHOD OF IMPLANTATION THEREOF

BACKGROUND OF THE INVENTION

1. Field of the Invention

The present invention relate generally to an intramedullary implant for use in one or more bones to provide internal fixation during surgery, instrumentation for using the intramedullary implant, packaging for the intramedullary implant and the instrumentation, and also a method of implanting the intramedullary implant.

2. Description of the Related Art

Corrective surgery involving bones can include the use of external fixation devices or internal fixation devices. Internal fixation devices can be located inside the bone or outside the bone. Implants located inside bones can be referred to as intramedullary implants. Intramedullary implants can be made of metal, shape memory materials, artificial bone, or bioresorbable materials. Intramedullary implants that use shape memory materials are typically composed of shape memory materials such as Nitinol.

Intramedullary implants that are composed of Nitinol typically operate using a temperature dependent property of Nitinol called shape memory. Shape memory allows the intramedullary implants the ability to undergo deformation at one temperature and then recover their original, undeformed shape upon heating above their "transformation temperature". In practice this is frequently accomplished by using preoperative freezing to deform the intramedullary implants from a first final shape into a second shape. After insertion the intramedullary implants recover their undeformed shape due to heating by the body above their transformation temperature. However, preoperative freezing can be a logistical challenge both to health care facilities as well as a surgeon, who has a limited amount of time to work with the implant before it warms to room temperature.

Intramedullary implants can also be designed to utilize the superelastic properties of a material such as Nitinol. In this instance, the implant deforms during implantation, but uses superelastic behavior to flex and engage the bone. A difficulty in designing a superelastic intramedullary implant is allowing the surgeon access to both sides of the implant. While it is simple to insert one side of the implant into a first bone, it becomes difficult to insert the second side into a second bone.

In designing a proper intramedullary implant that affixes one or more bones, it is also difficult to achieve proper position within the bones. In particular, when the intramedullary implant is inserted into one or more bones, one of the bones is typically less resistive to motion than the other bone due to different anatomy or bone quality. As such, when the bones are reduced or pressed together, the intramedullary implant tends to migrate in the direction of the bone that is less resistive, thereby resulting in an improper final placement of the intramedullary implant. Furthermore, once the implant is positioned inside the bone, and the bones are fully reduced so that they are touching, it is difficult to reposition the implant because there is no access to the intramedullary space.

Accordingly, an intramedullary implant design that does not require preoperative freezing and maintains the intramedullary implant in the proper position within the bones would be beneficial.

SUMMARY OF THE INVENTION

In accordance with the present invention, an intramedullary orthopedic implant includes at least a first body section having a first end and a second end. The first body section further includes first and second wings extending away from the first end of the first body section towards the second end of the first body section. The intramedullary orthopedic implant may include a second body section having a first end located at the second end of the first body section and a second end. The second body section includes first and second wings extending away from the first end of the second body section towards the second end. The intramedullary orthopedic implant further includes first and second legs located at the second end of either the first body section or the second body section. The first and second wings of the first body section may lie in a first plane and the first and second wings of the second body section may lie in a second plane.

The first and second wings of the first body section begin in a first open insertion shape and during insertion into an intramedullary canal in a first bone flex towards the first body section to conform with the shape of the intramedullary canal. The first and second wings of the first body section accordingly move to a second implanted shape that creates an anchoring force between the first and second wings and the first bone, thereby anchoring the first and second wings within the intramedullary canal in the first bone. Likewise, the first and second wings of the second body section begin in a first open insertion shape and during insertion into the intramedullary canal in a first bone flex towards the second body section to conform with the shape of the intramedullary canal. The first and second wings of the second body section accordingly move to a second implanted shape that creates an anchoring force between the first and second wings and the first bone, thereby anchoring the first and second wings within the intramedullary canal in the first bone.

The first and second legs begin in a first implanted shape, are movable to a second insertion shape, and remain in the second insertion shape as long as the first and second legs are mechanically constrained. The first and second legs each include a bend with a transition section extending from the second end of either the first body section or the second body section, a bow adjacent the bend, and a tip adjacent the bow, wherein mechanically constraining the first and second legs results in the transition sections moving in are toward one another until the tips are adjacent. After insertion of the first and second legs into an intramedullary canal in a second bone and the removal of the mechanical constraint, the first and second legs move from the second insertion shape to the first implanted shape. The movement of the first and second legs from the second insertion shape to the first implanted shape creates an anchoring force between the first and second legs and the second bone, thereby anchoring the first and second legs within the intramedullary canal in the second bone.

When implanting the intramedullary orthopedic implant, the first body section inserts head first into the intramedullary canal in the first bone until the first body section, the second body section, and the transition sections reside within the intramedullary canal in the first bone. After insertion of the first and second legs into the intramedullary canal in the second bone and the removal of the mechanical constraint, the transition sections move in are away from one another such that the first and second legs return to their first implanted shape. The return of the first and second legs to their first implanted shape creates an anchoring force between the first and second legs and the second bone, thereby anchoring the first and second legs within the intramedullary canal in the second bone. The anchoring forces of the first and second wings of the first and second body sections oppose the anchoring force of the first and second legs, thereby compressing the first bone with the second bone.

The intramedullary orthopedic implant may be implanted using an implant tab and an implant inserter. The implant tab engages and constrains the first and second legs in the second insertion shape. The implant inserter engages the first and second legs in the second insertion shape and is used to insert the first and second body sections into the intramedullary canal in the first bone. After insertion of the first and second body sections into the intramedullary canal in the first bone and the disengagement of the implant inserter from the first and second legs, the implant tab is grasped to maintain the first and second body sections in the intramedullary canal in the first bone and further to allow the insertion of the first and second legs in the second insertion shape into the intramedullary canal in the second bone. The disengagement of the implant tab from the first and second legs releases the first and second legs to move from the second insertion shape to the first implanted shape. The movement of the first and second legs to move from the second insertion shape to the first implanted shape creates an anchoring force between the first and second legs and the second bone, thereby anchoring the first and second legs within the intramedullary canal in the second bone.

The implant inserter and implant tab loaded with the intramedullary orthopedic implant may be sterilely packaged. An intramedullary implant package receives therein the implant inserter and implant tab loaded with the intramedullary orthopedic implant. After packaging of the implant inserter and implant tab loaded with the intramedullary orthopedic implant, the implant package is sealed and the implant inserter and implant tab loaded with the intramedullary orthopedic implant sterilized. The implant package maintains the implant inserter and implant tab loaded with the intramedullary orthopedic implant sterile after sterilization.

The intramedullary orthopedic implant may be utilized to fixate a first bone and a second bone. Intramedullary canals are prepared in the first bone and the second bone. The first body section inserts into the intramedullary canal in the first bone, resulting in the wings flexing towards the first body section to conform with the shape of the intramedullary canal in the first bone. The flexing of the wings of the first body section creates an anchoring force between the wings and the first bone, thereby anchoring the wings within the intramedullary canal in the first bone. The first and second legs insert into the intramedullary canal in the second bone. The mechanical constraint is removed such that the first and second legs move from the second insertion shape to the first implanted shape. The movement of the first and second legs from the second insertion shape to the first implanted shape creates an anchoring force between the first and second legs and the second bone, thereby anchoring the first and second legs within the intramedullary canal in the second bone such that the first bone compresses with the second bone.

The implant inserter and implant tab loaded with the intramedullary orthopedic implant are used as follows to fixate a first bone and a second bone. Intramedullary canals are prepared in the first bone and the second bone. The implant inserter is used to insert the first body section into the intramedullary canal in the first bone such that the wings flex towards the body section to conform with the shape of the intramedullary canal in the first bone. The flexing of the wings of the first body section creates an anchoring force between the wings and the first bone, thereby anchoring the wings within the intramedullary canal in the first bone. The implant inserter is disengaged from the first and second legs, and the implant tab grasped to maintain the body section in the intramedullary canal in the first bone. The first and second legs are inserted into the intramedullary canal in the second bone. The implant tab is disengaged from the first and second legs such that the first and second legs move from the second insertion shape to the first implanted shape. The movement of the first and second legs from the second insertion shape to the first implanted shape creates an anchoring force between the first and second legs and the second bone, thereby anchoring the first and second legs within the intramedullary canal in the second such that the first bone compresses with the second bone.

The implant inserter may be loaded with the implant tab and the intramedullary orthopedic implant using a method incorporating mechanical assistance. The implant tab includes first and second tab legs and is movable between an unlocked and a locked position. In moving between the unlocked and the locked position, the first and second tab legs transition between a normally open and a closed position. The implant inserter includes first and second inserter arms that transition between a normally splayed position and an implant engagement position. Furthermore, the implant inserter is movable between an open and a locked position.

The first and second legs of the intramedullary orthopedic implant in their first implanted shape engage the implant tab in its unlocked position. After the intramedullary orthopedic implant engages the implant tab, the intramedullary orthopedic implant and the implant tab are placed in an implant tab press tool. The implant tab press tool is activated to close the implant tab such that the implant tab is moved to its locked position and the first and second tab legs transition to their closed position. Furthermore, moving the implant tab to its locked position couples the intramedullary orthopedic implant with the implant tab such that the first and second legs of the intramedullary orthopedic implant are constrained in their second insertion shape. Once the intramedullary orthopedic implant couples with the implant tab, the implant press tool is deactivated and the implant tab loaded with the intramedullary orthopedic implant is removed from the implant tab press tool.

The implant tab coupled with the intramedullary orthopedic implant is placed in an inserter press tool. The implant inserter having its first and second inserter arms in their normally splayed position is placed in the inserter press tool such that its first and second inserter arms surround a portion of the implant tab and the intramedullary orthopedic implant. The inserter press tool is activated to move the first and second inserter arms to their implant engagement position. In the implant engagement position implant engagement position, a portion of the first and second inserter arms grasps the implant tab and the first and second legs of the intramedullary orthopedic implant. The implant inserter is then moved to its locked position, wherein the implant inserter is loaded with the implant tab and the intramedullary orthopedic implant coupled therewith. The inserter press tool is deactivated and the implant inserter loaded with the implant tab and the intramedullary orthopedic implant coupled therewith is removed from the inserter press tool.

DETAILED DESCRIPTION OF THE PREFERRED EMBODIMENTS

Figure 1:
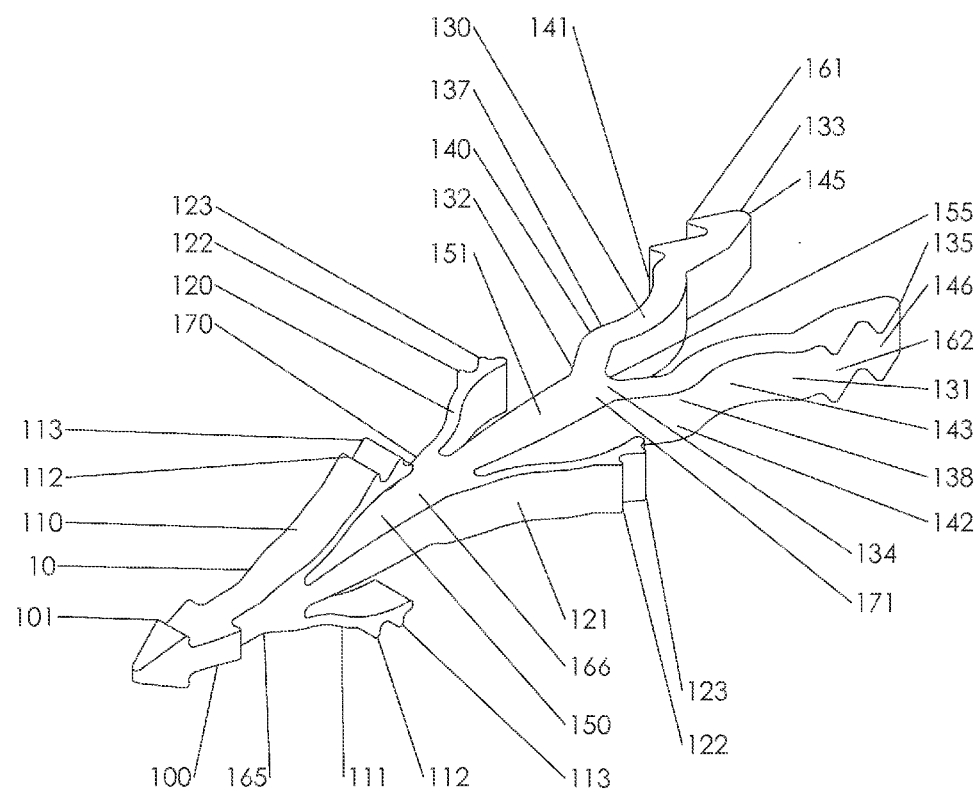
FIG. 1 is a perspective view illustrating an implant including wings in a first open insertion shape and legs in a first implanted shape.
Figure 2:
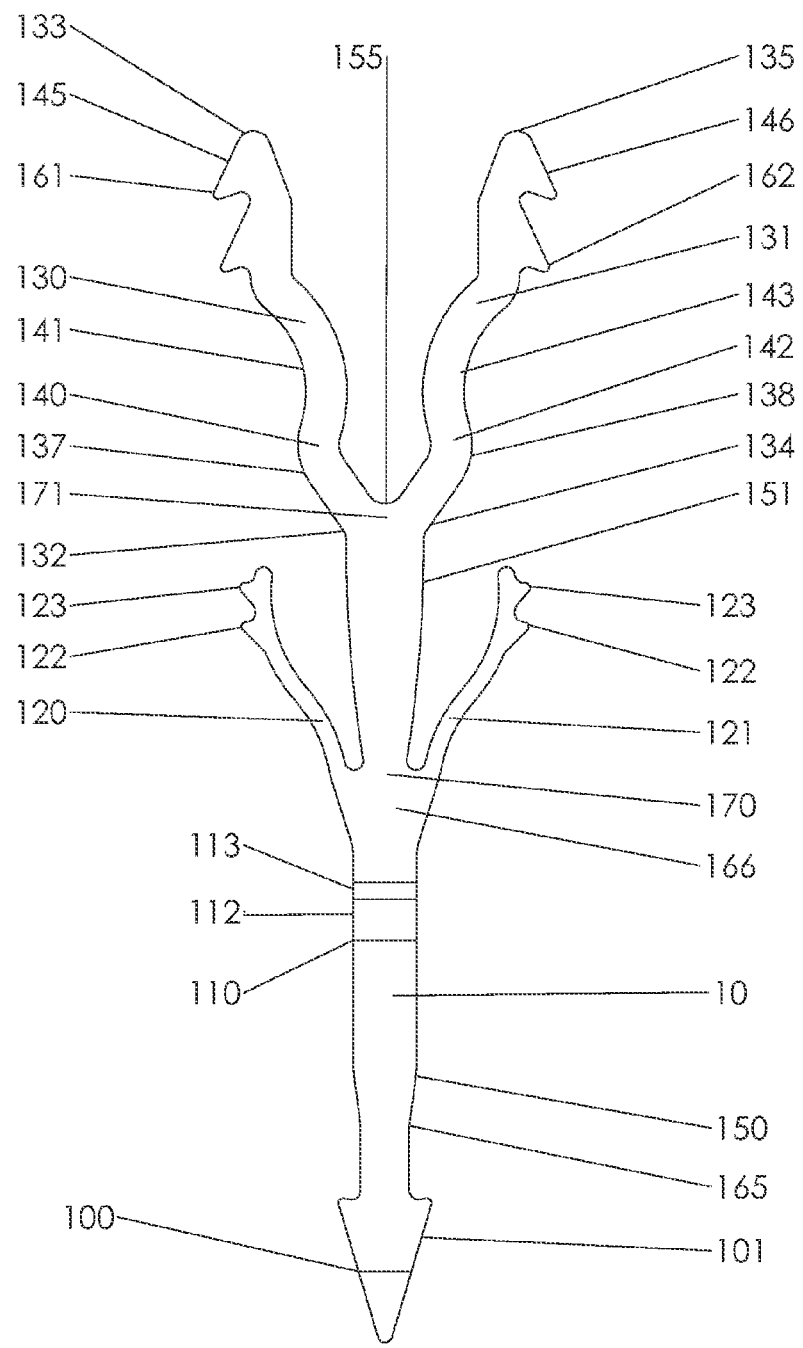
FIG. 2 is a top view illustrating the implant including the wings in the first open insertion shape and the legs in the first implanted shape.
Figure 3:
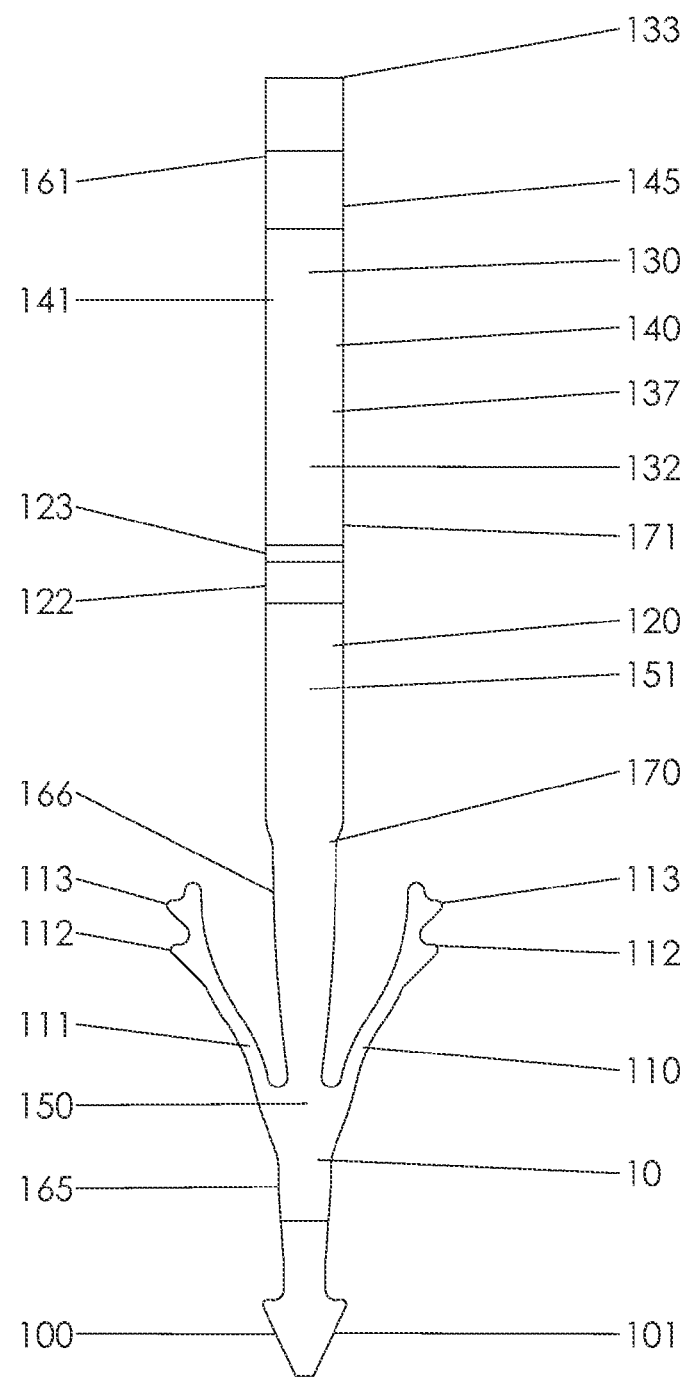
FIG. 3 is a side view illustrating the implant including the wings in the first open insertion shape and the legs in the first implanted shape.
Figure 4:
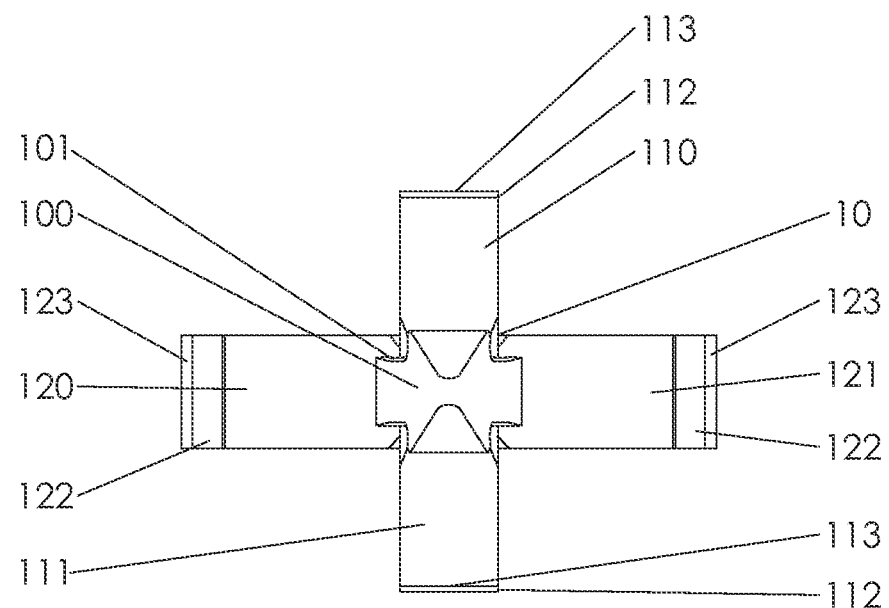
FIG. 4 is a front view illustrating the implant including the wings in the first open insertion shape.
Figure 5:
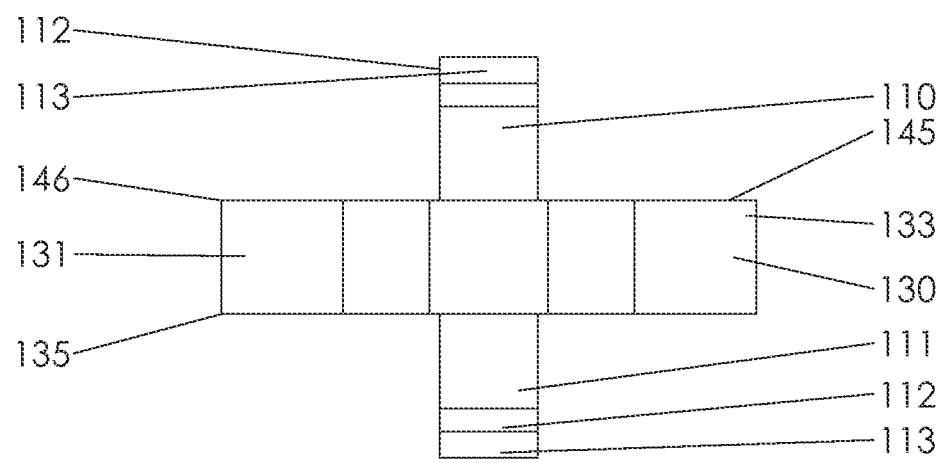
FIG. 5 is a rear view illustrating the implant including the wings in the first open insertion shape and the legs in the first implanted shape.

As required, detailed embodiments of the present invention are disclosed herein; however, it is to be understood that the disclosed embodiments are merely exemplary of the invention, which may be embodied in various forms. Figures are not necessarily to scale, and some features may be exaggerated to show details of particular components or steps.

FIGS. 1-28 illustrate the preferred embodiment of an implant 10 and an implant insertion device 40. The implant 10 includes wings 110, 111, 120, and 121 and legs 130 and 131. The implant insertion device 40 engages the implant 10 to allow a surgeon to insert the implant 10 into tissue or bone during surgery. After insertion, the wings 110, 111, 120, and 121 and legs 130 and 131 allow the implant 10 to fixate the tissue or bone.

The implant 10 is composed of a shape memory material such as Nitinol that allows the wings 110, 111, 120, and 121 of the implant 10 to move between a first open insertion shape and an implanted shape. Likewise, a shape memory material such as Nitinol allows the legs 130 and 131 of the implant 10 to move between a first implanted shape and an insertion shape.

Shape memory materials such as Nitinol include temperature dependent properties and temperature independent properties. Shape memory is a temperature dependent property that allows the shape memory material the ability to undergo deformation at one temperature and then recover its original, undeformed shape upon heating above its "transformation temperature". Superelasticity is a temperature independent property that allows the shape memory material the ability to undergo a mechanical deformation due to an external force applied to the shape memory material, and then recover its original undeformed shape upon release of the external force.

The implant 10 may incorporate either temperature dependent shape memory properties or temperature independent superelastic properties. However, the implant 10 according to the preferred embodiment is superelastic in that the implant 10 stores mechanical energy and is subject to elastic (recoverable) deformation when the stored mechanical energy is released. For example, the application of an external force to the implant 10 through insertion of the implant 10 into an intramedullary canal of a bone results in the mechanical deformation of the wings 110, 111, 120, and 121 from their first open insertion shape to their implanted shape. Furthermore, the application of an external force to the implant 10 through the loading of the implant insertion device 40 with the implant 10 results in the mechanical deformation of the legs 130 and 131 from their first implanted shape to their insertion shape.

The ability of the wings 110, 111, 120, and 121 of the implant 10 to mechanically deform from their first open insertion shape to their implanted shape aids insertion into an intramedullary canal of a first bone. Likewise, the loading of the implant insertion device 40 with the implant 10 resulting in the mechanical deformation of the legs 130 and 131 from their first implanted shape to their insertion shape aids insertion into an intramedullary canal of a second bone.

After insertion, the wings 110, 111, 120, and 121 of the implant 10 in their implanted shape engage the intramedullary canal of the first bone due to the mechanical energy stored therein as a result of their elastic deformation. Furthermore, upon release from the implant insertion device 40, the legs 130 and 131 of the implant 10 release their stored mechanical energy by elastically deforming to their first implanted shape. The stored mechanical energy of the wings 110, 111, 120, and 121 and the released mechanical energy of the legs 130 and 131 secures the implant 10 in the tissue or bone and maintains the tissue or bone fixated together. In maintaining the tissue or bones fixated together, the implant 10 may aid in the healing process in that the implant 10 continuously applies force to the fixated tissue or bone as the wings 110, 111, 120, and 121 transition from their first open insertion shape to their implanted shape and the legs 130 and 131 transition from their insertion shape to their first implanted shape.

In the preferred embodiment of the implant 10, the implant 10 incorporates temperature independent superelastic properties to load the implant insertion device 40 with the implant 10 and to fixate tissue or bone. However, those of ordinary skill in the art will recognize that the implant 10 can incorporate the temperature dependent properties of shape memory as well, without losing any of the implant design advantages. In such an embodiment, the wings 110, 111, 120, and 121 during insertion of the implant 10 will again mechanically deform from their first open insertion shape into their implanted shape upon insertion into an intramedullary canal of a first bone. Likewise, the legs 130 and 131 of the implant 10 can again be mechanically constrained from their first implanted shape into their insertion shape. Upon warming to body temperature, the shape memory property will cause the wings 110, 111, 120, and 121, and legs 130 and 131 to transform to their expanded shape such that they engage bone. In both a superelastic and shape memory embodiment, the implant does not require preoperative freezing and the end result of the implant fixating the two bones is the same.

FIGS. 1-8 illustrate the implant 10. In the preferred embodiment, the implant 10 is an intramedullary implant and includes a body section comprised of a first body section 150 and a second body section 151, legs 130 and 131, and a longitudinal axis 155 that bisects the first body section 150, the second body section 151, and the legs 130 and 131. The design of the implant 10 including the first body section 150, the second body section 151, and the legs 130 and 131 allows the first and second body sections 150 and 151 and a portion of the legs 130 and 131 adjacent the second body section 151 to insert into an intramedullary canal of a first bone. In addition, the design of the implant 10 allows a distal portion of the legs 130 and 131 to insert into an intramedullary canal of a second bone, thereby fixating the first bone and second bone together.

The first body section 150 includes a head 100, wings 110 and 111, a first end 165, and a second end 166. The head 100 extends from the first end 165 of the first body section 150 and includes barbs 101. The head 100 inserts into the intramedullary canal of the first bone, and the barbs 101 anchor the head 100 into the intramedullary canal of the first bone. One of ordinary skill in the art will recognize that the head 100 may include any number of barbs 101 depending on application and the barbs 101 may alternate or protrude coplanar in their orientation.

The wings 110 and 111 include tips 112 and extend outward and away from the first end 165 of the first body section 150 in a direction towards the second end 166 of the first body section 150. The tips 112 are oriented in a direction substantially parallel with the longitudinal axis 155 and include engagement barbs 113. The barbs 113 secure the wings 110 and 111 and therefore the first body section 150 to the intramedullary canal of the first bone.

The second body section 151 includes wings 120 and 121, a first end 170, and a second end 171. The wings 120 and 121 include tips 122 and extend outward and away from the first end 170 of the second body section 151 in a direction towards the second end 171 of the second body section 151. The tips 122 are oriented in a direction substantially parallel with the longitudinal axis 155 and include engagement barbs 123. The barbs 123 secure the wings 120 and 121 and therefore the second body section 151 to the intramedullary canal of the first bone.

The design of the wings 110 and 111 and the wings 120 and 121 of the implant 10 allow easier insertion into the intramedullary canal of the first bone. In particular, the wings 110 and 111 and the wings 120 and 121 are shaped in that they are narrow at the point of insertion and expand outward and away from the point of insertion. In addition, the wings 110 and 111 and the wings 120 and 121 incorporate the superelastic properties of the implant 10 such that the wings 110, 111, 120, and 121 prior to insertion begin in a first open insertion shape and then during insertion move to an implanted shape. The wings 110 and 111 flex towards the first body section 150 and the wings 120 and 121 flex towards the second body section 151 during insertion into the intramedullary canal of the first bone, thereby moving the wings 110, 111, 120, and 121 from their first open insertion shape to their implanted shape and creating an anchoring force between the wings 110, 111, 120, and 121 and the first bone. After insertion into the intramedullary canal of the first bone, the wings 110, 111, 120, and 121 apply the anchoring force against the intramedullary canal such that the wings 110, 111, 120, and 121 secure and anchor the implant 10 within the intramedullary canal of the first bone.

One of ordinary skill in the art will recognize the wings 110 and 111 and the wings 120 and 121 may include any number of barbs 113 and 123 respectively depending on application. In addition, the barbs 113 and 123 of the wings 110 and 111 and the wings 120 and 121 respectively may protrude in a variation of angles and directions depending on application. Furthermore, while the preferred embodiment discloses a first body section 150 with wings 110 and 111 and a second body section 151 with wings 120 and 121, one of ordinary skill in the art will recognize that the implant 10 may include only a single body section and wings.

The leg 130 includes a proximal end 132, a distal end 133, a bend 140 including a transition section 137, a bow 141, and a tip 145 including barbs 161. Likewise, the leg 131 includes a proximal end 134, a distal end 135, a bend 142 including a transition section 138, a bow 143, and a tip 146 including barbs 162. The legs 130 and 131 incorporate the superelastic properties of the implant 10 in that the legs 130 and 131 move from a first implanted shape to an insertion shape when an external force is applied thereto.

In moving to the insertion shape, the transition sections 137 and 138 travel angularly toward the longitudinal axis 155 such that the tips 145 and 146 abut, the bows 141 and 143 are adjacent, and the bends 140 and 142 converge to define an aperture 149 therebetween. The legs 130 and 131 return from their insertion shape to their first implanted shape when the external force is removed. In moving to the first implanted shape, the legs 130 and 131 assume a splayed shape due to the transition sections 137 and 138 traveling angularly away from the longitudinal axis 155 such that the tips 145 and 146 and the bows 141 and 143 separate and the bends 140 and 142 diverge to open the aperture 149.

Figure 6:
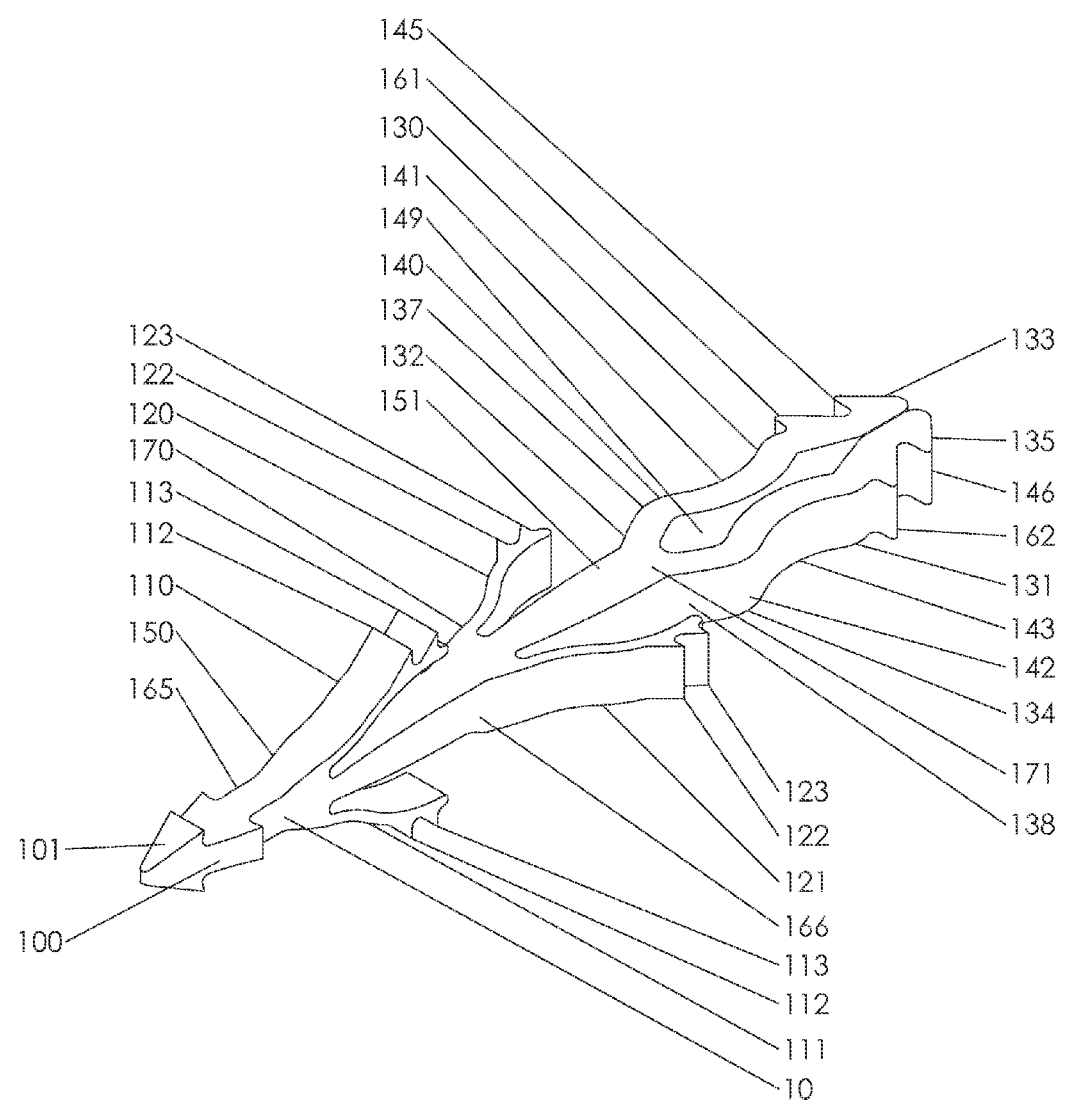
FIG. 6 is a perspective view illustrating the implant including the wings in the first open insertion shape and the legs in an insertion shape.
Figure 7:
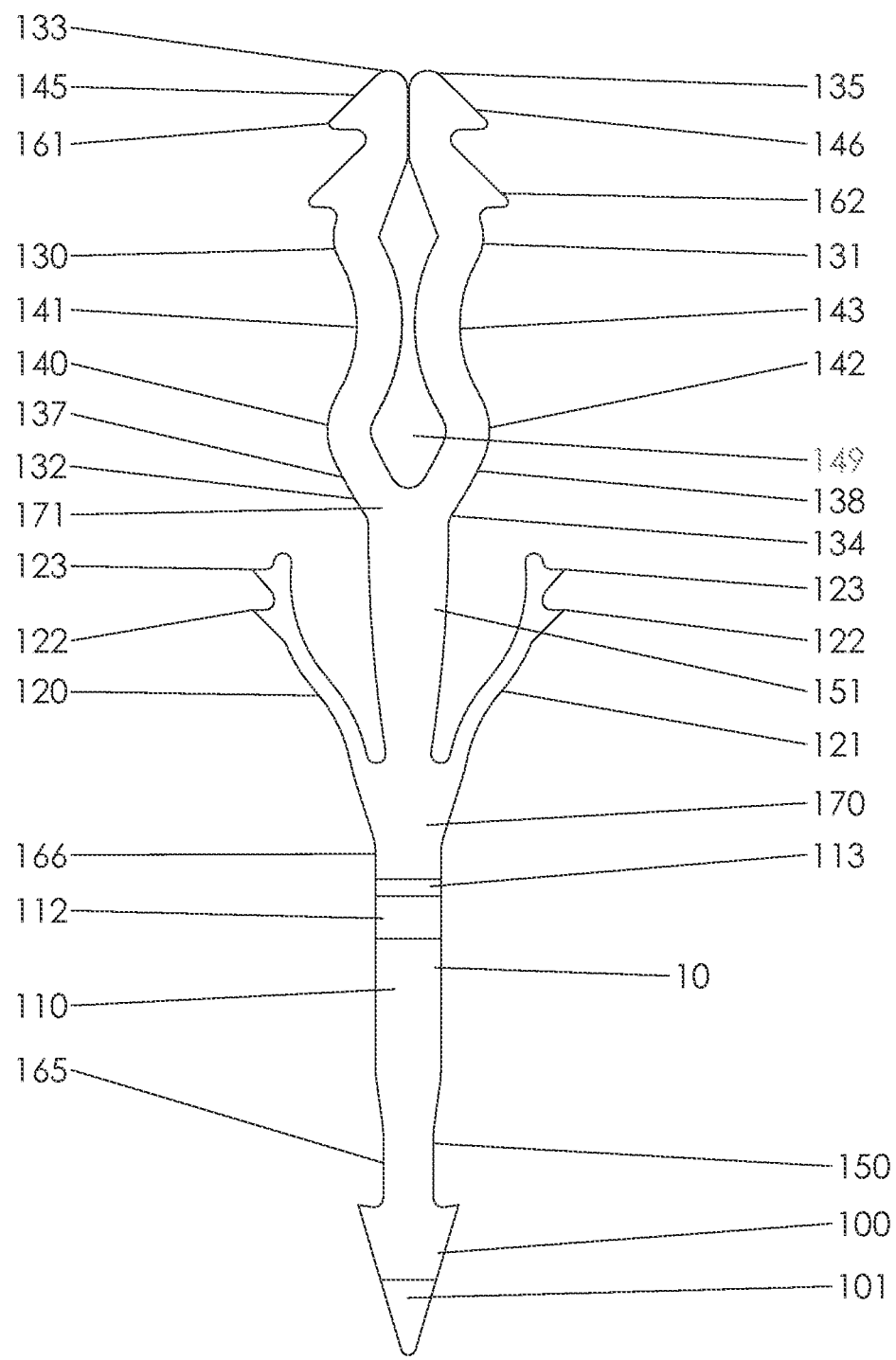
FIG. 7 is a top view illustrating the implant including the wings in the first open insertion shape and the legs in the insertion shape.
Figure 8:
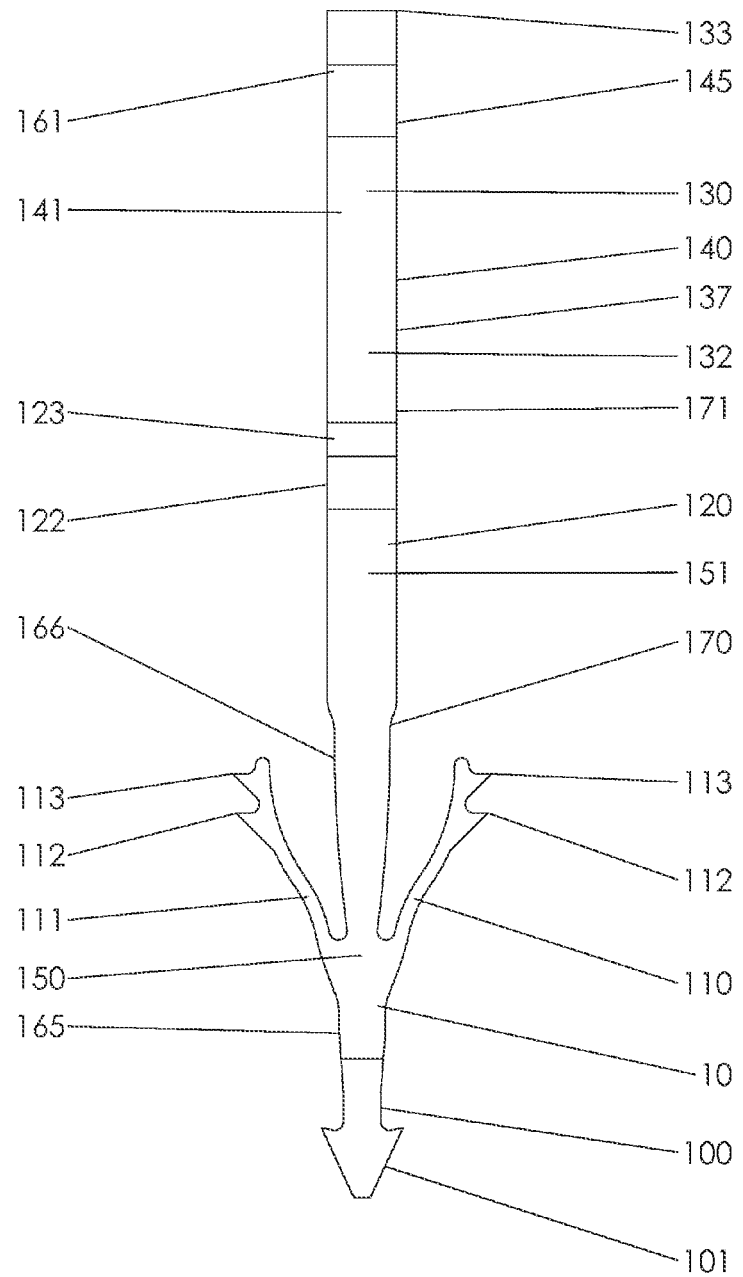
FIG. 8 is a side view illustrating the implant including the wings in the first open insertion shape and the legs in the insertion shape.

FIGS. 1-5 illustrate the wings 110, 111, 120, and 121 in their first open insertion shape and the legs 130 and 131 in their first implanted shape. When the legs 130 and 131 are in their first implanted shape, the barbs 161 and 162 of the tips 145 and 146 engage the intramedullary canal of the second bone to secure and anchor the implant 10 within the intramedullary canal of the second bone. FIGS. 6-8 illustrate the wings 110, 111, 120, and 121 in their first open insertion shape and the legs 130 and 131 in their insertion shape. The legs 130 and 131 are moved to their insertion shape by an external force and held in their insertion shape through contact with the implant insertion device 40 at the bends 140 and 141. Movement of the legs 130 and 131 to their insertion shape facilitates insertion the implant 10 into the intramedullary canal of the second bone.

In order to fixate a first bone to a second bone, the legs 130 and 131 are moved to their insertion shape, which, in the preferred embodiment, entails applying an external force that moves the legs 130 and 131 to their insertion shape. After the legs 130 and 131 move to their insertion shape, the implant 10 loads onto the implant insertion device 40, and the legs 130 and 131 are held in their insertion shape through contact with the implant insertion device 40 at the bends 140 and 141. Once the implant 10 loads onto the implant insertion device 40, the implant 10 is ready for insertion into the intramedullary canal of the first bone.

As previously described, the wings 110, 111, 120, 121, and the legs 130 and 131 incorporate the superelastic or shape memory properties of the implant 10, and thus can adapt to the intramedullary canal of the first and second bone. The design of the wings 110, 111, 120, and 121 allows the wings 110, 111, 120, and 121 to begin in a first open insertion shape and then move to an implanted shape that conforms to the shape of the intramedullary canal of the first bone when inserted. The wings 110, 111, 120, and 121 during insertion accordingly conform and assume various constrained positions depending on the anatomy. Moreover, the positioning of the wings 110 and 111 and the wings 120 and 121 with distal ends trailing the direction of insertion facilitates insertion of the implant 10 into the intramedullary canal of the first bone. The wings 110 and 111 and the wings 120 and 121 upon insertion begin to flex due to the force imparted into the wings 110, 111, 120, and 121 by the reduced diameter of the intramedullary canal of the first bone. The wings 110 and 111 and the wings 120 and 121 constrain and conform to the shape of the intramedullary canal of the first bone due to the superelastic or shape memory properties of the implant 10. In addition, the barbs 113 and 123 secure and anchor the wings 110 and 111 and the wings 120 and 121, respectively, to the intramedullary canal of the first bone. After insertion, the anchoring force imparted to the wings 110, 111, 120, and 121 due to their the superelastic properties allows the implant 10 to engage and anchor the implant 10 within the intramedullary canal of the first bone and resist any motion outward from the first bone.

In order to facilitate insertion into the second bone, the legs 130 and 131 are held in their insertion shape by the implant insertion device 40. The legs 130 and 131 insert into the intramedullary canal of the second bone and the implant insertion device 40 is removed. After insertion of the legs 130 and 131 of the implant 10 into the intramedullary canal of the second bone and removal of the implant insertion device 40, the superelastic properties of the implant 10 return the legs 130 and 131 to their first implanted shape such that an anchoring force created between the legs 130 and 131 and the second bone anchors the legs 130 and 131 within the intramedullary canal in the second bone. Upon returning to their first implanted shape, the barbs 161 and 162 of the tips 145 and 146 engage and anchor the legs 130 and 131 and therefore the implant 10 to the intramedullary canal of the second bone. The anchoring force created by legs 130 and 131 within the second bone is opposite of the anchoring force of the wings 110, 111, 120, and 121 within the first bone. The opposing anchoring forces between the legs 130 and 131 and the wings 110, 111, 120, 121 creates compression at the second body section 151. The operation of the wings 110 and 111, the wings 120 and 121, and the legs 130 and 131 in securing the implant 10 into the intramedullary canal of the first and second bone will be explained in greater detail herein.

In the preferred embodiment, the implant 10 includes wings 110 and 111, wings 120 and 121, and legs 130 and 131, nevertheless, one of ordinary skill in the art will recognize that any number of wings and legs may be used to accomplish a particular objective. In addition, in the preferred embodiment, the wings 110 and 111 are perpendicular in orientation to the wings 120 and 121 and the legs 130 and 131, however, one of ordinary skill in the art will recognize that the wings 110 and 111, the wings 120 and 121, and legs 130 and 131 may be coplanar, perpendicular, or any relative angle with each other.

Figure 9:
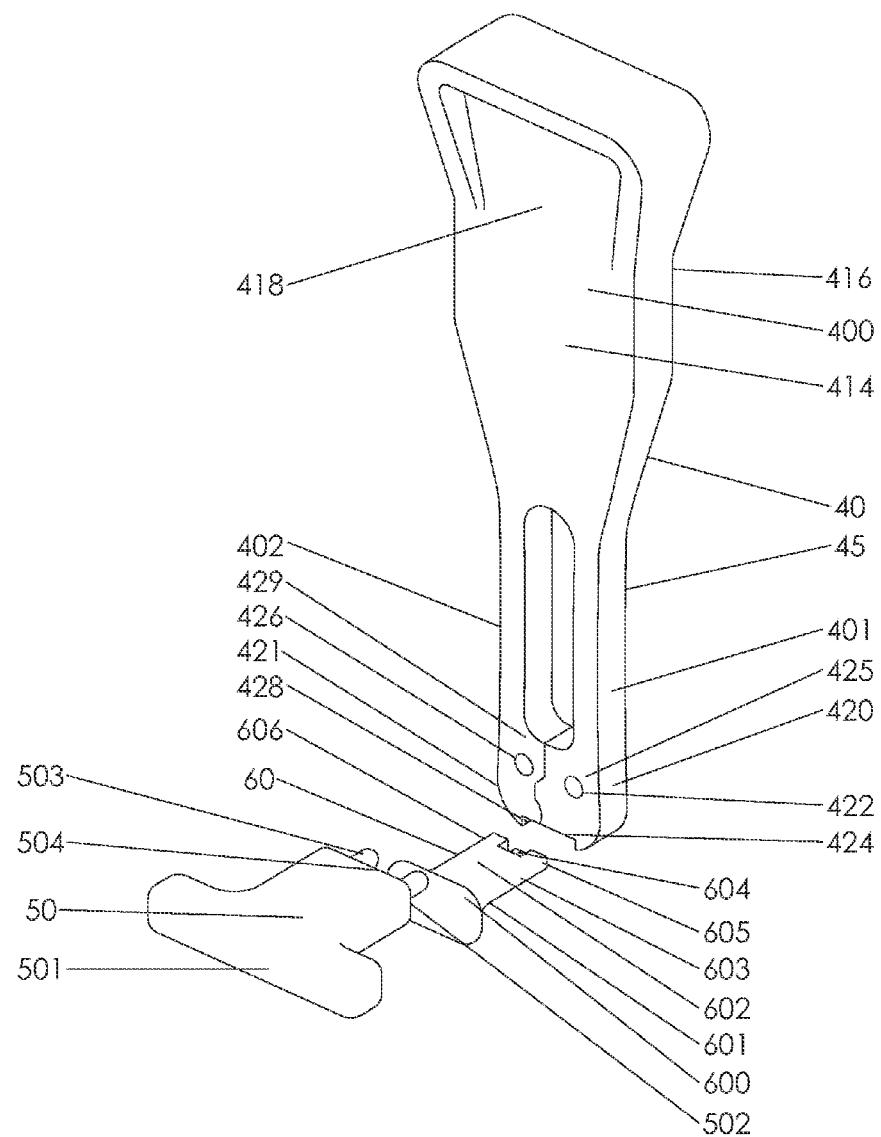
FIG. 9 is a perspective view illustrating an implant insertion device including an implant tab, an inserter tab, and an implant inserter in an engaged position.

FIG. 9 illustrates the implant insertion device 40, which includes an implant inserter 45, an inserter tab 50, and an implant tab 60. The implant insertion device 40 moves between a disengaged position and an engaged position that secures the implant 10 and maintains the implant 10 in the second shape. In addition, the implant insertion device 40 allows a surgeon to manipulate the implant 10 and insert the implant 10 into tissue or bones that require fixation. The implant insertion device 40 can be made of any suitable material; however, in the preferred embodiment the implant insertion device 40 is made from plastic.

The implant tab 60 of the implant insertion device 40 engages the implant 10 to allow manipulation thereof. The implant tab 60 further functions as a stop to prevent overinsertion of the implant 10. The inserter tab 50 of the implant insertion device 40 is designed for use during the movement of the implant insertion device 40 between its disengaged position and its engaged position. Both the implant tab 60 and the inserter tab 50 interface with the implant inserter 45 of the implant insertion device 40 to load and release the implant 10 from the implant inserter 45.

Figure 10:
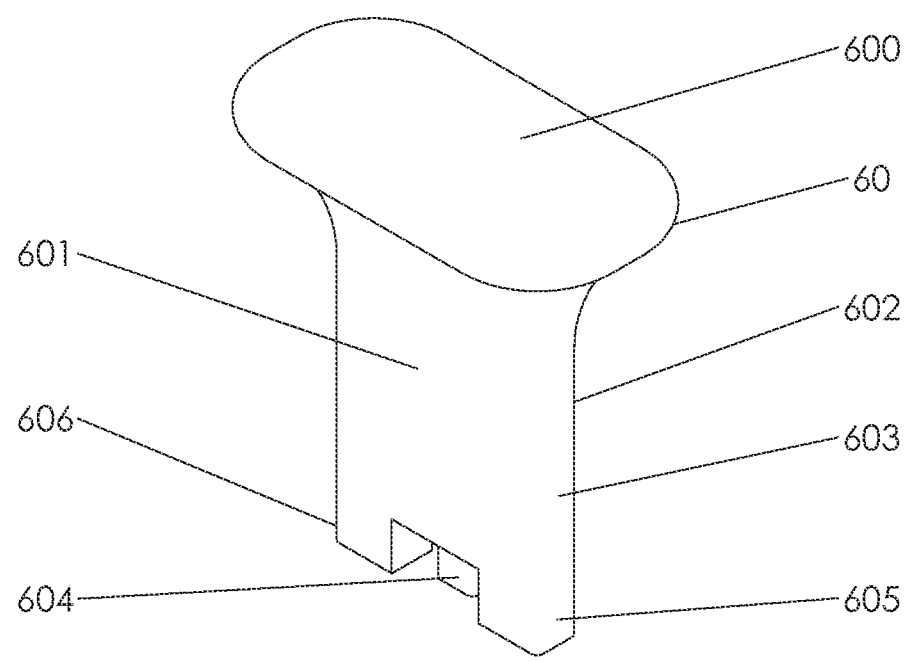
FIG. 10 is a perspective view illustrating the implant tab.
Figure 11:
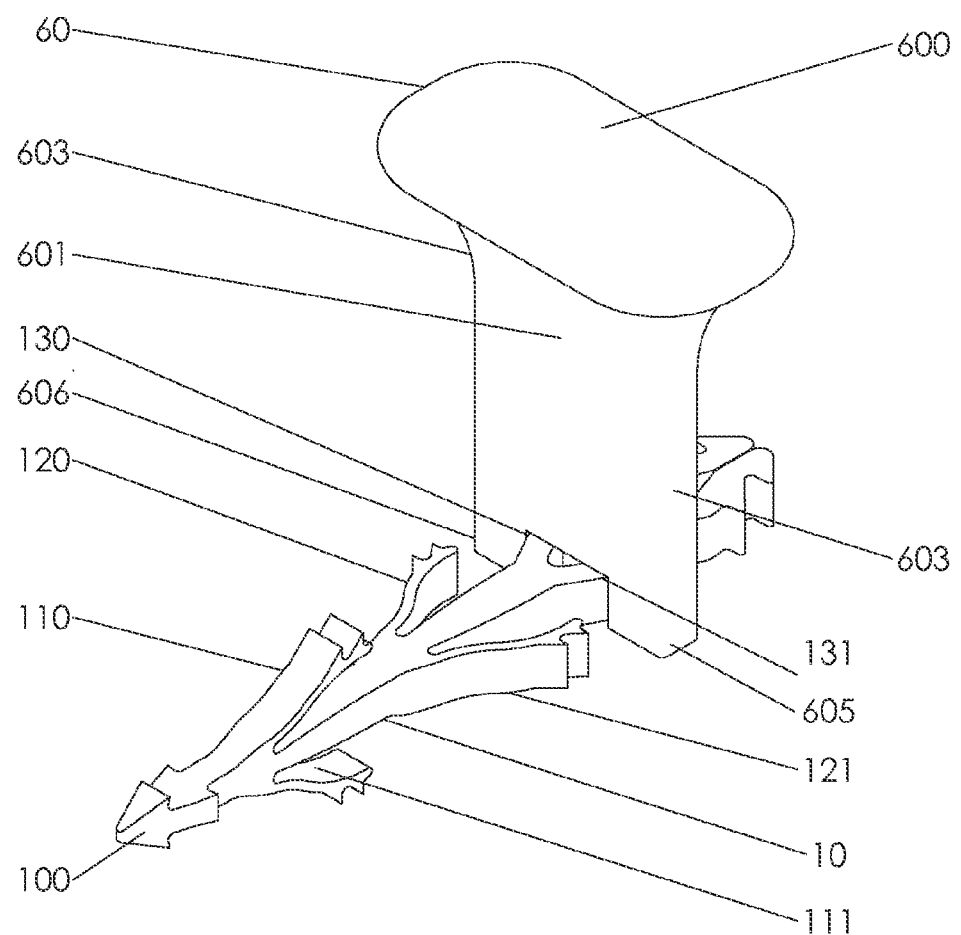
FIG. 11 is a perspective illustrating the implant tab engaging the implant.
Figure 12:
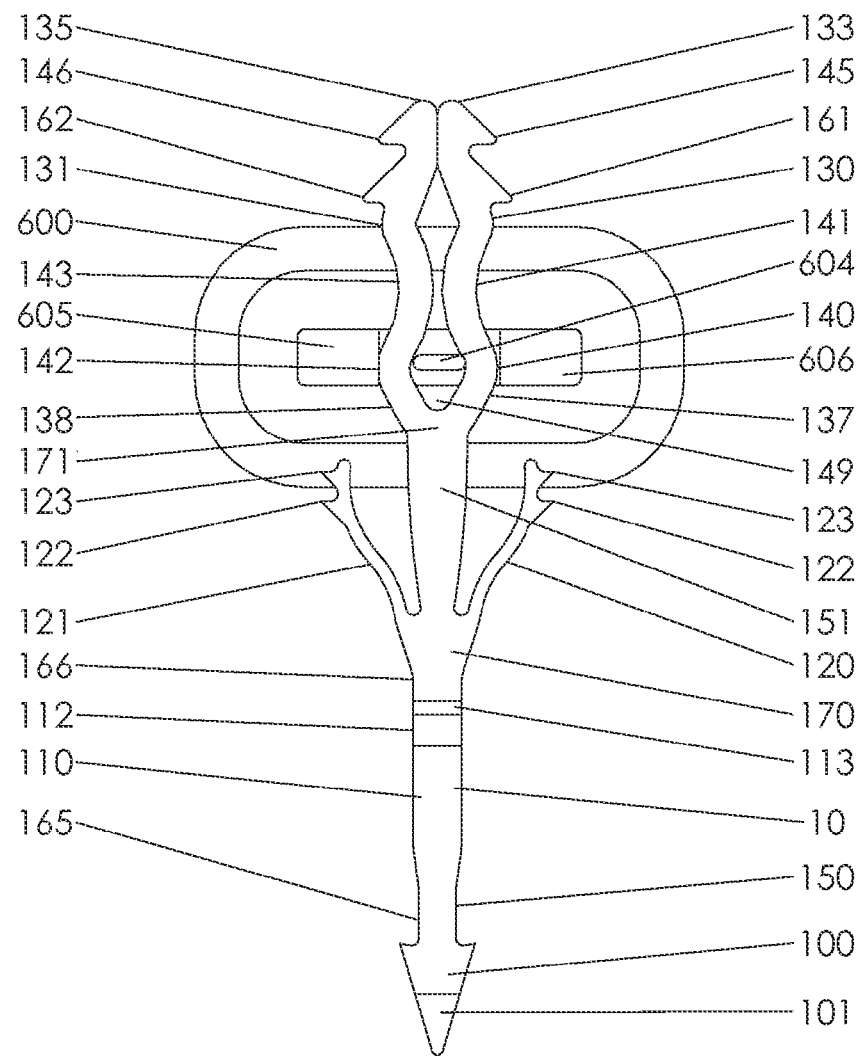
FIG. 12 is a bottom view illustrating the implant tab engaging the implant.

FIGS. 10-12 illustrate the implant tab 60. The implant tab 60 includes a handle 600, front 601, back 602, sides 603, spacer 604, and restraining members 605 and 606. The handle 600 provides a gripping surface to allow a user to manipulate the implant tab 60 and the implant 10 once the implant tab 60 engages the implant 10. The spacer 604 and the restraining members 605 and 606 work in concert to secure and maintain the legs 130 and 131 of the implant 10 in their insertion shape.

In order for the implant tab 60 to engage the implant 10, an external force applied to the implant 10 moves the legs 130 and 131 to their insertion shape. Specifically, in accordance with the preferred embodiment, the external force is applied to the legs 130 and 131 of the implant 10 to move the legs 130 and 131 from their first implanted shape to their insertion shape. More specifically, the applied external force moves the leg 130 at the transition section 137 and the leg 131 at the transition section 138 until the tip 145 of the leg 130 and the tip 146 of the leg 131 abut. The spacer 604 of the implant tab 60 inserts into the aperture 149 formed between the bends 140 and 142 of the legs 130 and 131, and the restraining members 605 and 606 of the implant tab 60 clasp the bends 140 and 141 of the legs 130 and 131, thereby maintaining the legs 130 and 131 in their insertion shape. In the preferred embodiment, the restraining members 605 and 606 of the implant tab 60 clasp the bends 140 and 141 of the legs 130 and 131 such that the transition sections 137 and 138 of the legs 130 and 131 remain exterior relative to the front 601 of the implant tab 60.

Figure 13:
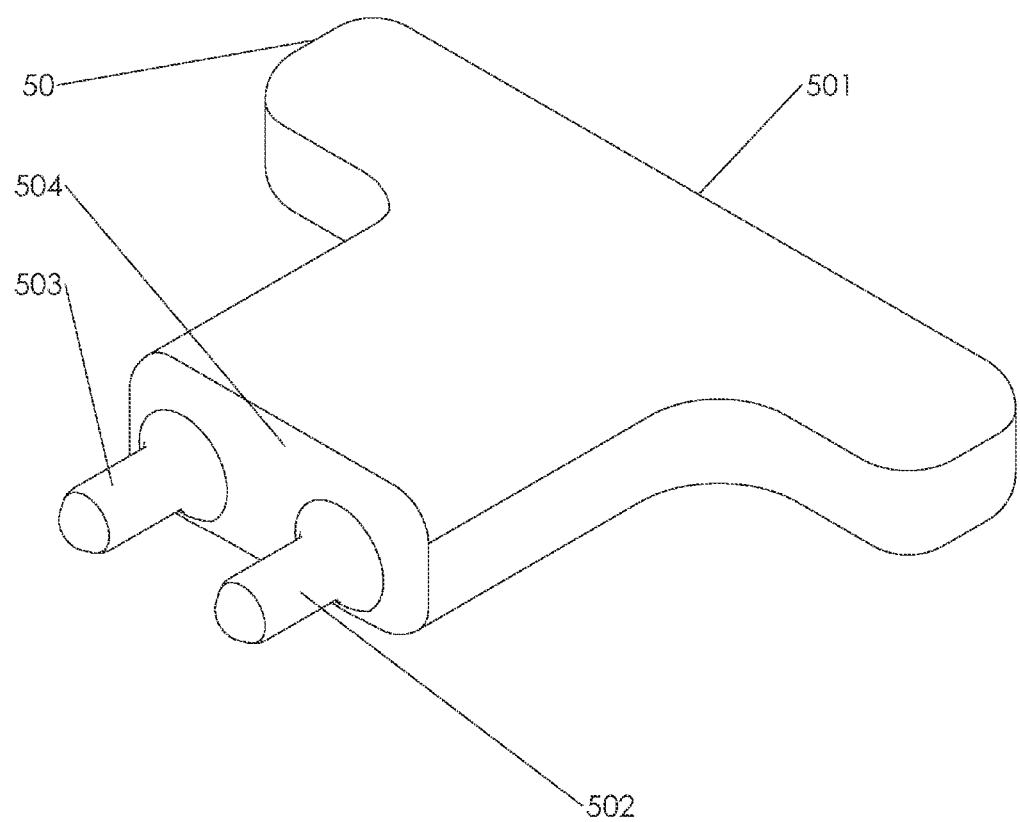
FIG. 13 is a perspective view illustrating the inserter tab.
Figure 14:
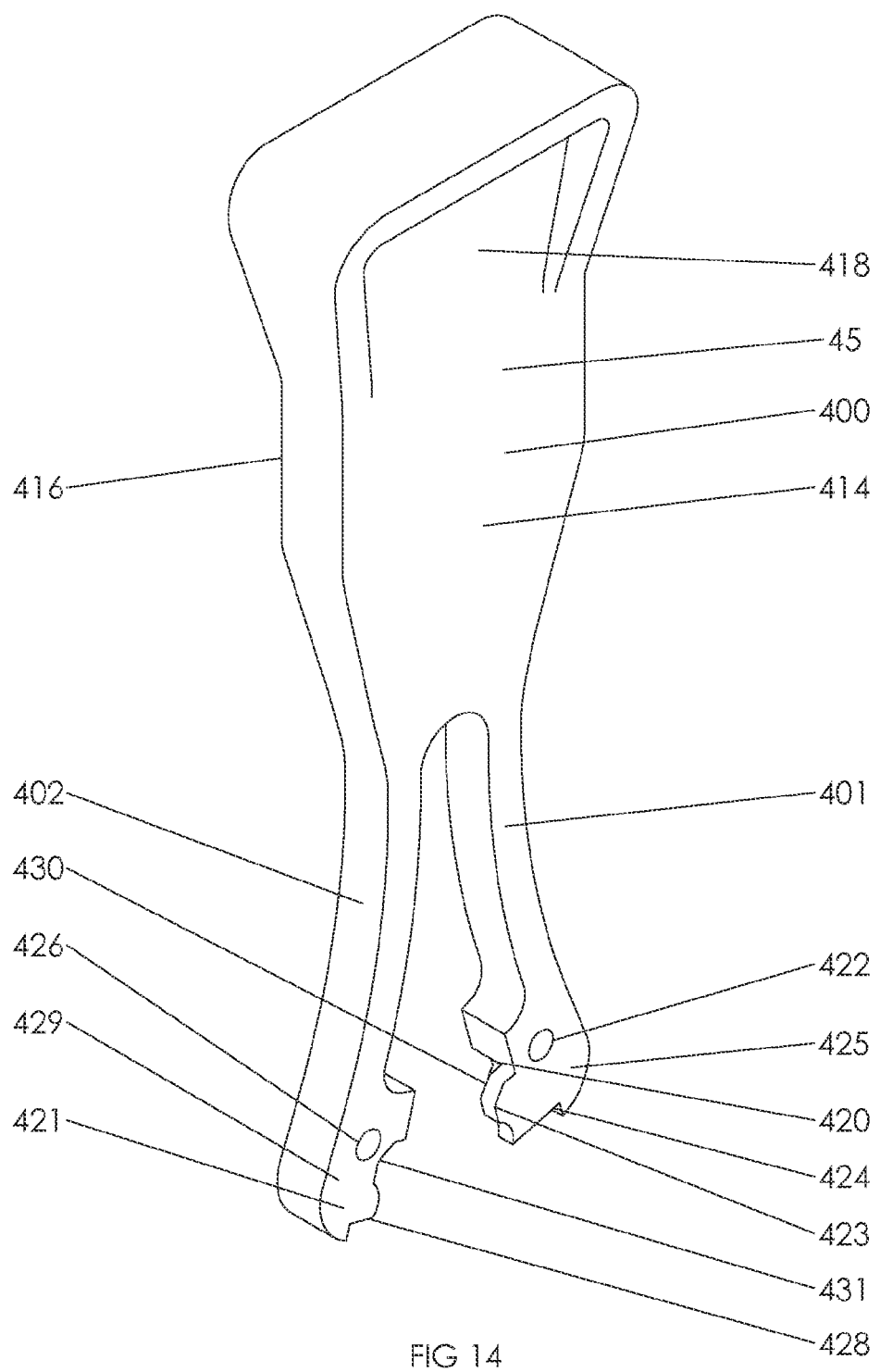
FIG. 14 is a rear perspective view illustrating the implant inserter in a disengaged position.
Figure 15:
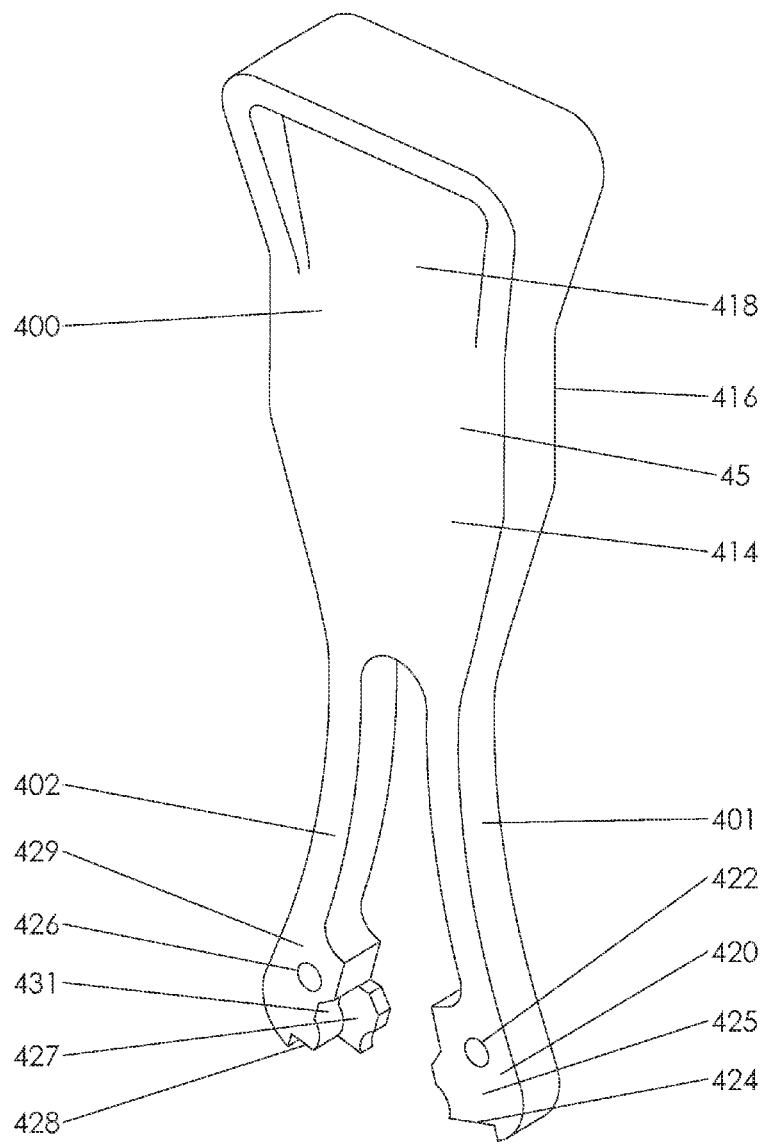
FIG. 15 is a front perspective view illustrating the implant inserter in a disengaged position.

FIGS. 13-15 illustrate the inserter tab 50 and the implant inserter 45. The inserter tab 50 includes a handle 501, pins 502 and 503, and a jaw interface 504. The implant inserter 45 includes a body 400 and arms 401 and 402. The body 400 of the implant inserter 45 includes a front 414, a back 416, and a handle 418. The handle 418 provides a gripping surface on the front 414 and the back 416 of the body 400. The gripping surface of the handle 418 allows a surgeon to manipulate the implant inserter 45 and therefore the implant 10. The arms 401 and 402 are formed integral with the body 400 and include jaws 420 and 421. The arms 401 and 402 move between a normally open position and a closed position.

The jaw 420 includes a pinhole 422, a key 423, an implant tab interface 424, an inserter tab interface 425, and a key slot 430. The jaw 421 includes a pinhole 426, a key 427, an implant tab interface 428, an inserter tab interface 429, and a key slot 431. The jaws 420 and 421 move between an unlocked position and a locked position. The locked position allows the jaws 420 and 421 to secure to the implant 10, the implant tab 60, and the inserter tab 50 to facilitate the insertion of the implant 10 into tissue or bone. The unlocked position facilitates the removal of the implant 10 and the implant tab 60 from the jaw 420 and 421.

Figure 16:
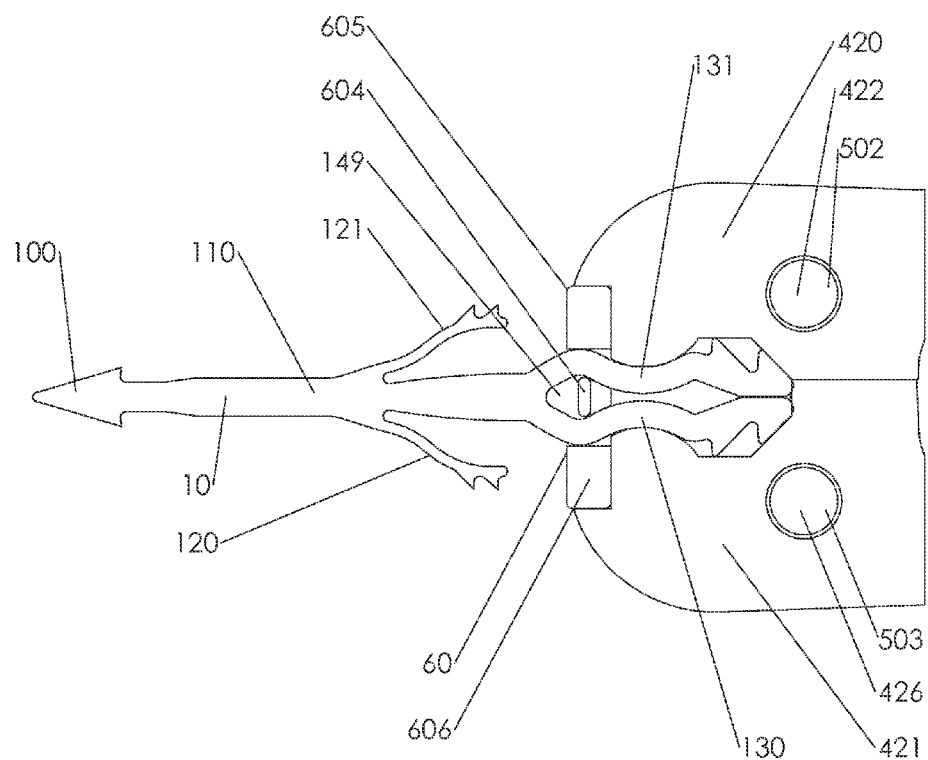
FIG. 16 is a bottom view illustrating the implant insertion device loaded with the implant.

The key 423 of the jaw 420 engages the key slot 431 of the jaw 421 and the key 427 of the jaw 421 engages the key slot 430 of the jaw 420 when the jaws 420 and 421 move from their unlocked to their locked position. In addition, as illustrated in FIG. 16, the key 423 and the key slot 430 of the jaw 420 and the key 427 and the key slot 431 of the jaw 421 form an implant retention cavity 435 when the jaws 420 and 421 are in their locked position. Furthermore, the implant tab interface 424 of the jaw 420 and the implant tab interface 428 of the jaw 421 engage and secure the implant tab 60 to the implant inserter 45 when the jaws 420 and 421 move from their unlocked to their locked position.

Once the jaws 420 and 421 reach their locked position, the implant retention cavity 435 secures the legs 130 and 131 of the implant 10 within the implant inserter 45, and the implant tab interface 424 of the jaw 420 and the implant tab interface 428 of the jaw 421 engage and secure the implant tab 60 to the implant inserter 45. In particular, after the implant 10 secures to the implant tab 60, the implant tab 60 along with the secured implant 10 is ready to be loaded within the jaws 420 and 421 of the implant inserter 45. The legs 130 and 131 of the implant 10 insert between the jaws 420 and 421 and align with the key 423 and the key slot 430 of the jaw 420 and the key 427 and the key slot 431 of the jaw 421. As illustrated in FIG. 16, the jaws 420 and 421 are then moved to their locked position, thereby loading the implant 10 within the implant retention cavity 435 of the implant inserter 45. Specifically, the bow 141 and the tip 145 of the leg 130 and the bow 143 and the tip 146 of the leg 131 reside and are secured within the implant retention cavity 435. In addition, as the jaws 420 and 421 move to their locked position, the back 602 and sides 603 of the implant tab 60 interface with the implant tab interface 424 of the jaw 420 and the implant tab interface 428 of the jaw 421 thereby loading the implant inserter 45 with the implant tab 60.

After the implant insertion device 45 has been loaded with the implant tab 60 and implant 10, the inserter tab 50 is ready to engage and secure to the implant insertion device 45. The pinhole 422 and the inserter tab interface 425 of the jaw 420 as well the pinhole 426 and the inserter tab interface 428 of the jaw 421 engage the inserter tab 50. In particular, the inserter tab 50 is designed to maintain the arms 401 and 402 of the implant inserter 45 in their closed position and the jaws 420 and 421 of the implant inserter 45 in their locked position. The handle 501 of the inserter tab 50 provides a gripping surface to allow a user to manipulate the inserter tab 50. The pin 502 inserts within the pinhole 422 of the jaw 420 and the pin 503 inserts within the pinhole 426 of the jaw 421 until jaw interface 503 of the inserter tab 50 is flush with the inserter tab interface 425 of the jaw 420 and the inserter tab interface 429 of the jaw 421. Once the jaw interface 504 of the inserter tab 50 is flush with the inserter tab interface 425 of the jaw 420 and the inserter tab inserter tab interface 429 of the jaw 421, the inserter tab 50 maintains the arms 401 and 402 of the implant inserter 45 in their closed position and the jaws 420 and 421 of the implant inserter 45 in their locked position. Removal of the inserter tab 50 from the implant inserter 45 such that the pins 502 and 503 disengage respectively from the pinholes 422 and 426 releases the jaws 420 and 421, thereby allowing movement of the arms 401 and 402 from their closed position to their normally open position and the jaws 420 and 421 from their locked to their unlocked position.

Figure 17:
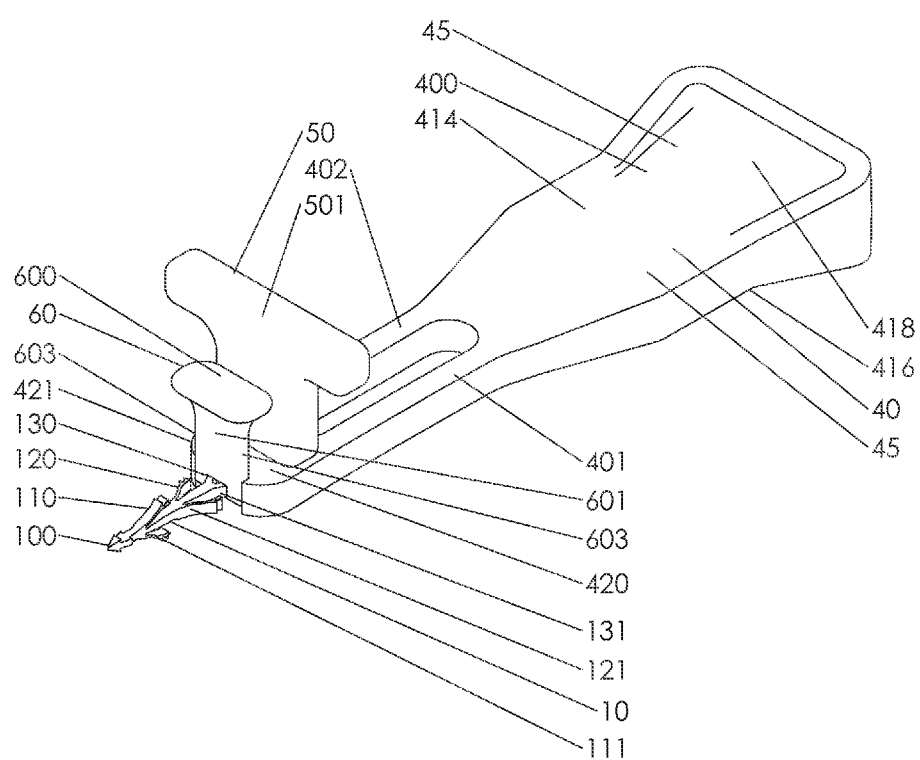
FIG. 17 is a perspective view illustrating the implant insertion device loaded with the implant.

As illustrated in FIG. 17, loading the implant inserter 45 with the implant 10 and the implant tab 60, moving the jaws 420 and 421 from their unlocked to their locked position, and securing the inserter tab 50 to the implant inserter 45 places the implant insertion device 40 into the engaged position. With the implant insertion device 40 loaded with the implant 10 and placed in its engaged position, the implant 10 is ready for insertion into the intramedullary canal of the first bone.

Figure 18:
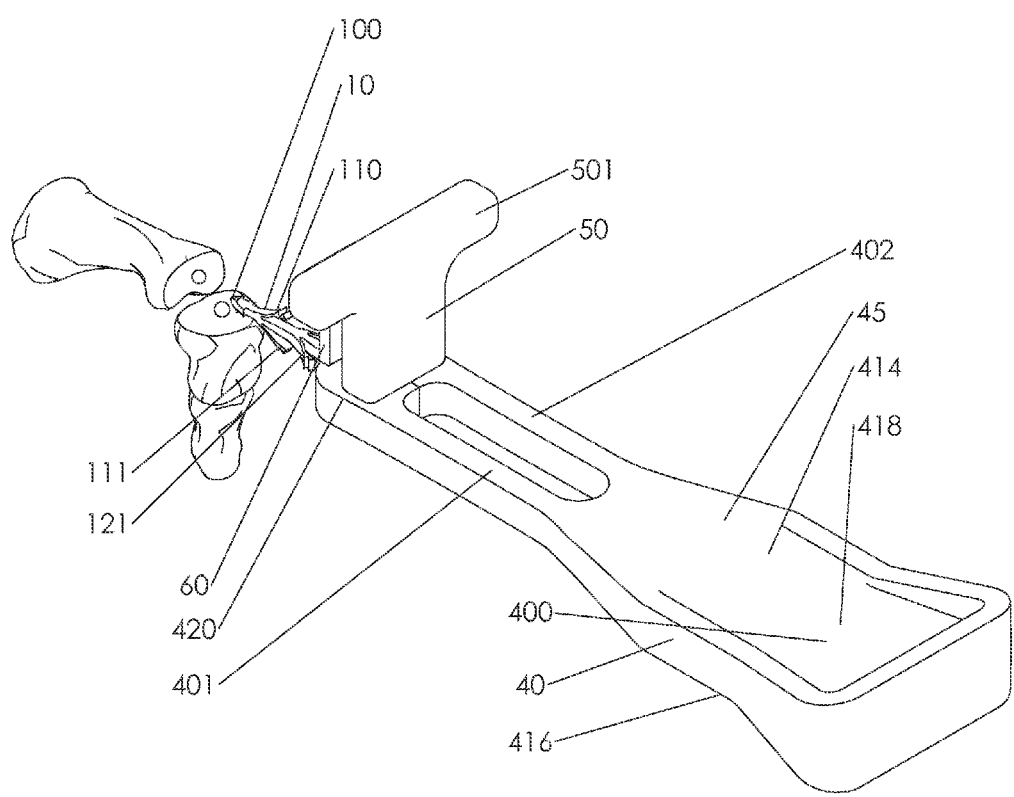
FIG. 18 is a perspective view illustrating insertion of the implant into an intramedullary canal of a first bone.
Figure 19:
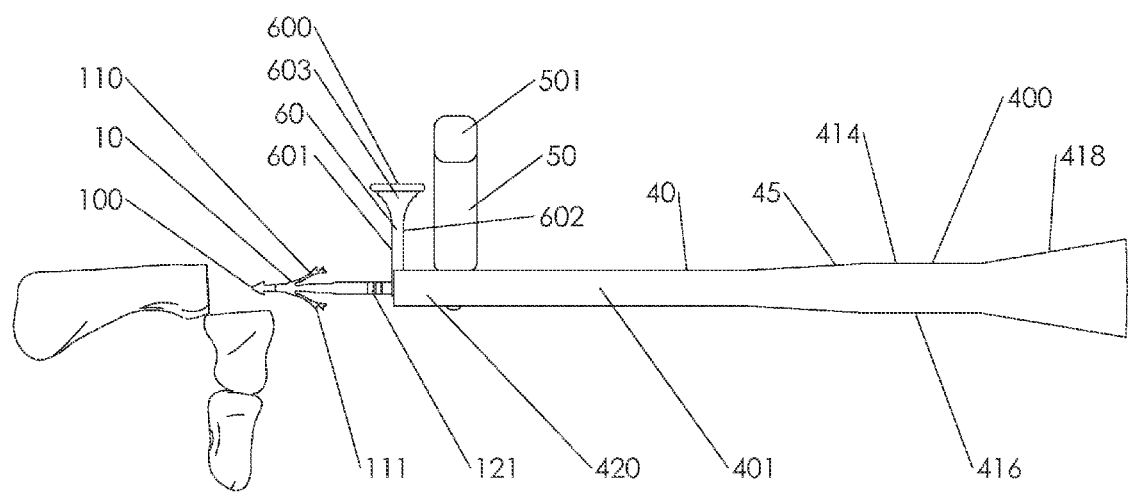
FIG. 19 is a side view illustrating insertion of the implant into the intramedullary canal of the first bone.
Figure 20:
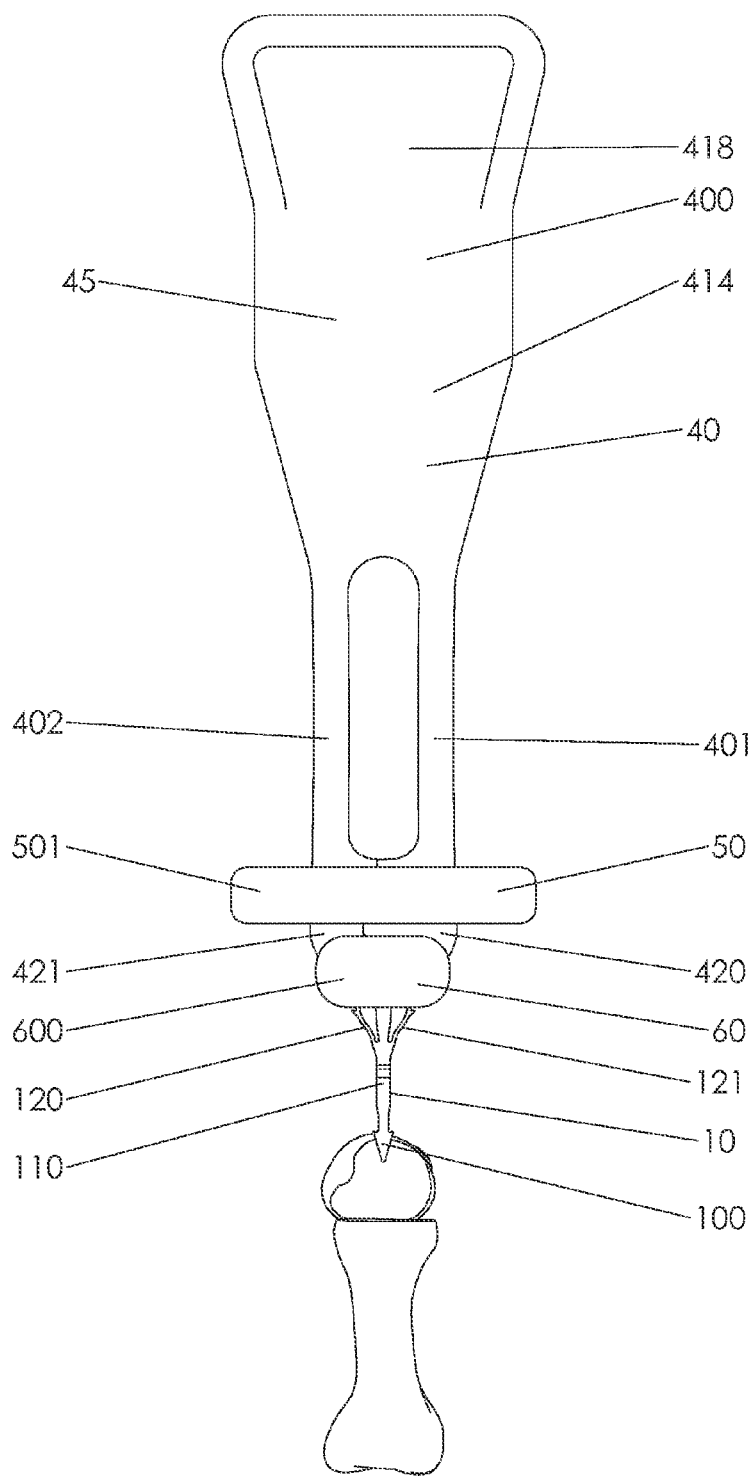
FIG. 20 is a top view illustrating insertion of the implant into the intramedullary canal of the first bone.
Figure 21:
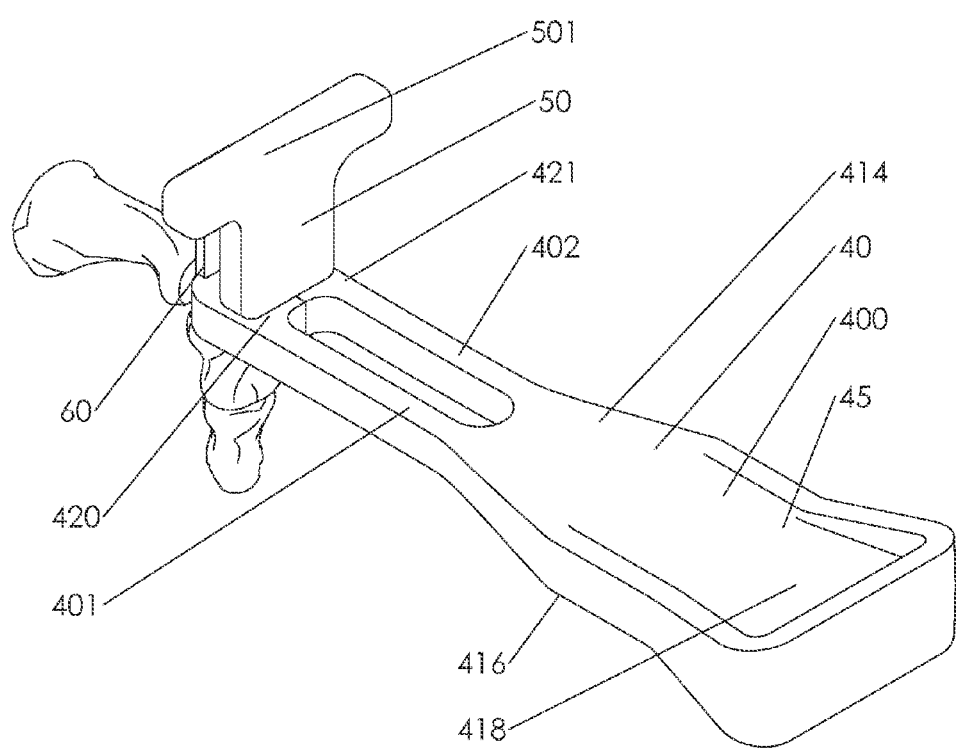
FIG. 21 is a perspective view illustrating the implant inserted into the intramedullary canal of the first bone.

As illustrated in FIGS. 18-20, a surgeon orients the implant insertion device 40 and the loaded implant 10 such that the head 100 of the implant 10 aligns with the intramedullary canal of the first bone. As illustrated in FIG. 21, after the head 100 of the implant 10 aligns with the intramedullary canal of the first bone, the surgeon inserts the implant 10 within the intramedullary canal until the front 601 of the implant tab 60 abuts the first bone. Specifically, as the implant 10 inserts into the intramedullary canal, the wings 110 and 111 and the wings 120 and 121 of the implant 10 begin to flex due to the force imparted into the wings 110, 111, 120, and 121 by the reduced diameter of the intramedullary canal of the first bone. More specifically, the wings 110 and 111 flex towards the first body section 150 and the wings 120 and 121 flex towards the second body section 151 during insertion into the intramedullary canal of the first bone, thereby imparting a force to the wings 110, 111, 120, and 121. Due to the superelastic properties of the implant 10, the flexing of the wings 110, 111, 120, and 121 causes the wings 110, 111, 120, and 121 to move from their first open insertion shape to their implanted shape that conforms with the intramedullary canal of the first bone. After insertion into the intramedullary canal of the first bone, the wings 110, 111, 120 and 121 apply the anchoring force against the intramedullary canal such that the barbs 113 and 123 secure and anchor the wings 110 and 111 and the wings 120 and 121, respectively, thereby resisting any motion outward from the first bone. Likewise, the barbs 101 anchor the head 100 to the intramedullary canal of the first bone, thereby resisting any motion outward from the first bone.

Figure 22:
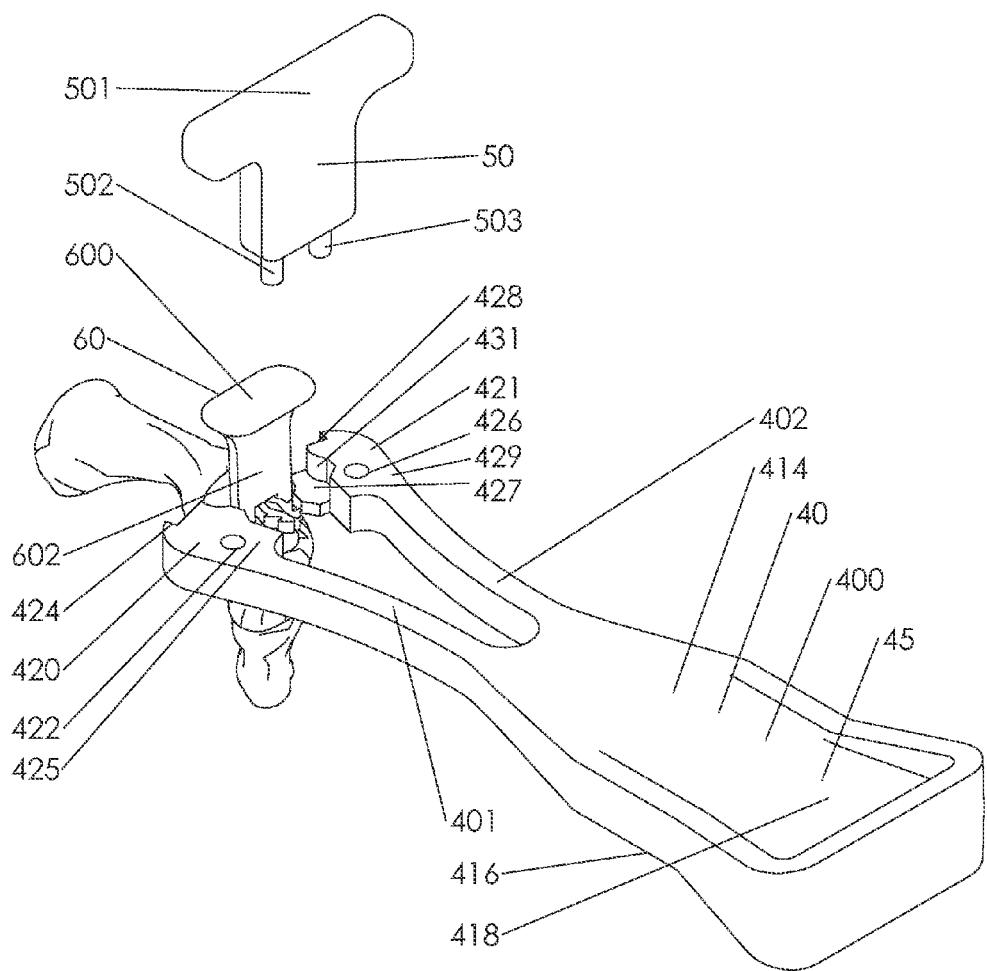
FIG. 22 is a perspective view illustrating removal of the implant inserter from the implant after insertion of the implant into the intramedullary canal of the first bone.

After insertion of the implant 10 into the intramedullary canal of the first bone, the implant 10 and the implant tab 60 are ready to be removed from the implant inserter 45. As illustrated in FIG. 22, the inserter tab 50 is removed from the implant inserter 45 such that the pins 502 and 503 disengage respectively from the pinhole 422 of the jaws 420 and the pinhole 426 of the jaws 421. Removal of the inserter tab 50 from the implant inserter 45 releases the jaws 420 and 421, thereby allowing movement of the arms 401 and 402 from their closed position to their normally open position and the jaws 420 and 421 from their locked to their unlocked position.

Once the jaws 420 and 421 move to their unlocked position, the key 423 of the jaw 420 disengages the key slot 431 of the jaw 421 and the key 427 of the jaw 421 disengages the key slot 430 of the jaw 420. The disengagement of the key 423 and key 427 and movement of the jaw 420 and 421 to the unlocked position releases the legs 130 and 131 of the implant 10 from the implant retention cavity 435 of the implant inserter 45. In addition, the back 602 and the sides 603 of the implant tab 60 release from the implant tab interface 424 of the jaw 420 and the implant tab interface 428 of the jaw 421. At this point, the inserter tab 50, the implant tab 60, and the implant 10 have been removed from the implant inserter 45, and the implant 10 is now ready for insertion into the intramedullary canal of the second bone.

Figure 23:
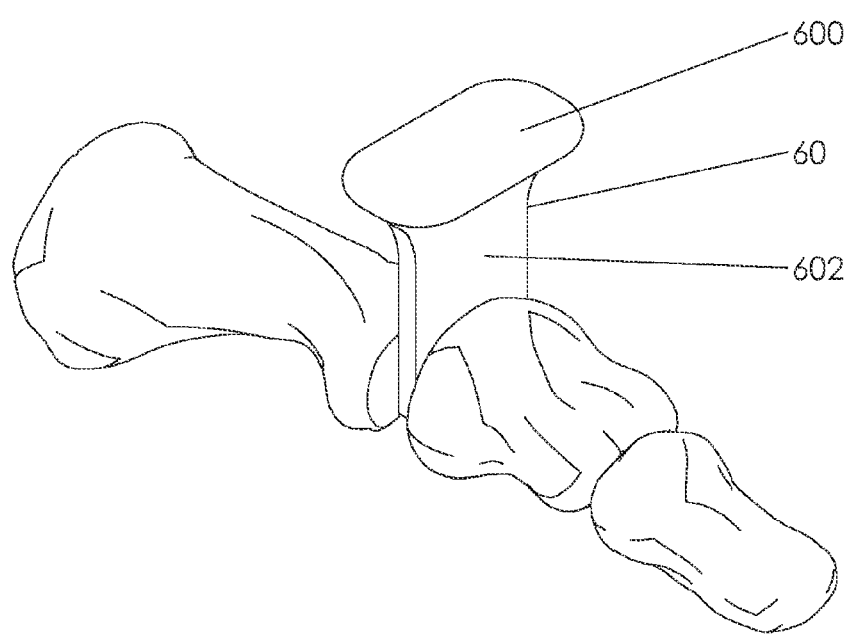
FIG. 23 is a perspective view illustrating the implant inserted into an intramedullary canal of a second bone.

As illustrated in FIG. 23, the surgeon orients the second bone and the first bone with the inserted implant 10 such that the distal ends 133 of the legs 130 and 131 align with the intramedullary canal of the second bone. After the distal ends 133 of the legs 130 and 131 align with the intramedullary canal of the second bone, the surgeon inserts the legs 130 and 131 of the implant 10 within the intramedullary canal until the back 602 of the implant tab 60 abuts the second bone. The use of the implant tab 60 accordingly provides the advantage that the legs 130 and 131 remain constrained until after at least partial insertion into the intramedullary canal of the second bone. After insertion of the legs 130 and 131 into the intramedullary canal of the second bone, the implant tab 60 is ready to be removed from the implant 10 to allow full insertion of the implant 10 within the intramedullary canal of the second bone.

Figure 24:
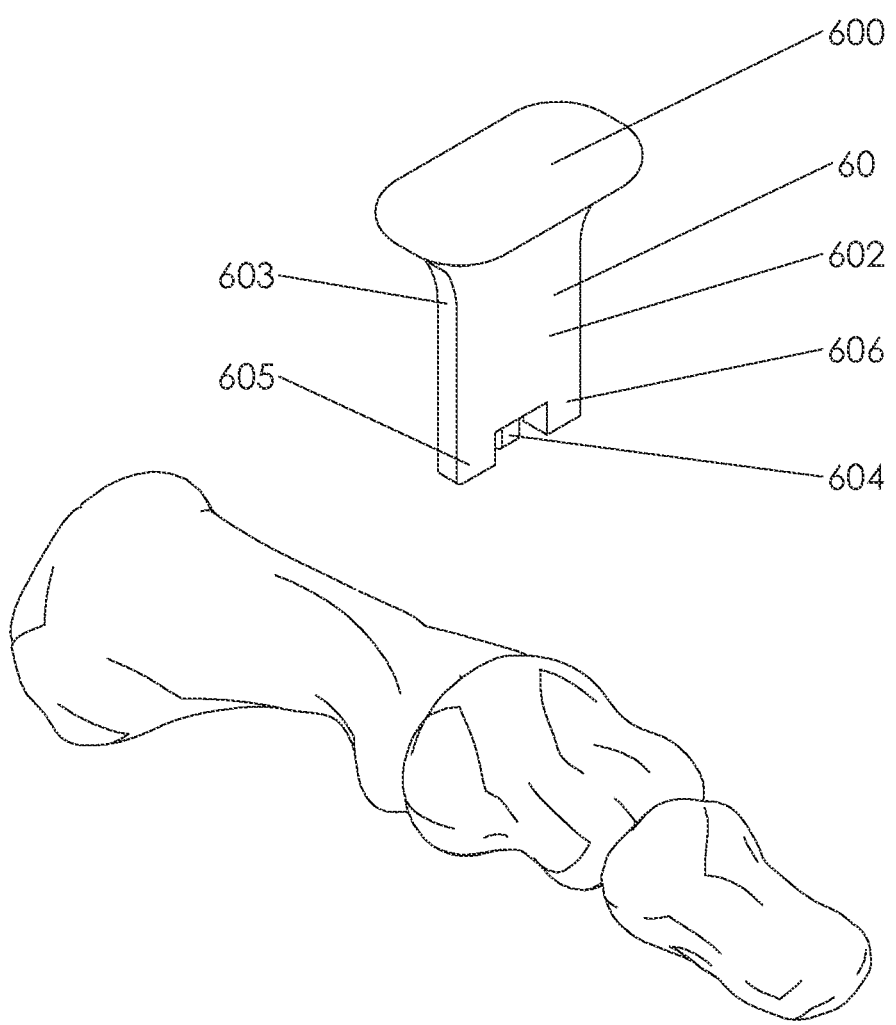
FIG. 24 is a perspective view illustrating disengagement of the implant tab from the implant and insertion of the implant into the intramedullary canal of the second bone.
Figure 25:
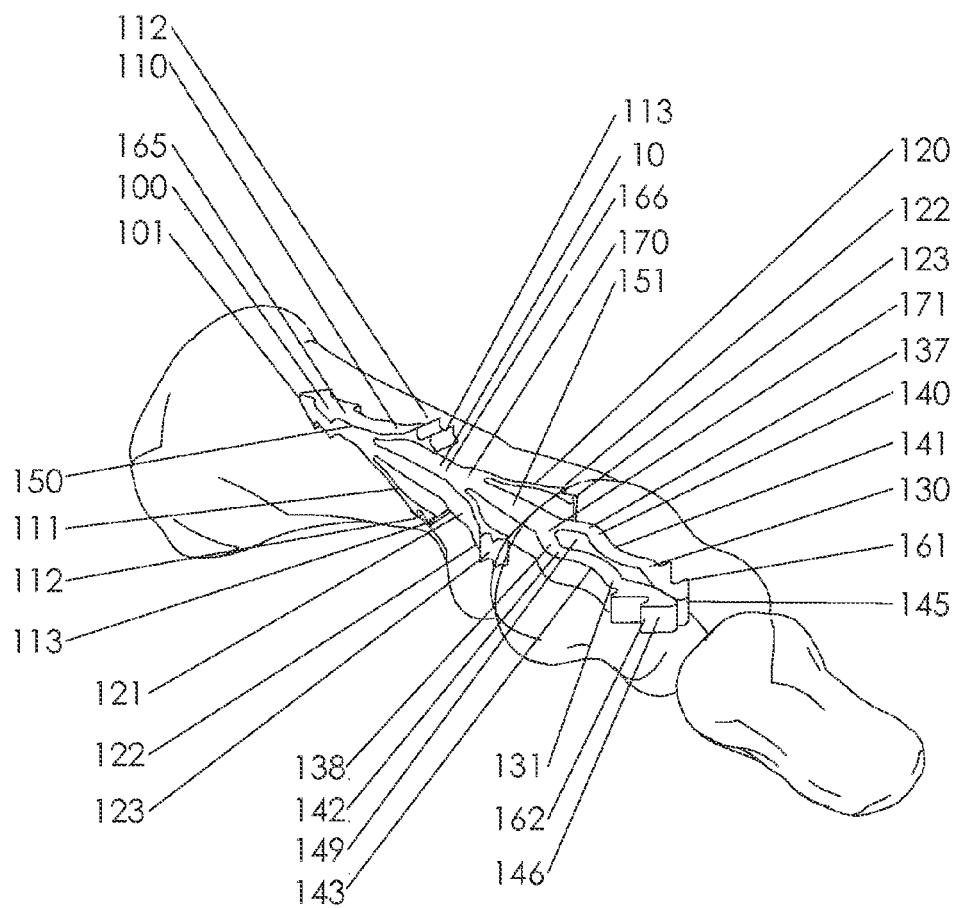
FIG. 25 is a perspective view illustrating the implant inserted into the intramedullary canals of the first and second bones with the wings of the implant in their implanted shape and the legs of the implant in their insertion shape.

The surgeon manipulates the handle 600 of the implant tab 60 to remove the implant tab 60 from the implant 10. As illustrated in FIG. 24, the spacer 604 of the implant tab 60 is removed from the slot 149 formed between the bends 140 and 142 of the legs 130 and 131, and the restraining members 605 and 606 of the implant tab 60 are released from the bends 140 and 141 of the legs 130 and 131. FIG. 25 illustrates the implant 10 once the implant tab 60 has been removed. After removal of the implant tab 60, the surgeon presses the second bone together with the first bone to fully insert the legs 130 and 131 of the implant 10 within the intramedullary canal of the second bone. As the legs 130 and 131 of the implant 10 fully insert into the intramedullary canal of the second bone, the superelastic properties of the implant 10 returns the legs 130 and 131 to their first implanted shape. In particular, the transition sections 137 and 138 travel angularly away from the longitudinal axis 155 such that the tips 145 and 146, the bows 141 and 143, and the bends 140 and 142 diverge, thereby splaying the legs 130 and 131 and returning the legs 130 and 131 to their first implanted shape. Upon returning to their first implanted shape, the barbs 161 and 162 of the tips 145 and 146 engage and anchor the legs 130 and 131 and therefore the implant 10 to the intramedullary canal of the second bone.

Figure 26:
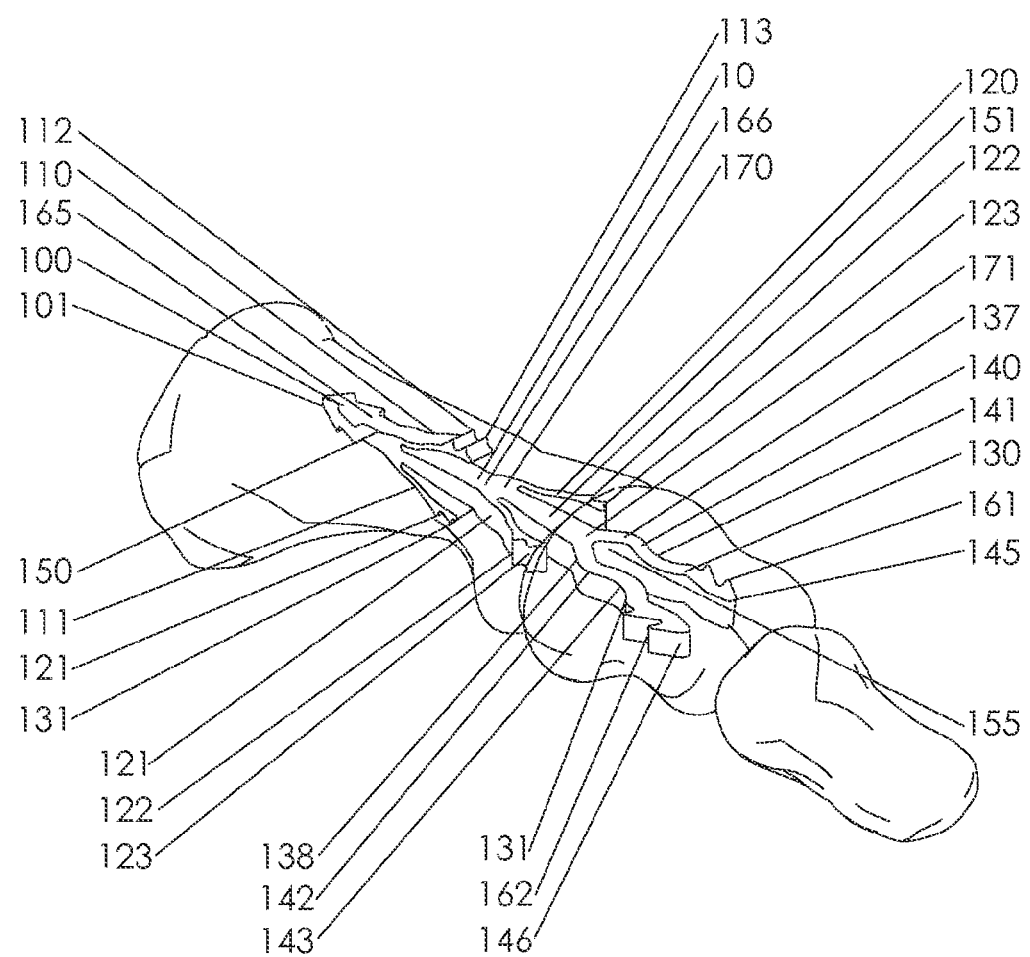
FIG. 26 is a perspective view illustrating the implant inserted into the intramedullary canals of the first and second bones with the wings of the implant in their implanted shape and the legs of the implant in their first implanted shape.
Figure 27:
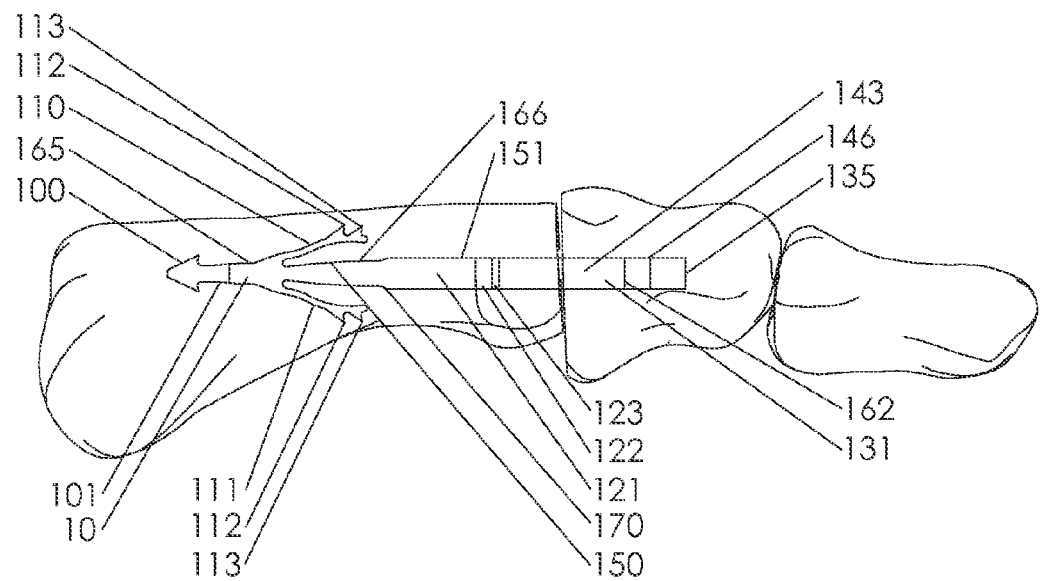
FIG. 27 is a side view illustrating the implant inserted into the intramedullary canals of the first and second bones with the wings of the implant in their implanted shape and the legs of the implant in their first implanted shape.
Figure 28:
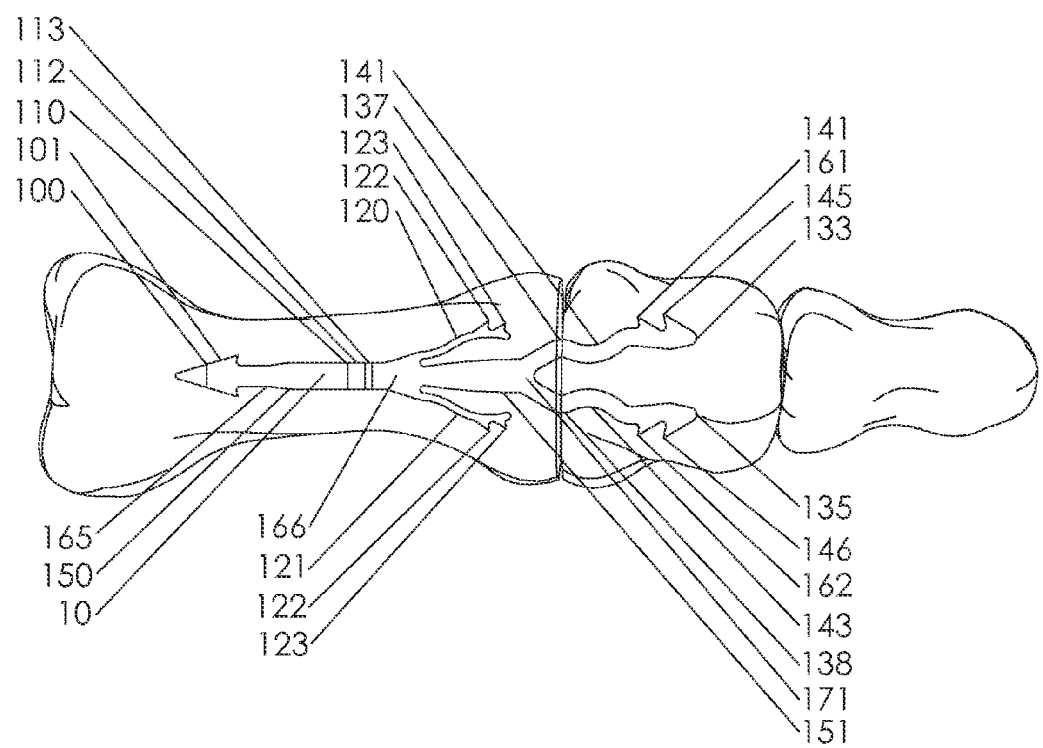
FIG. 28 is a top view illustrating the implant inserted into the intramedullary canals of the first and second bones with the wings of the implant in their implanted shape and the legs of the implant in their first implanted shape.

FIGS. 26-28 illustrate the implant 10 fully inserted within the intramedullary canals of the first and second bones. While the implant 10 may be designed to rest at varying locations between the first and second bones, the implant tab 60 according to the preferred embodiment engages the implant 10 such that the transition sections 137 and 138 of the legs 130 and 131 remain exterior to the front 601 of the implant tab 60. Consequently, insertion of the implant 10 within the intramedullary canal until the front 601 of the implant tab 60 abuts the first bone inserts the transition sections 137 and 138 of the legs 130 and 131 within the intramedullary canal of the first bone. The legs 130 and 131 accordingly span the intramedullary canals of the first and second bone such that the opposing anchoring forces generated between the legs 130 and 131 and the wings 110, 111, 120, 121 creates compression at the second body section 151 of the implant 10, thereby resulting in enhanced compression between the first and second bones as the transition sections 137 and 138 move the legs 130 and 131 to their first implanted positions.

The implant 10 due to its superelastic properties requires no pre-operative freezing for implantation. The wings 110, 111, 120, and 121 begin in a first open insertion shape and deform during insertion to a second shape that conforms with the intramedullary canal of the first bone, thereby anchoring the implant 10 within the first bone. The legs 130 and 131 are mechanically deformed and held in an insertion shape by an implant insertion device 40. Once inserted into the intramedullary canal of the second bone, the legs 130 and 131 are released to return to their first implanted shape that anchors the implant 10 within the second bone and creates compression between the first and second bones. Although the preferred embodiment of the implant 10 incorporates superelastic properties, one of ordinary skill in the art will recognize that certain surgeries may require the implant 10 to incorporate shape memory properties.

Figure 29:
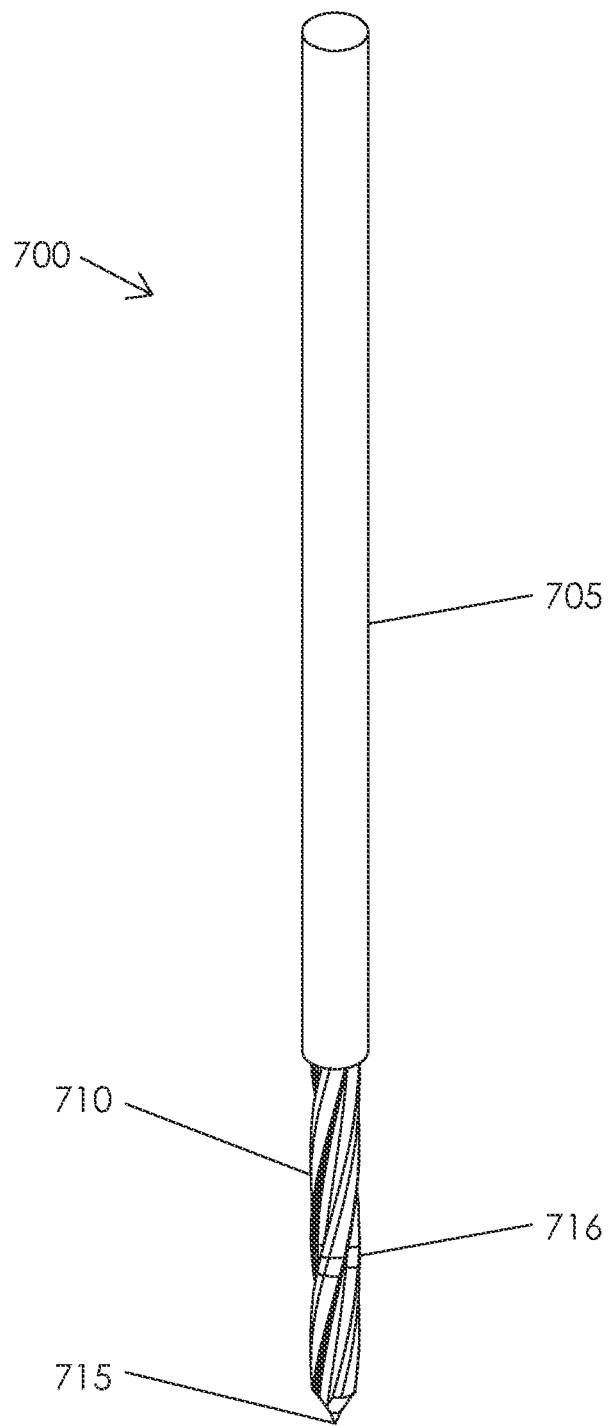
FIG. 29 is a perspective view illustrating a drill bit.

FIG. 29 illustrates a drill bit for making holes in a bone. The drill bit 700 includes a drill bit shank 705, drill bit flutes 710, a drill bit tip 715, and a drill bit marker line 716. The drill bit tip 715 is sharpened, such as a trocar, to prevent skiving of the drill bit 700 during surgical use. The drill bit shank 705 can be smooth, for use with a chuck or pin driver mechanism, or it could include features for quick disconnect. The flutes 710 can extend for any length of the drill bit 700, depending on how deep the application requires. Finally, the drill bit marker line 716 can be located at any point on the drill bit 700 to provide a reference for drill depth. There can be one, or multiple, drill bit marker lines 716.

Figure 30:
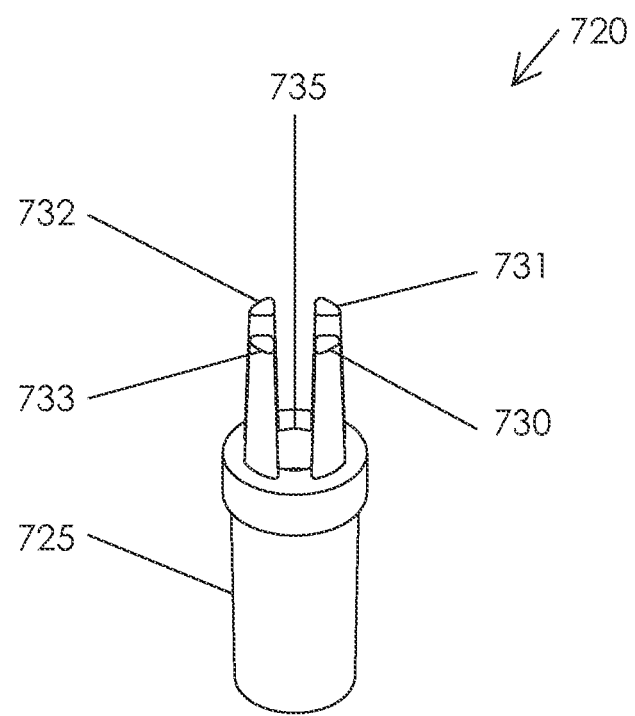
FIG. 30 is a perspective view illustrating a drill bit stop.

FIG. 30 illustrates a drill bit stop 720. The drill bit stop 720 can be made of plastic or metal, and is designed to fit over a drill bit, such as the drill bit 700, to limit the depth of drilling. A drill bit stop body 725 is solid and provides a barrier for drilling. Drill bit stop appendages 730, 731, 732, and 733 provide a flexible friction connection between the drill bit stop 720 and the drill bit 700. There can be any number of drill bit stop appendages, but in this embodiment there are four. Finally, a drill bit stop hole 735 is a through-hole with diameter slightly larger, slightly smaller, or the same as the diameter of the drill bit 700, depending on the desired fit.

Figure 31:
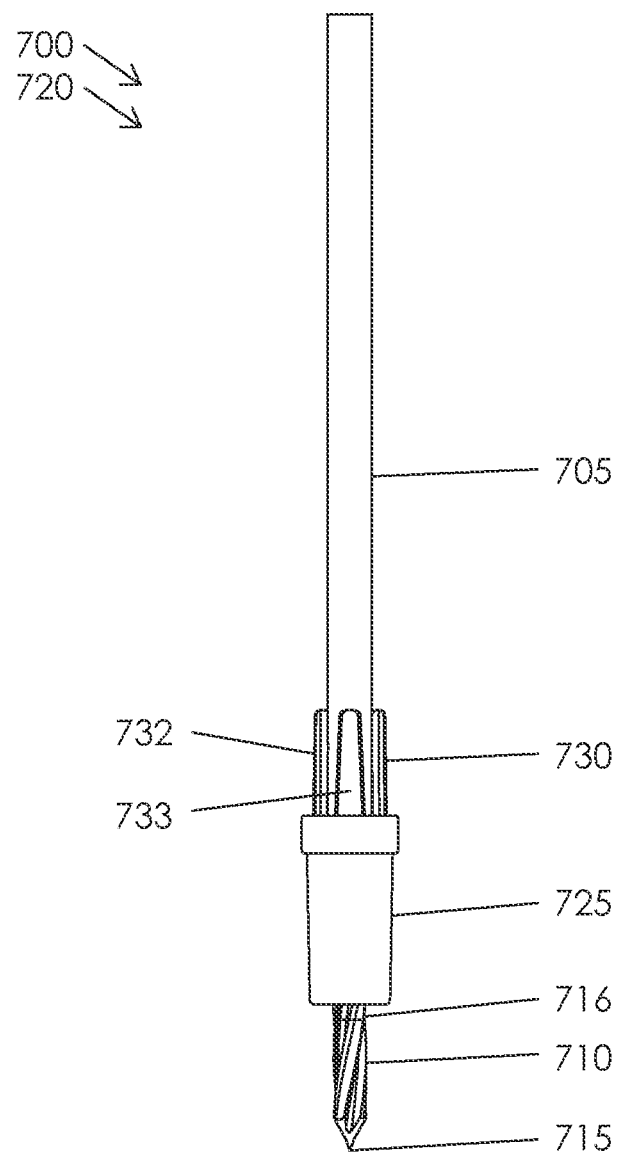
FIG. 31 is a side view illustrating the drill bit engaged with the drill bit stop.

FIG. 31 illustrates the drill bit 700 engaged with the drill bit stop 720. The drill bit stop hole 735 fits over the drill bit flutes 710 and a portion of the drill bit shank 705. The drill bit stop appendages 730-733 flex slightly as the drill bit stop 720 is placed on the drill bit 700, allowing for a frictional fit to prevent the drill bit stop 720 from sliding off prematurely. The drill bit stop body 725 now presents a hard stop surface when a surgeon begins to drill a hole in bone. In this embodiment, the drill bit stop body 725 limits the drilling depth to the location of the drill bit marker line 716.

Figure 32:
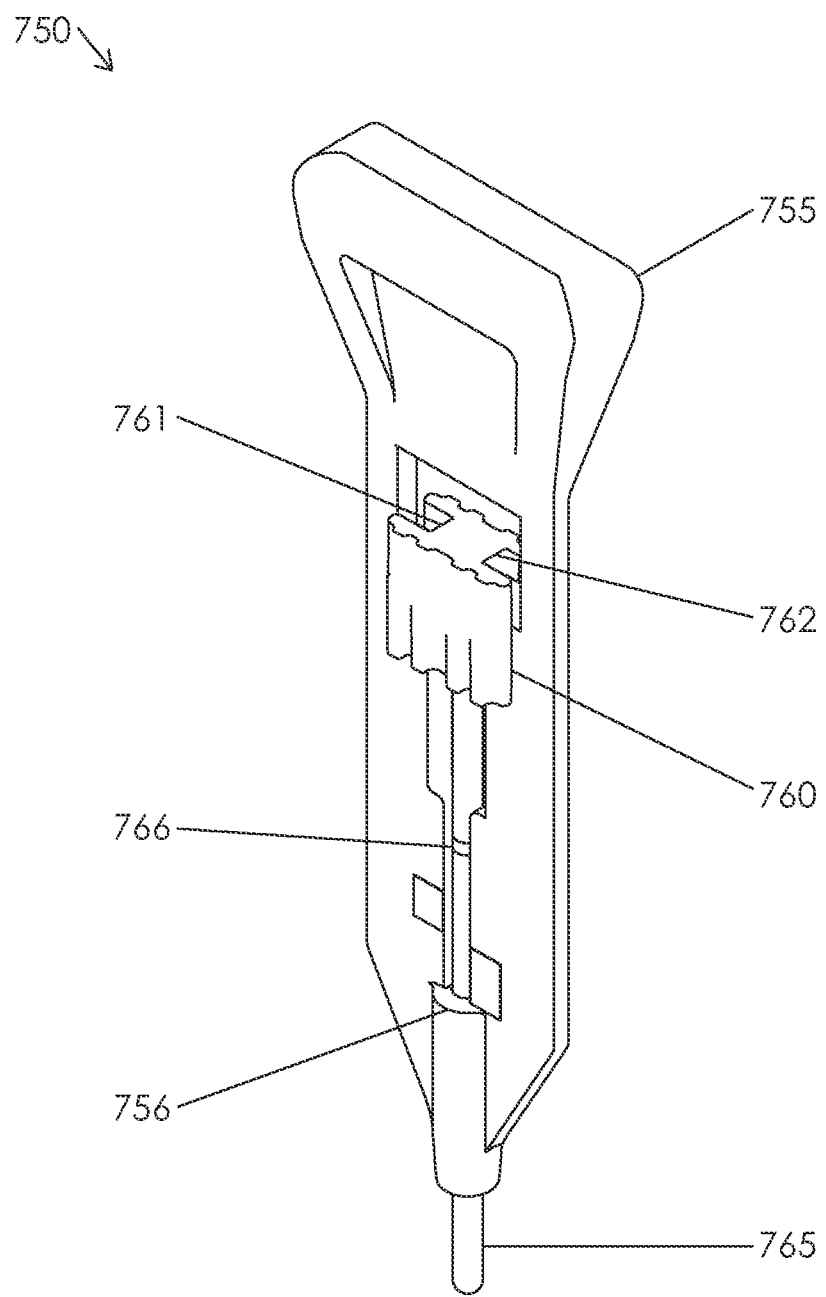
FIG. 32 is a perspective view illustrating a sizing tool used to select a proper implant.

FIG. 32 illustrates a sizing tool 750. The sizing tool 750 includes three parts: a sizing guide body 755, a sizing guide slider 760, and a sizing guide pin 765. The sizing guide body 755 can be made of plastic or metal, and is designed to be comfortable when used by a surgeon. The sizing guide body 755 includes a sizing guide hole 756, which is a through hole that will accommodate the diameter of the sizing guide pin 765. The sizing guide pin 765 can be made of metal or plastic, and includes a pin line 766 for marking the location of the pin. The sizing guide pin 765 slides freely through the sizing guide hole 756. The sizing guide pin 765 is free on one end and inserts into the sizing guide slider 760 on the other end. The sizing guide slider 760 fits within an aperture of the sizing guide body 755 and includes slots 761 and 762 that engage and slide along the sizing guide body 755. The sizing tool 750 is used as follows. The surgeon inserts the sizing guide pin 765 into a hole in a bone, while holding the sizing guide body 755. The surgeon then slides the sizing guide slider 762 to the location such that the sizing guide pin 765 reaches the bottom of the hole in the bone. The surgeon can then read the depth of the hole by using the pin line 766.

Figure 33:
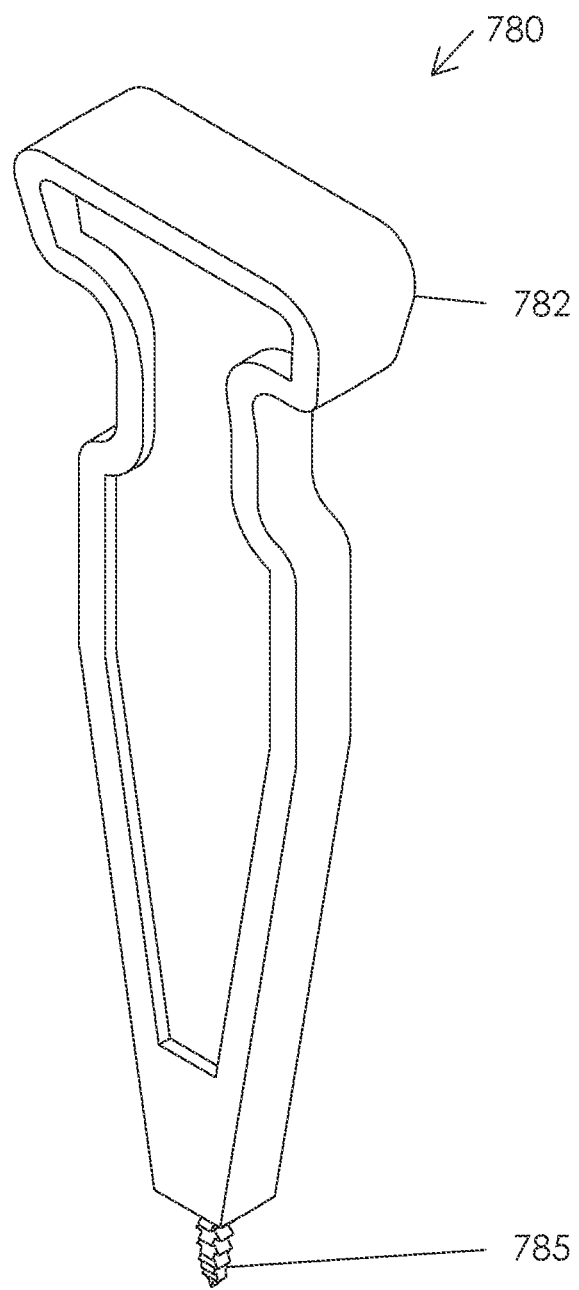
FIG. 33 is a perspective view illustrating a bone broach used to create a cavity in bone for an implant.

FIG. 33 illustrates a bone broach 780. The bone broach 780 includes a body 782, ergonomically shaped to fit in a surgeon's hand, and a cutting blade 785. The body 782 can be made of plastic or metal, or any suitable material. The cutting blade 785 can also be made of any material, but most likely from metal. The cutting blade 785 contains serrations and a tapered shape, such that inserting the cutting blade 785 into a hole in a bone results in pieces of bone being scraped. In this way, the bone broach 780 can shape a cavity in bone, which then receives an implant therein.

FIGS. 34-38 illustrate an implant inserter 800 according to a second embodiment. The implant inserter 800 moves between an open and a locked position and includes an inserter body 805 and an inserter slider 820. The inserter body 805 and the inserter slider 820 function together as an assembly to hold and insert an intramedullary implant, such as the implant 10. The inserter body 805 includes inserter arms 806 and 807, grasping projections 808 and 809, and implant engagement surfaces 814 and 815. The inserter slider 820 includes a slider hole 821 and a grasping surface 822. The slider hole 821 is configured for the grasping projections 808 and 809 to slide into the slider hole 821 such that the inserter arms 806 and 807 are held in an implant engagement position. In the second embodiment, the inserter slider 820 defines a slot at the grasping surface 822 that allows the inserter slider 820 to frictionally engage the inserter body 805 at the juncture of the inserter arms 806 and 807. It should be understood however that any number of attachment methods including grooves, channels, or sliding surfaces may be employed to slidably engage the inserter slider 820 with the inserter body 805.

Figure 34:
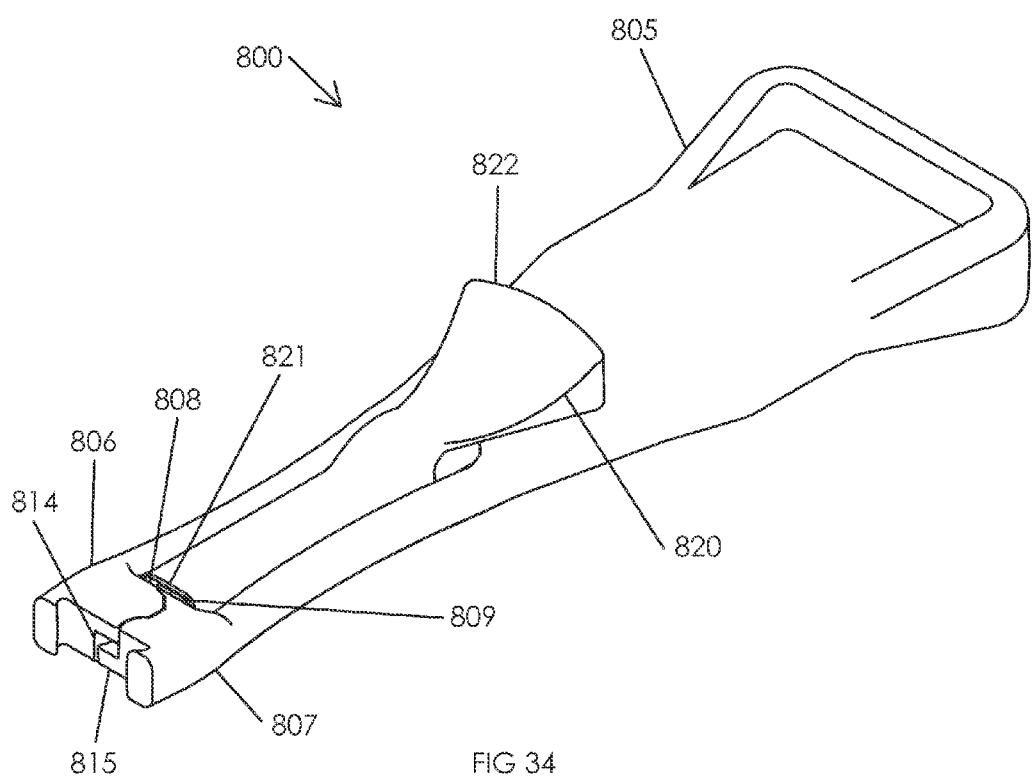
FIG. 34 is a perspective view illustrating an implant inserter according to a second embodiment of an implant insertion device with a slider in its implant engagement position.

FIG. 34 illustrates the implant inserter 800 in the locked position and the inserter arms 806 and 807 in the implant engagement position, although the implant 10 is not shown in this Figure for clarity. It can be seen that the slider hole 820 encompasses the grasping projections 808 and 809 to maintain the grasping projections 808 and 809 held together, which further keeps the inserter arms 806 and 807 in the implant engagement position. When the inserter arms 806 and 807 are held together, the implant engagement surfaces 814 and 815 are held together as well in a position suitable for engaging an implant.

Figure 35:
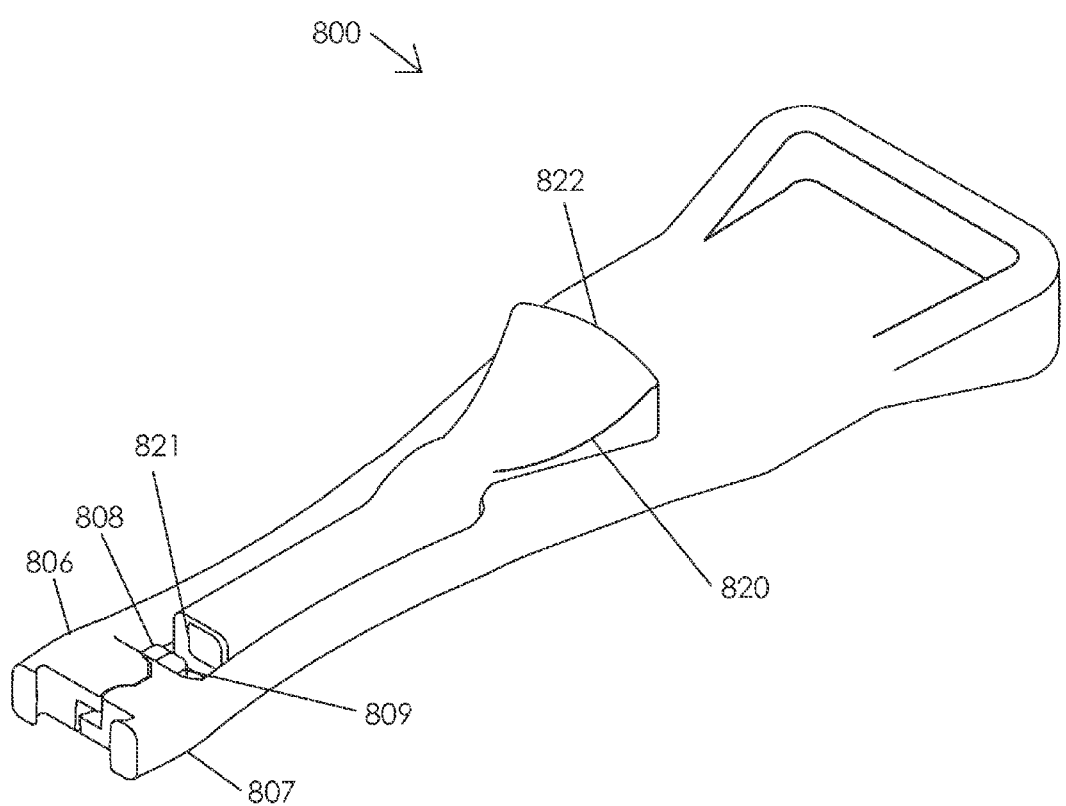
FIG. 35 is a perspective view illustrating the second embodiment of the implant inserter with the slider in its implant disengagement position.
Figure 36:
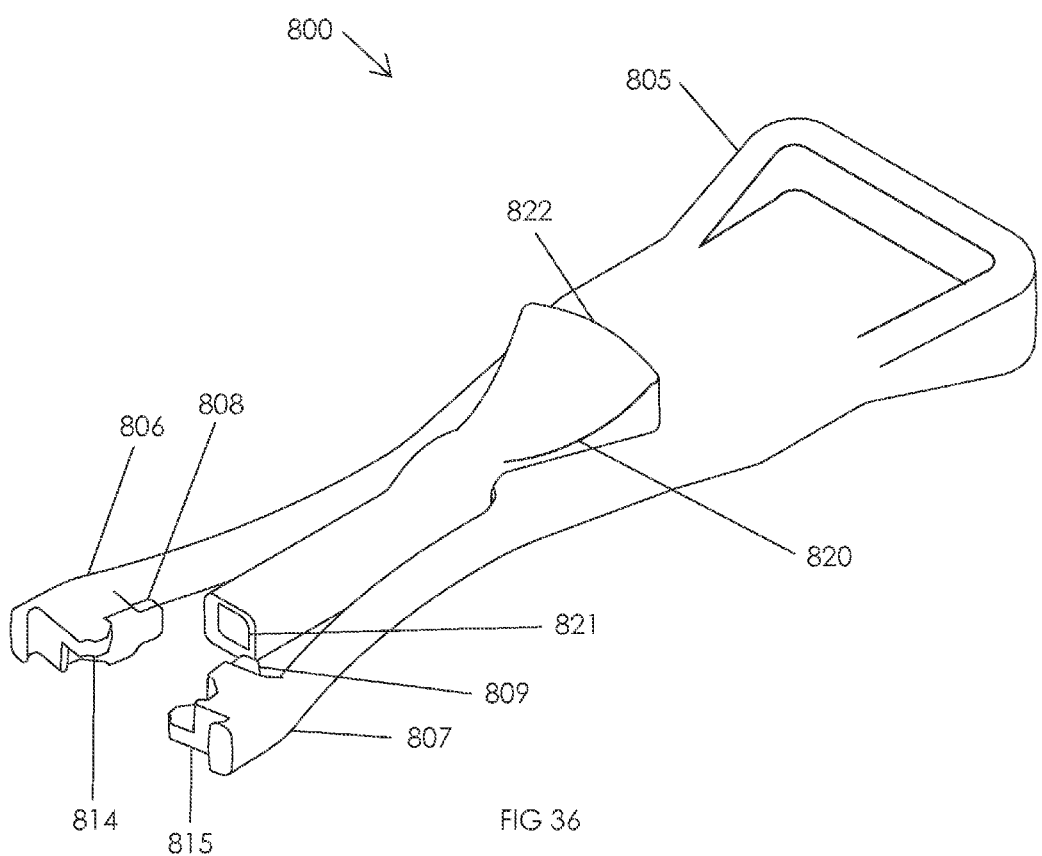
FIG. 36 is a perspective view illustrating the second embodiment of the implant inserter with the slider in its implant disengagement position and arms of the implant inserter in their implant disengagement position.
Figure 37:
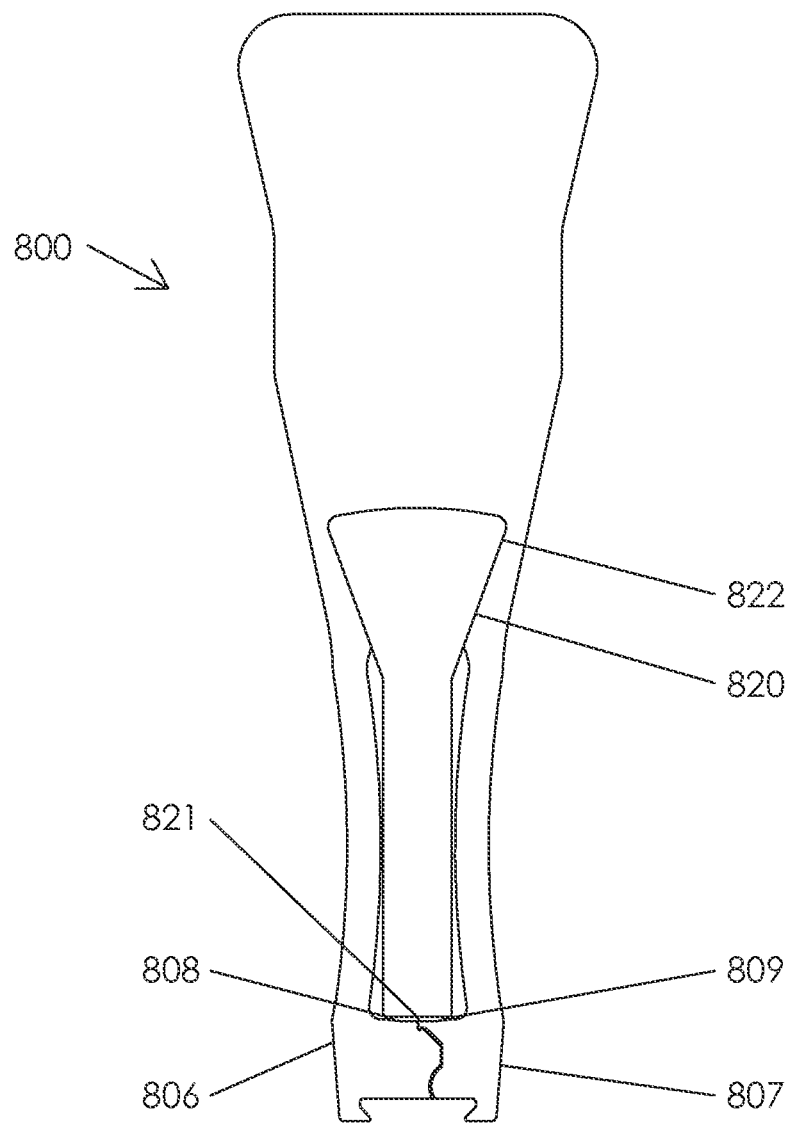
FIG. 37 is a front view illustrating the second embodiment of the implant inserter with the slider in its implant engagement position.
Figure 38:
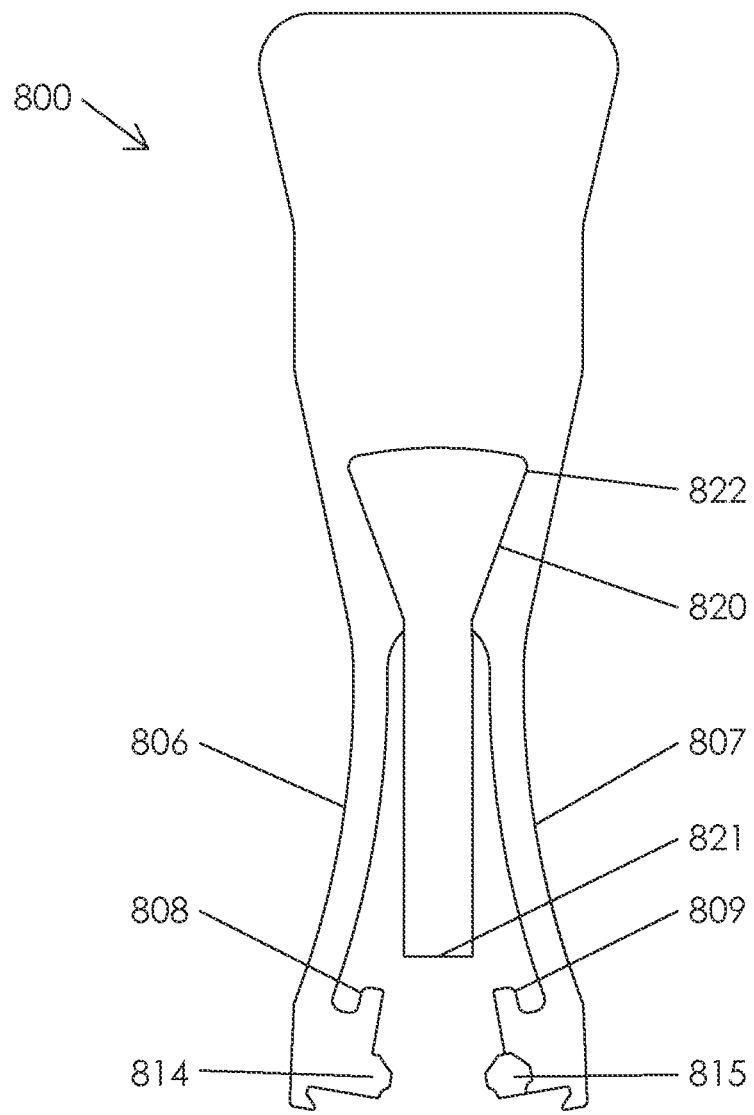
FIG. 38 is a front view illustrating the second embodiment of the implant inserter with the slider in its implant disengagement position and the arms of the implant inserter in their splayed position.

FIG. 35 illustrates the implant inserter 800 in the open position and the inserter arms 806 and 807 in a normally splayed position. Moving the implant inserter 800 to the open position withdraws the grasping surface 822 on the inserter slider 820 away from the grasping projections 808 and 809. As the slider hole 821 withdraws from the grasping projections 808 and 809, the grasping projections 808 and 809 are free to separate as illustrated in FIG. 36. It should be understood by one of ordinary skill in the art that the inserter arms 806 and 807 according to the second embodiment are molded in the normally splayed position such that as soon as the slider hole 821 is withdrawn and disengaged from the grasping projections 808 and 809, the inserter arms 806 and 807 are free to move to their normally splayed position. The implant engagement surfaces 814 and 815 are separated as well, although no implant is yet shown in these Figures. FIGS. 37 and 38 depict top views of the implant inserter 800 and its function according to the second embodiment.

Figure 39:
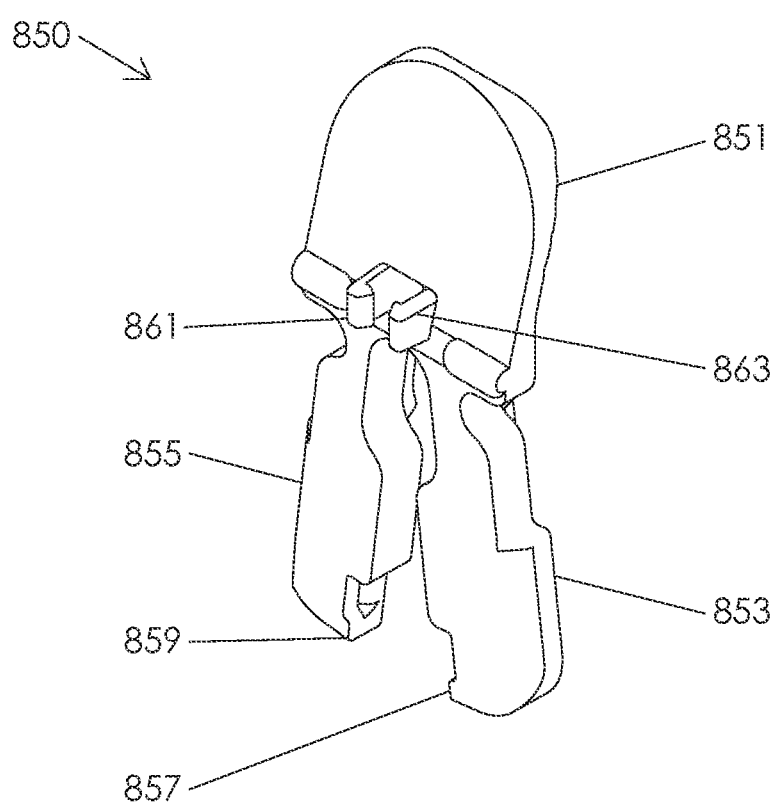
FIG. 39 is a perspective view illustrating an implant tab back piece with tab legs in their splayed position.

FIG. 39 illustrates an implant tab back 850. The implant tab back 850 is made of metal or plastic, and consists of a tab surface 851, tab projections 861 and 863, tab legs 853 and 855, and tab engagement surfaces 857 and 859. The tab legs 853 and 855 are moveable between a normally open position and a closed position.

Figure 40:
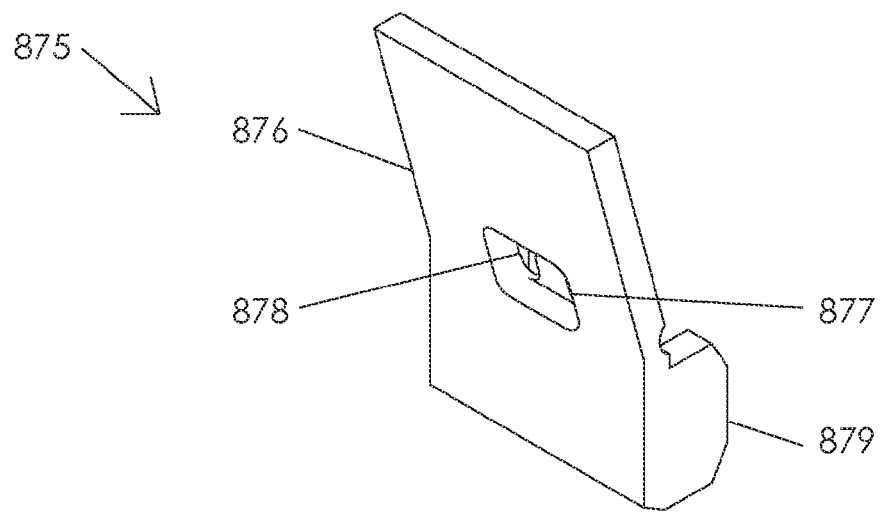
FIG. 40 is a front perspective view illustrating an implant tab front piece.
Figure 41:
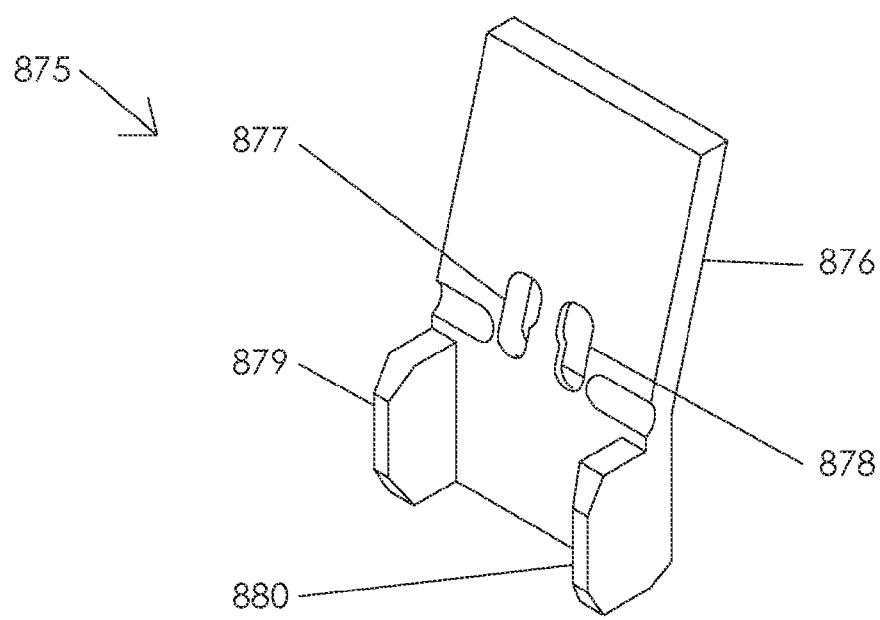
FIG. 41 is a rear perspective view illustrating the implant tab front piece.
Figure 42:
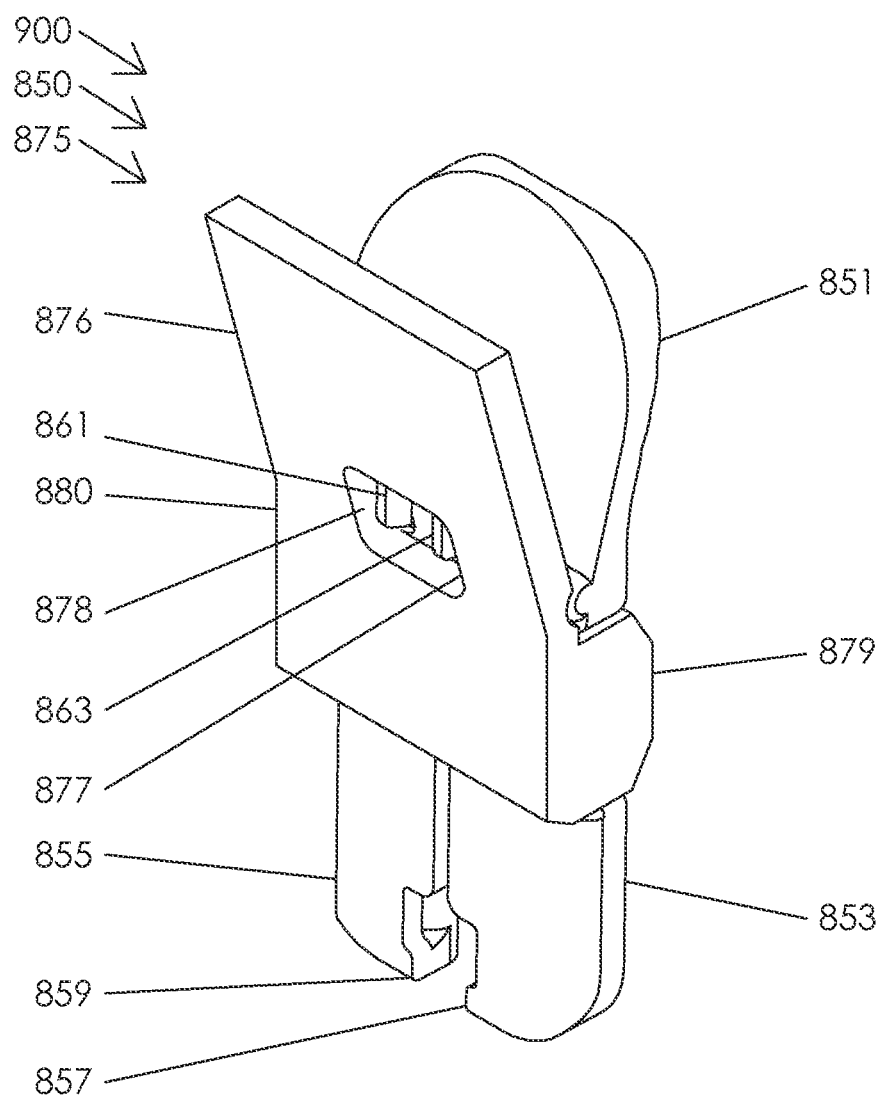
FIG. 42 is a perspective view illustrating an implant tab with tab legs in their implant engagement position.
Figure 43:
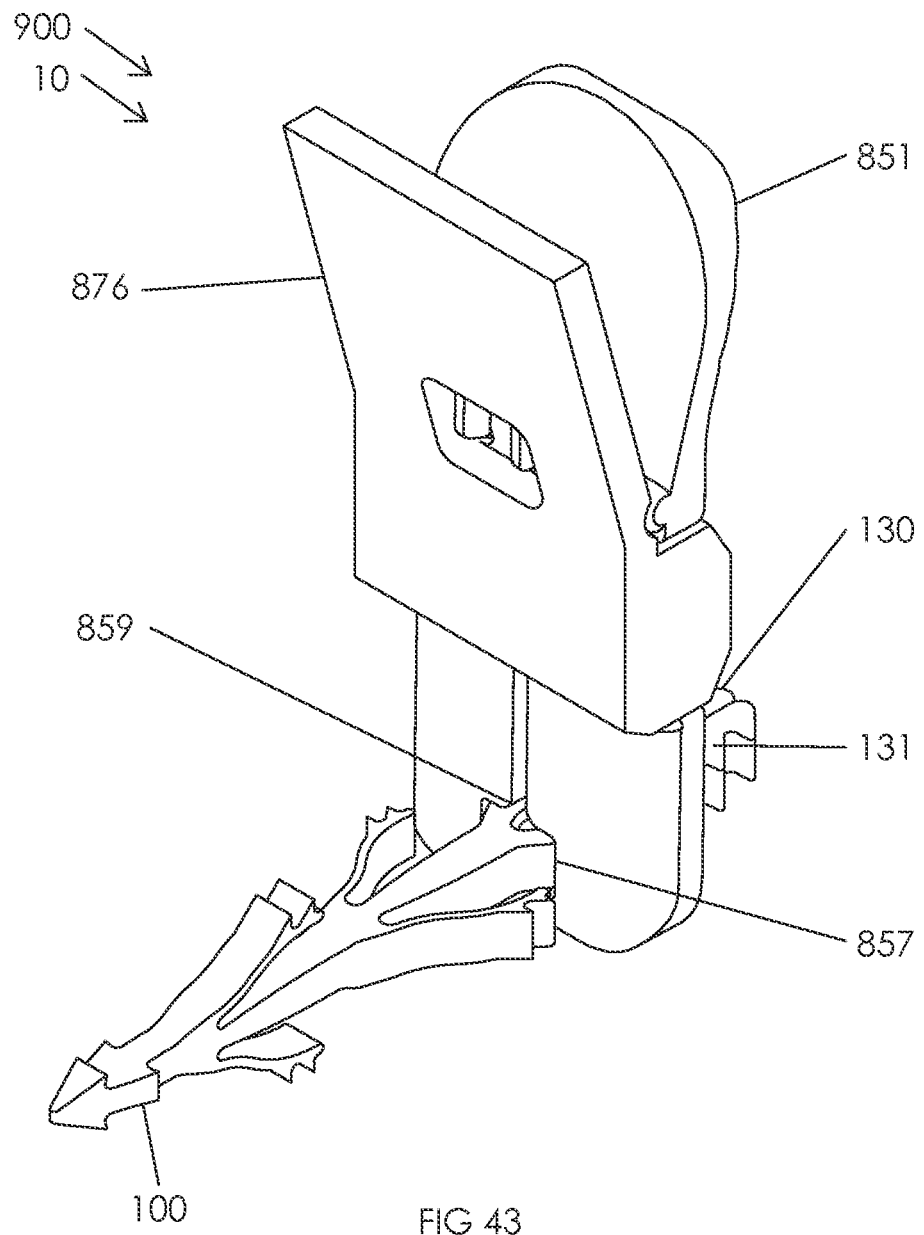
FIG. 43 is a perspective view illustrating the implant tab with the tab legs engaging the legs of an implant.
Figure 44:
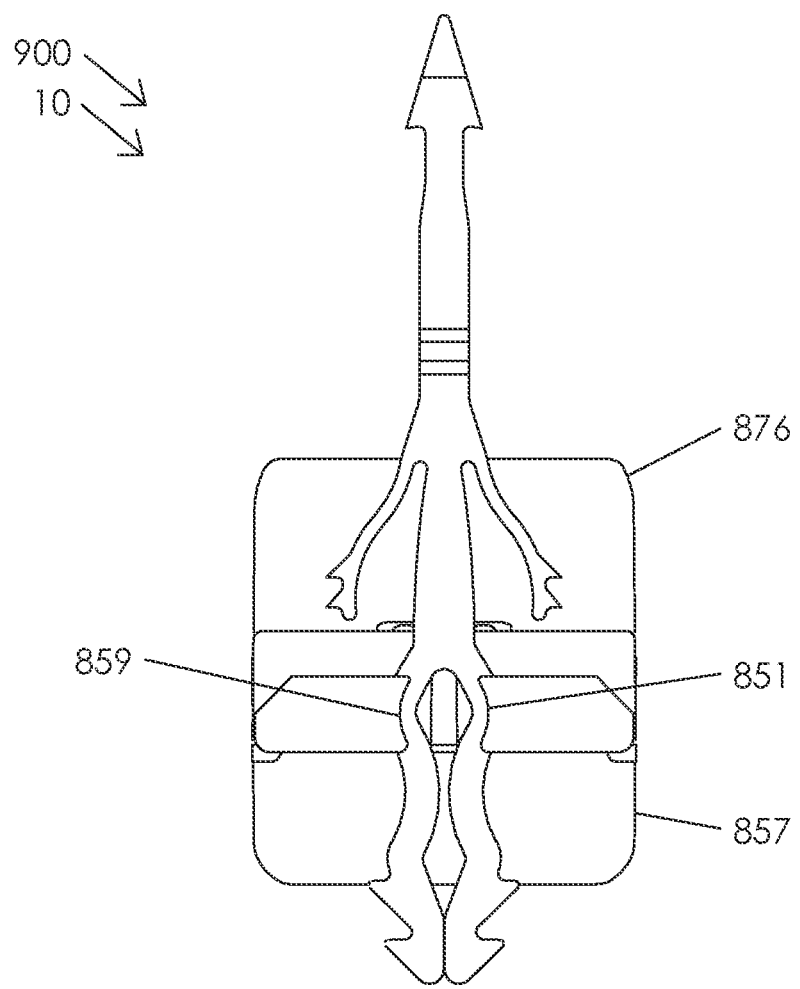
FIG. 44 is a bottom view illustrating the implant tab with tab legs engaging the legs of the implant.

FIGS. 40 and 41 illustrate an implant tab front or lock 875. This component can also be made of plastic or metal. The implant tab front or lock 875 includes a tab surface 876, tab slots 877 and 878 which are sized to receive the tab projections 861 and 863, and tab constraining flaps 879 and 880.

The functioning of an implant tab 900 which is formed through the engagement of the implant tab front 875 with the implant tab back 850 is illustrated in FIGS. 42 and 69-71. To form the implant tab 900, the implant tab front 875 mounts to the implant tab back 850. Upon mounting the implant tab front 875 to the implant tab back 850, the implant tab front 875 is movable between a disengaged and a engaged position. Moving the implant tab front 875 between the disengaged and the engaged position transitions the implant tab 900 between an unlocked and locked position. The tab projections 861 and 863 insert into the tab slots 877 and 878 to hold the implant tab front 875 in place against the implant tab back 850. Once the implant tab front 875 resides against the implant tab back 850, the implant tab front 875 will be in its engaged position and the implant tab 900 will be in its locked position. In the locked position, the tab constraining flaps 879 and 880 grasp around the tab legs 853 and 855, holding the tab legs 853 and 855 in the closed position. In the closed position, the tab engagement surfaces 857 and 859 are close together such that the implant 10 fits between and is held in place by the tab legs 853 and 855. It is also noted that if a user squeezes or pinches the tab surfaces 851 and 876 towards each other, then the implant tab front 875 will move to its disengaged position. Moving the implant tab front 875 to its disengaged position, allows transition of the implant tab 900 to its unlocked position. As the implant tab 900 transitions to its unlocked position, the constraining flaps 879 and 880 release the tab legs 853 and 855 which travel to their normal open position, thus allowing the tab engagement surfaces 857 and 859 to separate.

FIGS. 43-44 and 69-71 illustrate the functioning of the implant tab 900. The tab legs 853 and 855 surround a portion of the legs 130 and 131 of the implant 10. With the implant tab front 875 in position, the tab legs 853 and 855, and hence the tab engagement surfaces 857 and 859 are held together to constrain the legs 130 and 131 of the implant 10.

Figure 45:
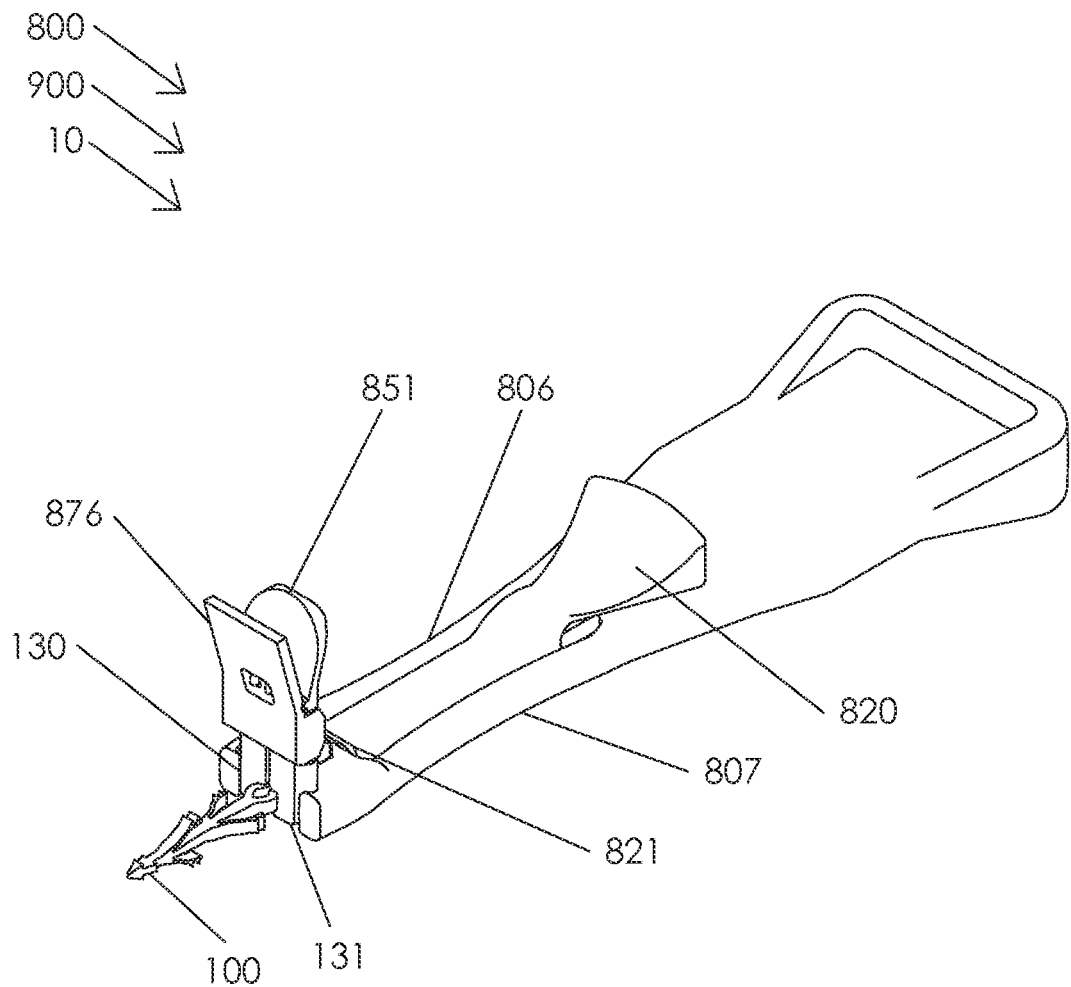
FIG. 45 is a perspective view illustrating the implant being held by the implant tab and further being constrained by the second embodiment of the implant inserter with its slider in its implant engagement position.
Figure 46:
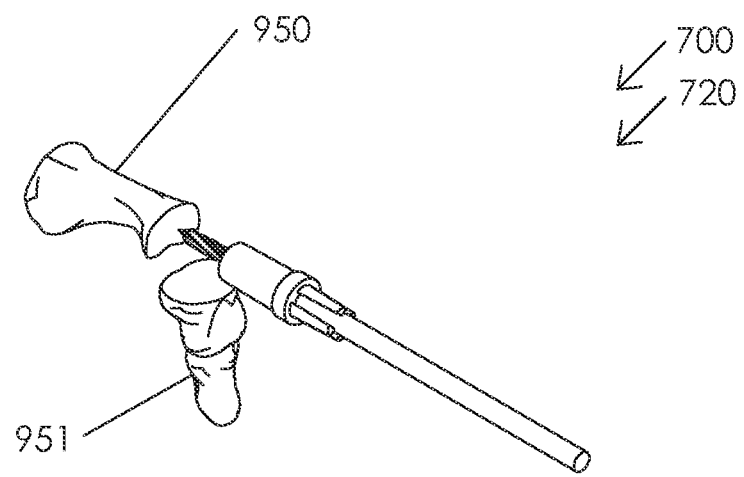
FIG. 46 is a perspective view illustrating the drill bit engaged with the drill bit stop and being used to drill a hole in a first bone.
Figure 47:
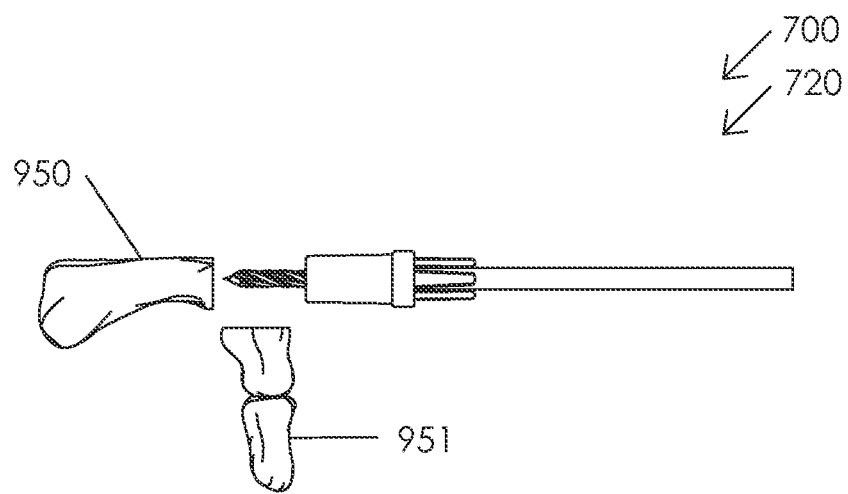
FIG. 47 is a side view illustrating the drill bit engaged with the drill bit stop and being used to drill a hole in a first bone.
Figure 48:
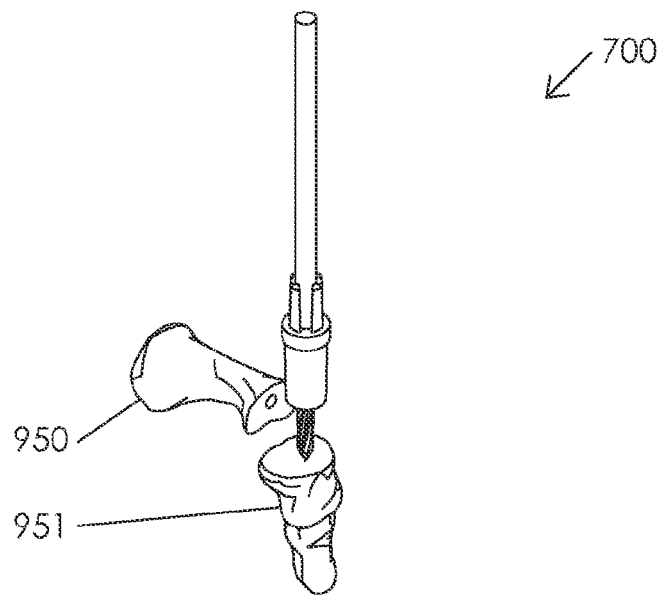
FIG. 48 is a perspective view illustrating the drill bit engaged with the drill bit stop being used to drill a hole in a second bone.
Figure 49:
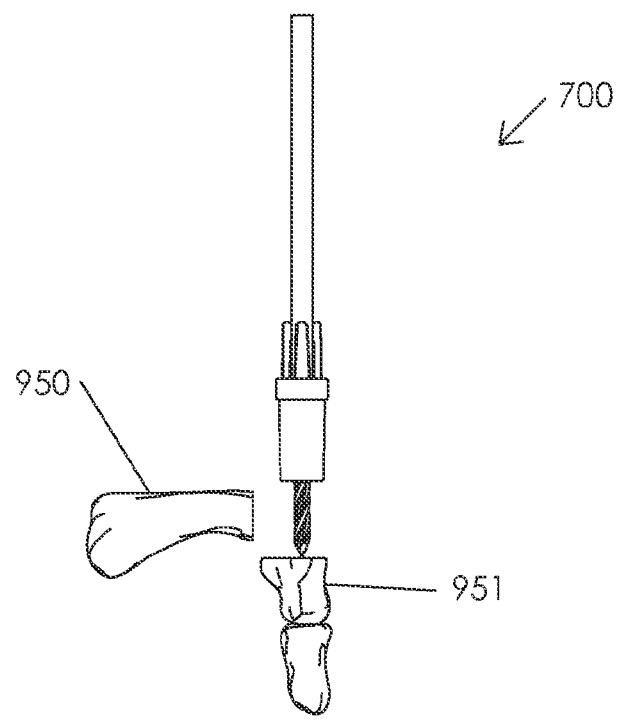
FIG. 49 is a side view illustrating the drill bit engaged with the drill bit stop and being used to drill a hole in a second bone.

FIG. 45 illustrates the full utility of the implant inserter 800 and the implant tab 900 in engaging the implant 10. The legs 130 and 131 of the implant 10 are held together and constrained by the implant tab 900. The implant tab 900 is positioned at the ends of the inserter arms 806 and 807 of implant inserter 800. The inserter arms 806 and 807 are moved to their implant engagement position whereby the end of each inserter arm 806 and 807 grasps a respective tab leg 853 and 855 to maintain the implant tab 900 engaged with the implant inserter 800. When the implant tab 900 is engaged with the implant inserter 800, the implant engagement surfaces 814 and 815 encompass and engage the ends of the legs 130 and 131 of the implant 10 to assist in maintaining the legs 130 in their insertion shape. The inserter slider 820 moves forward such that the slider hole 821 maintains contact with the grasping projections 808 and 809. With the slider hole 821 engaged with the grasping projections 808 and 809, the inserter arms 806 and 807 remain constrained in their implant engagement position. In this configuration, the inserter 800 is in the locked position and the implant 10 is ready for insertion into a bone.

FIGS. 46-49 illustrate a method for drilling holes in two bones 950 and 951 to pre-determined depths. The drill bit 700 is equipped with the drill bit stop 720, and positioned such that the drill bit tip 715 penetrates a bone in the proper location. The drill bit stop 720 limits the depth to a desired maximum. The drill bit 700 can now drill into the bones 950 or 951 to a maximum depth, or any depth short of the maximum.

Figure 50:
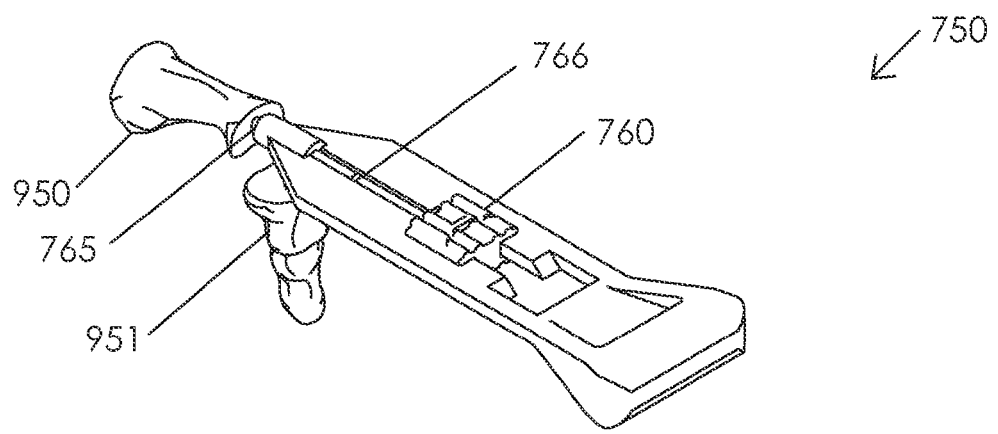
FIG. 50 is a perspective view illustrating the sizing tool being used to measure the depth of the hole in the first bone.
Figure 51:
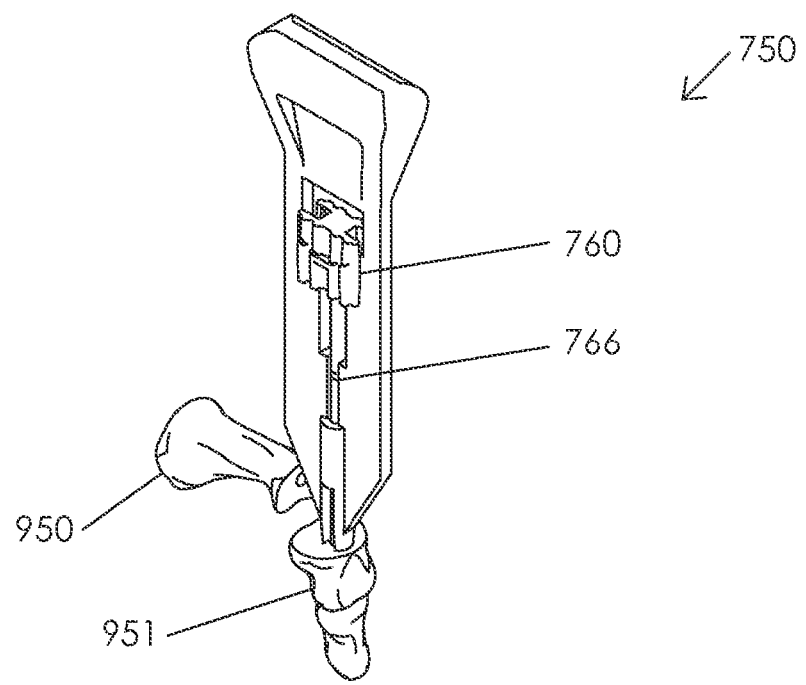
FIG. 51 is a perspective view illustrating the sizing tool being used to measure the depth of the hole in the second bone.

FIGS. 50-51 illustrate a method of determining the size of an implant that will fit in a bone. The sizing tool 750 is positioned such that the slider pin 765 extends into a hole in the bone 950 or 951. The sizing tool slider 760 can be positioned to reach the maximum depth of the hole, and then the depth of the hole becomes evident such that a surgeon selects an implant that fits in the hole without being too large or too small.

Figure 52:
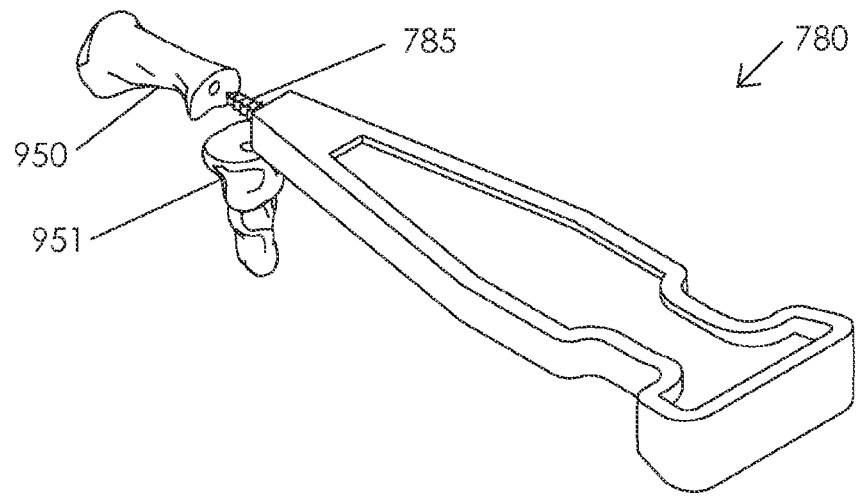
FIG. 52 is a perspective view illustrating the bone broach being used to create a cavity in the first bone.
Figure 53:
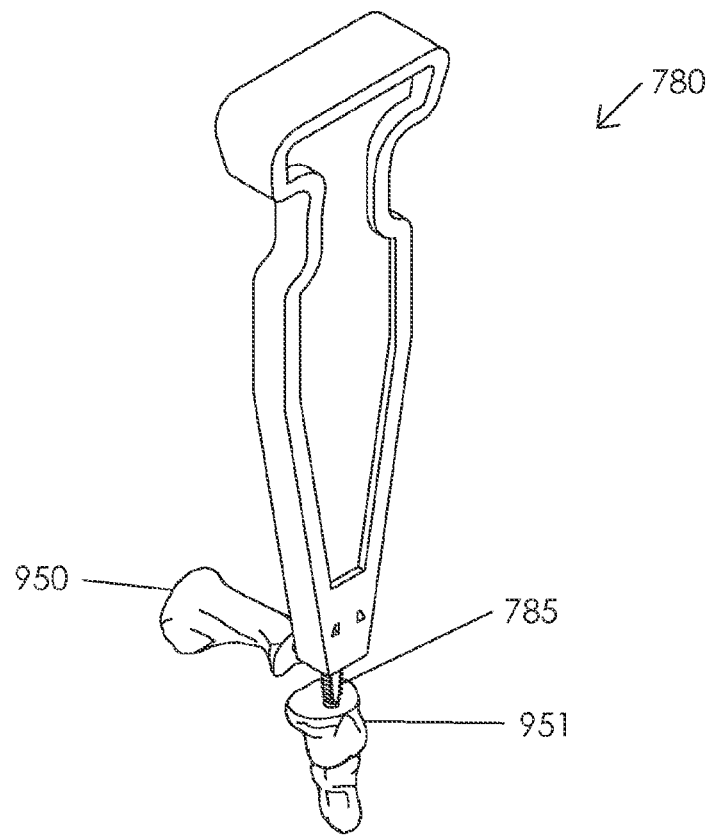
FIG. 53 is a perspective view illustrating the bone broach being used to create a cavity in the second bone.

FIGS. 52-53 illustrate a method for shaping a cavity to receive an implant using the broach 780. In these Figures, the bones 950 and 951 have holes already drilled by the drill bit 700. The cutting blade 785 inserts into each hole and shaves and chips away bone as broach 780 is manipulated by the surgeon.

Figure 54:
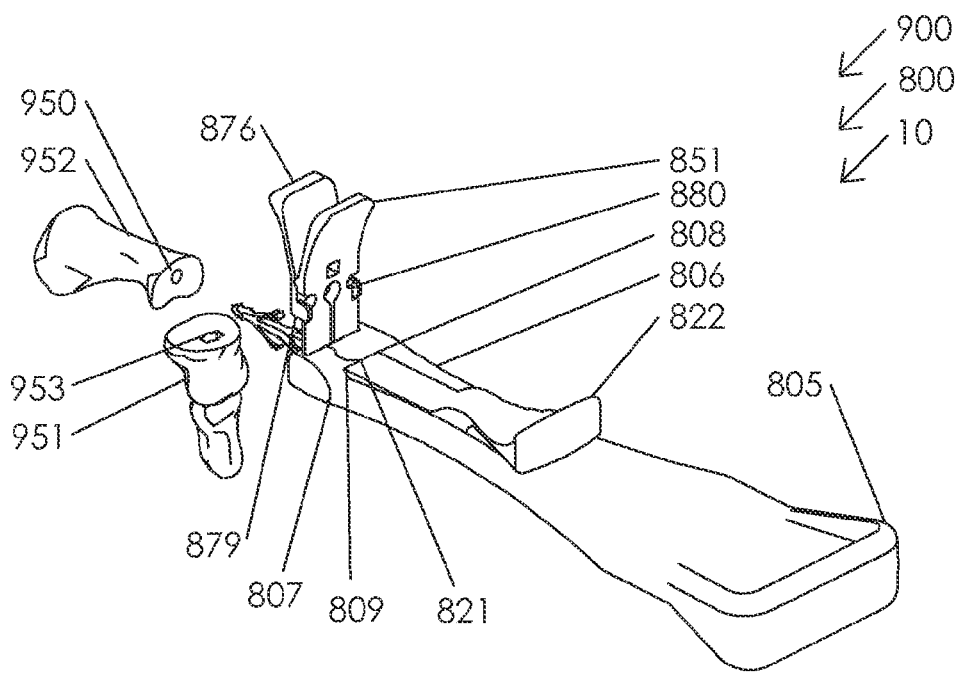
FIG. 54 is a perspective view illustrating the implant inserter and the implant tab being used to insert an implant into a first bone.
Figure 55:
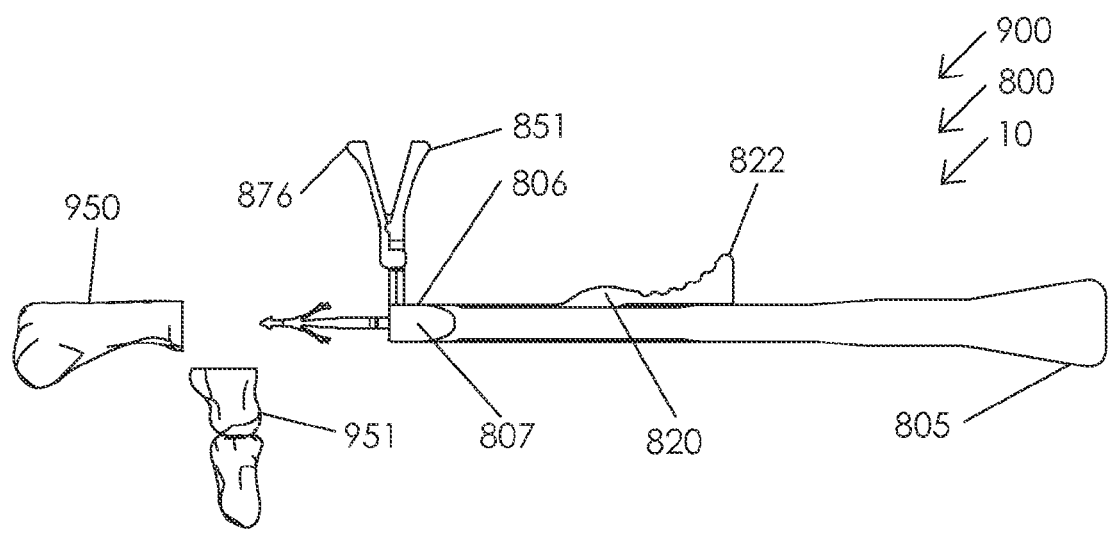
FIG. 55 is a side view illustrating the implant inserter and the implant tab being used to insert the implant into the first bone.

FIGS. 54-55 illustrate a method for inserting an intramedullary implant 10 into the bones 950 and 951. In FIGS. 54-55, the implant 10 is firmly held by the implant inserter 800 and the implant tab 900. The implant 10 is not yet inserted into bone. It can be seen that the constraining forces of the implant inserter 800 and the implant tab 900 maintain the legs 130 and 131 of the implant 10 in the closed position.

Figure 56:
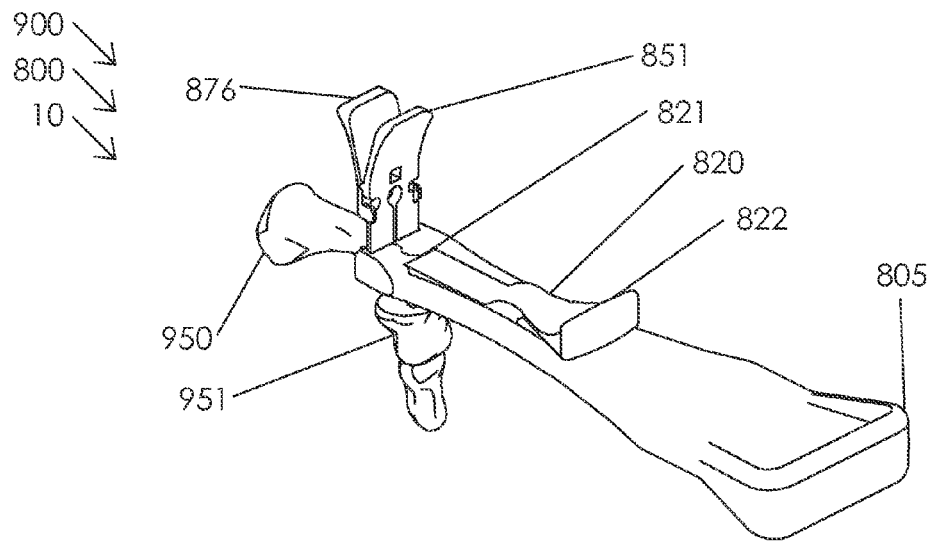
FIG. 56 is a perspective view illustrating the implant inserter and the implant tab after the implant has been inserted into the first bone.
Figure 57:
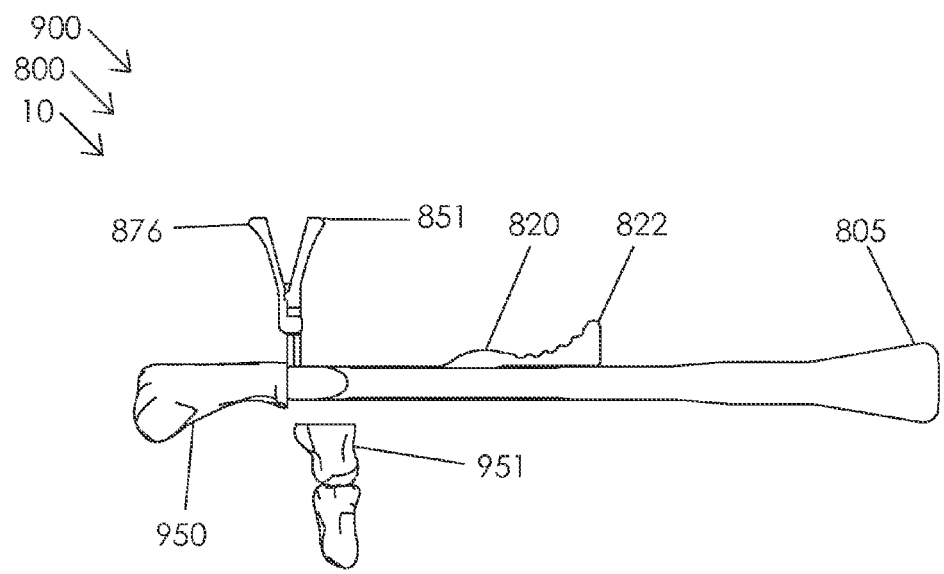
FIG. 57 is a side view illustrating the implant inserter and the implant tab after the implant has been inserted into the first bone.

Now, in FIGS. 56-57, the surgeon has used the implant inserter 800 to push the first and second body sections 150 and 151 of the implant 10 into the bone 950. The inserter slider 820 is still in the forward position, and as the surgeon pushes on the implant inserter 800, forward pressure on the inserter slider 820 is maintained, thus keep the implant 10 firmly engaged.

Figure 58:
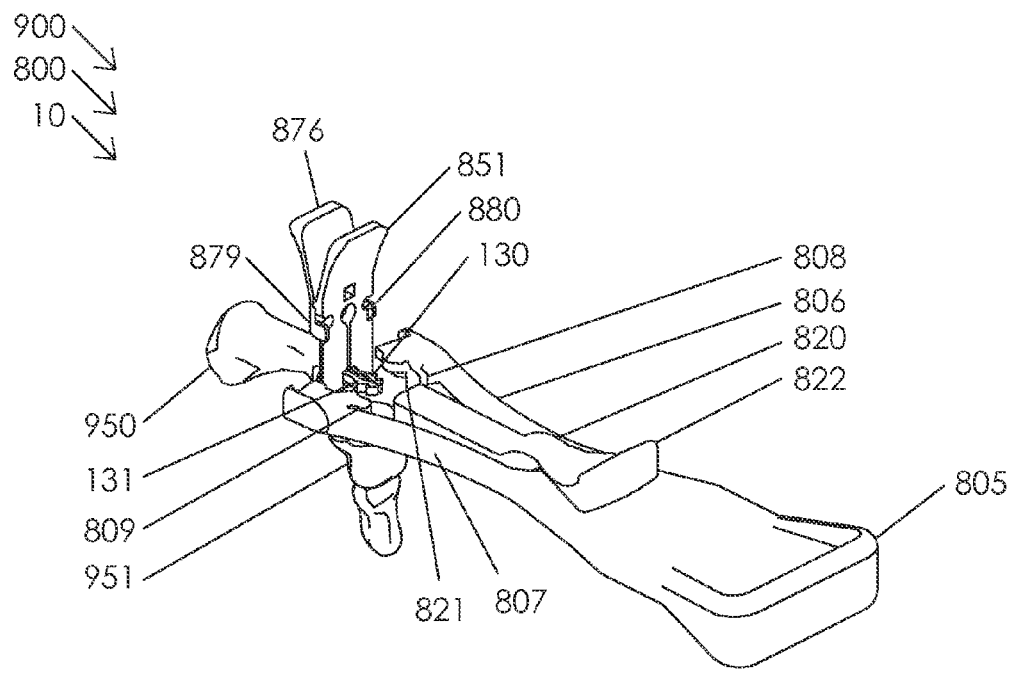
FIG. 58 is a perspective view illustrating the implant inserter being removed from the implant tab after the implant has been inserted into the first bone.
Figure 59:
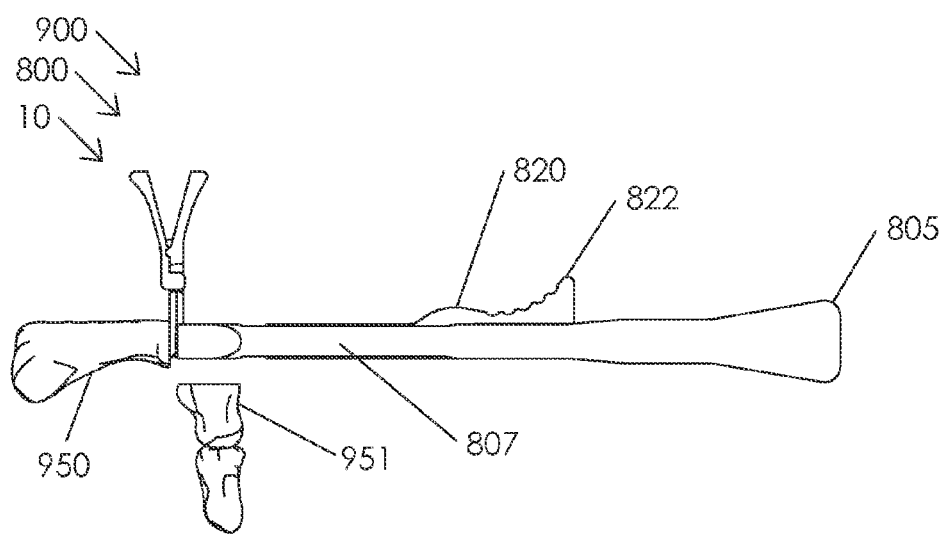
FIG. 59 is a side view illustrating the implant inserter being removed from the implant tab after the implant has been inserted into the first bone.

FIGS. 58-59 illustrate what happens when the surgeon retracts the inserter slider 820. The slider hole 821 retracts from the projections 808 and 809, freeing them along with the inserter arms 806 and 807, which move to their normal splayed open position. In this way, the implant inserter 800 can be easily disengaged and removed from the implant tab 900 and the legs 130 and 131 of the implant 10, thereby exposing the legs 130 and 131 of implant 10.

Figure 60:
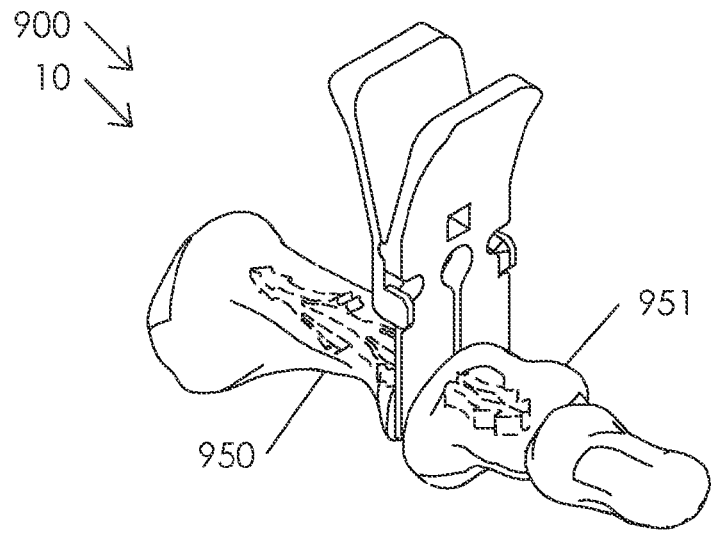
FIG. 60 is a perspective view illustrating the implant inserted into the first bone and a second bone with the implant tab still constraining the legs of the implant.
Figure 61:
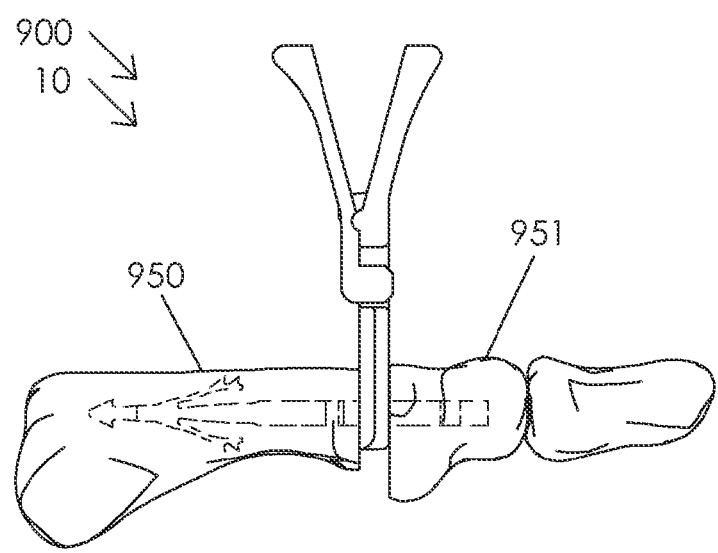
FIG. 61 is a side view illustrating the implant inserted into the first bone and a second bone with the implant tab still constraining the legs of the implant.

FIGS. 60 and 61 illustrate the bone 951 pulled over the legs 130 and 131 of the implant 10. The implant tab 900 is still in place, constraining the legs 130 and 131 of the implant 10 to allow for easy insertion into the bone 951.

Figure 62:
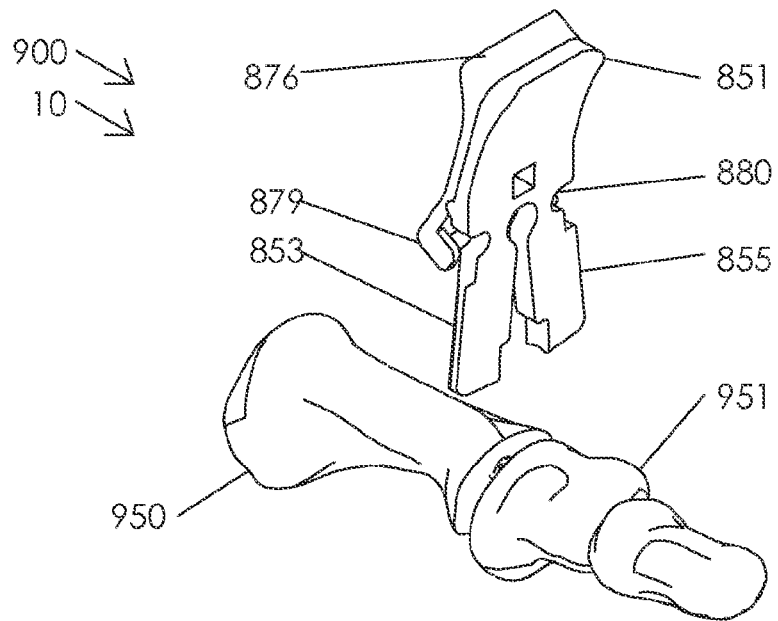
FIG. 62 is a perspective view illustrating the disengagement of the implant tab from the implant once the implant is inserted into the first bone and the second bone.
Figure 63:
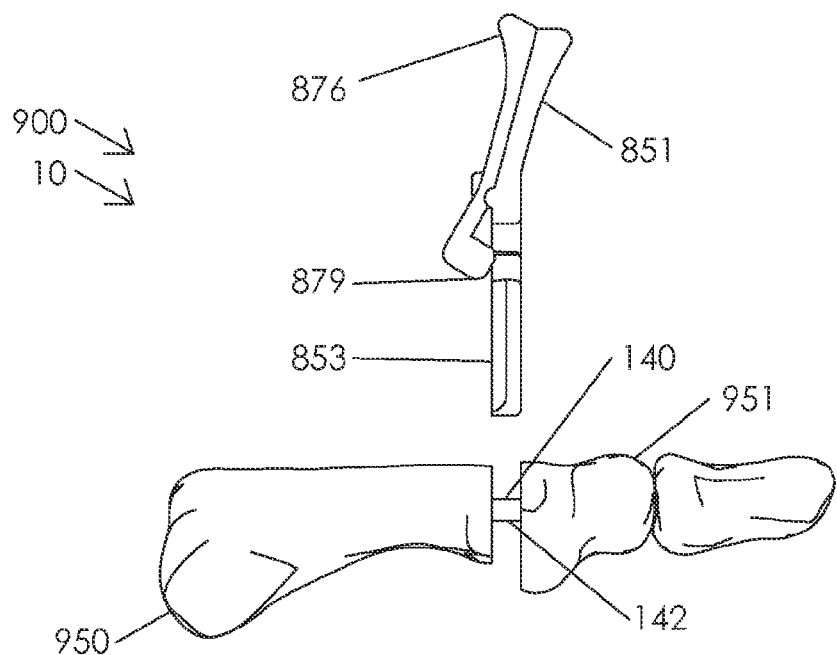
FIG. 63 is a side view illustrating the disengagement of the implant tab from the implant once the implant is inserted into the first bone and the second bone.

FIGS. 62 and 63 illustrate the final steps in inserting the implant 10 into the bones 950 and 951. The tab surfaces 851 and 876 are squeezed, causing the tab constraining flaps 879 and 880 to release the tab legs 853 and 855. Without constraint, the tab legs 853 and 855 spring to their open and normal shape, allowing the implant tab 900 to be removed from the implant 10. At this time, the implant legs 130 and 131 are now able to move freely to engage the interior of the bone 951. The bone 951 can now be pressed forward to mate against the bone 950 with the implant 10 now spanning in between the two bones 950 and 951 as illustrated in FIGS. 26-28. The implant 10 lies between the bones 950 and 951, thereby fixating the two bones 950 and 951.

Figure 65:
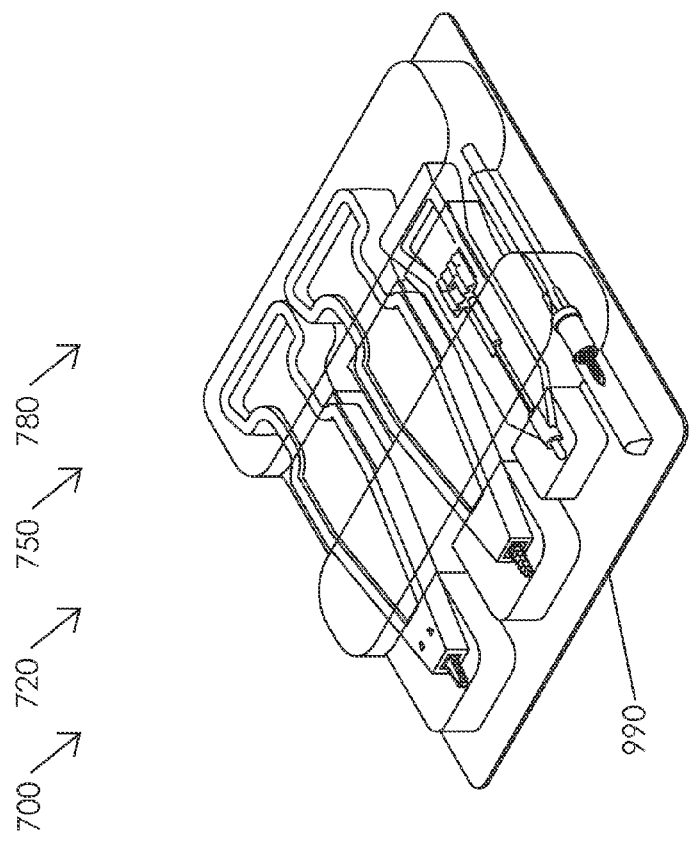
FIG. 65 is a perspective view illustrating an instrument tray containing a drill bit, a drill bit stop, two bone broaches, and a sizing tool.
Figure 64:
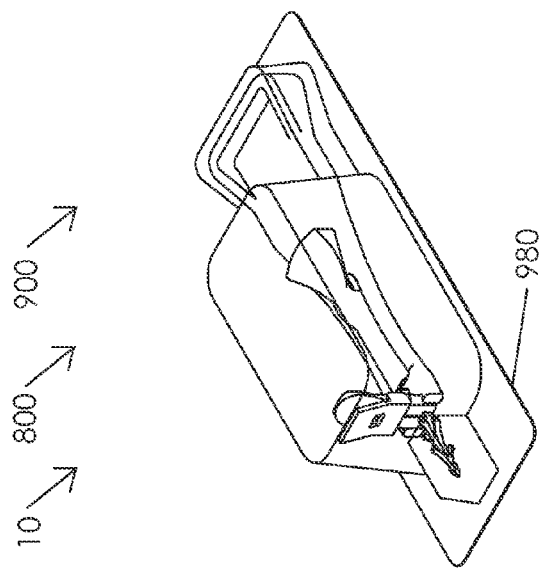
FIG. 64 is a perspective view illustrating an implant tray containing an implant inserter, an implant, and an implant tab.
Figure 66:
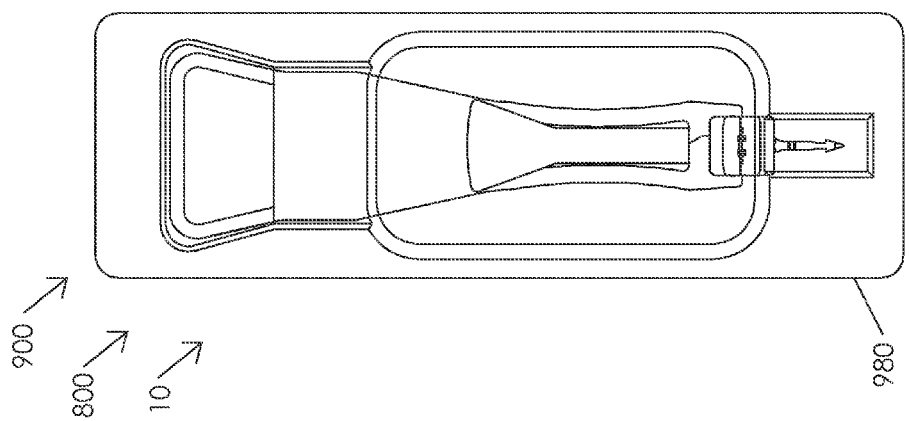
FIG. 66 is a top view illustrating an implant tray containing an implant inserter, an implant, and an implant tab.

FIGS. 64-66 illustrate an arrangement for packaging the implant 10, preloaded onto the implant inserter 800 with the implant tab 900 in place. The implant tray 980 is configured to hold these components.

Figure 67:
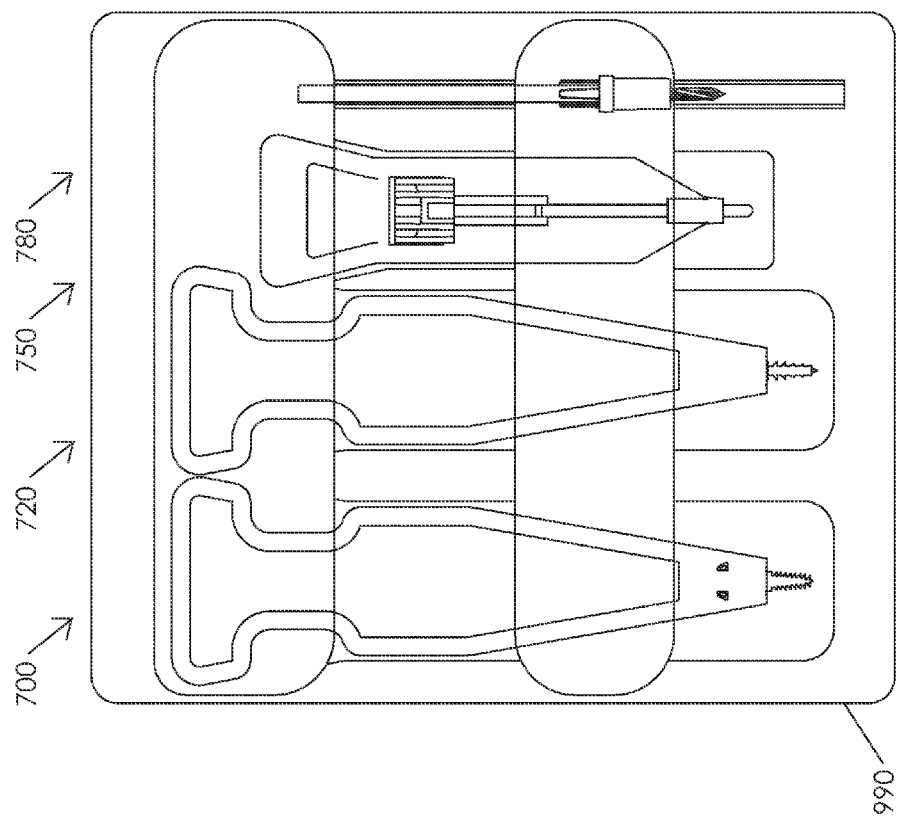
FIG. 67 is a top view illustrating an instrument tray containing a drill bit, a drill bit stop, two bone broaches, and a sizing tool.

FIGS. 65-67 illustrate packaging for instruments needed to use the implant 10. In these Figures, an instrument tray 990 is configured to hold the drill bit 700 without or preloaded with the drill bit stop 720, the sizing tool 750, and one or more broaches 780. In this configuration, two broaches 780 are shown, so that the surgeon has a selection of how to size holes in bone.

A system now consists of one or more implant trays 980, with a single instrument tray 990. In this way, a surgeon using multiple implants on the same patient does not have to waste instruments unnecessarily.

It should be understood that the pre-loading and packaging of the implant inserter 800 with the implant tab 900 in place with the implant 10 allows for sterilizing of the implant inserter 800 with the implant tab 900 in place and the implant 10 by any common sterilization method such as gas, radiation, or another type as well as delivery of the implant insertion device 10 and the implant 10 in sterile condition. The packaged instruments may be sterilized similarly.

While the implant inserter 800 and the implant tab 900 may be manually loaded with the implant 10, a method incorporating mechanical assistance improves the loading process. FIGS. 68-85 illustrate a method of loading the implant inserter 800 with implant tab 900 and the implant 10 incorporating mechanical assistance. The method includes first loading the implant tab 900 with the implant 10, and then loading the implant inserter 800 with the implant tab 900 and the secured implant 10.

FIGS. 68-77 illustrate a method of loading the implant tab 900 with the implant 10. The method includes an implant tab press tool 1100 to couple the implant 10 with the implant tab 900. Each method step at any given time normally involves multiple implants 10 and multiple implant tabs 900, however, for the sake of disclosure and in order to aid in the understanding of the present invention, the method described herein will included only one implant 10 and one implant tab 900.

Figure 68:
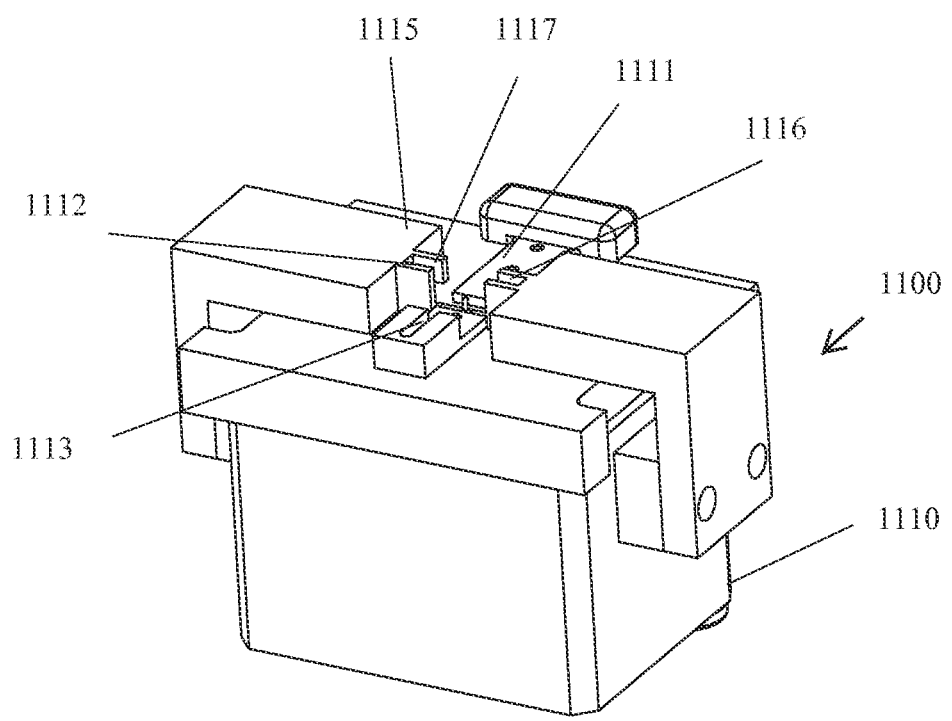
FIG. 68 is a perspective view illustrating an implant tab press tool.

FIG. 68 illustrates the implant tab press tool 1100 that includes a press tool base 1110 and a vice 1115. The press tool base 1110 defines a loading surface 1111 including a tab retention slot 1112 and an implant retention slot 1113. The vice 1115 defines press faces 1116 and 1117. The implant tab press tool 1100 in the present method is a pneumatic press; however, one of ordinary skill in the art will recognize that any form of press tool may be implemented.

Figure 69:
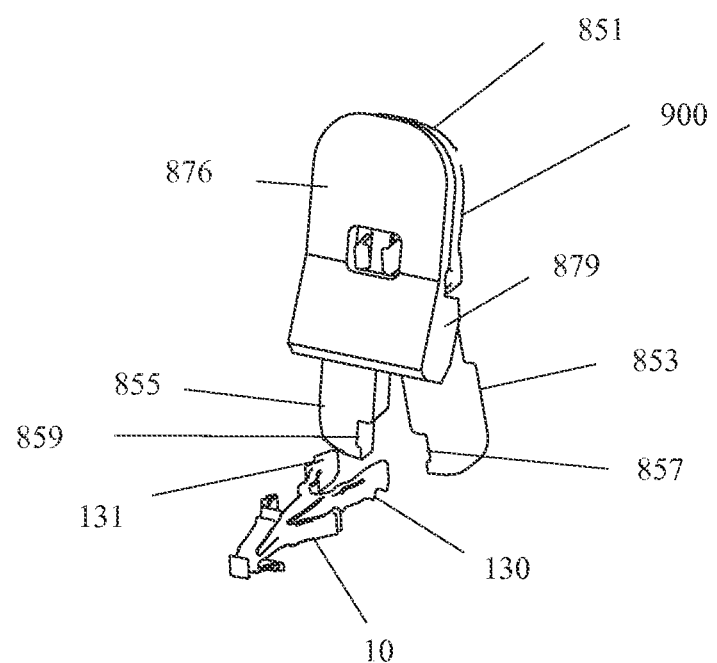
FIG. 69 is a perspective view illustrating the implant tab with tab legs normally splayed apart and the implant in its first implanted shape.
Figure 70:
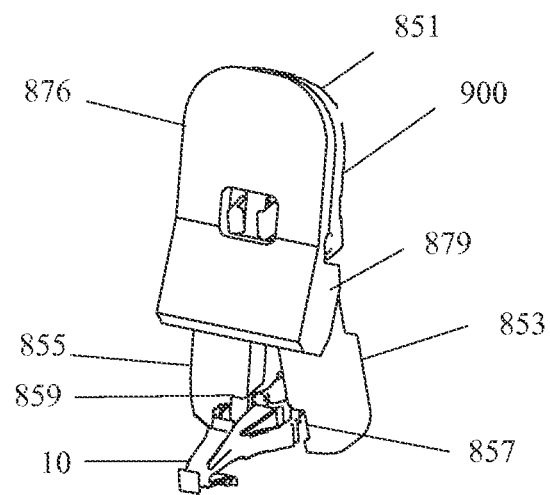
FIG. 70 is a perspective view illustrating the implant engaged by the implant tab.
Figure 71:
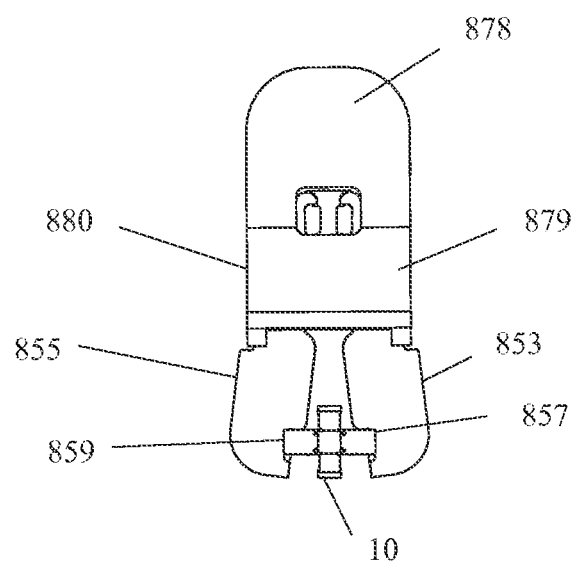
FIG. 71 is a front view illustrating the implant engaged by the implant tab.
Figure 72:
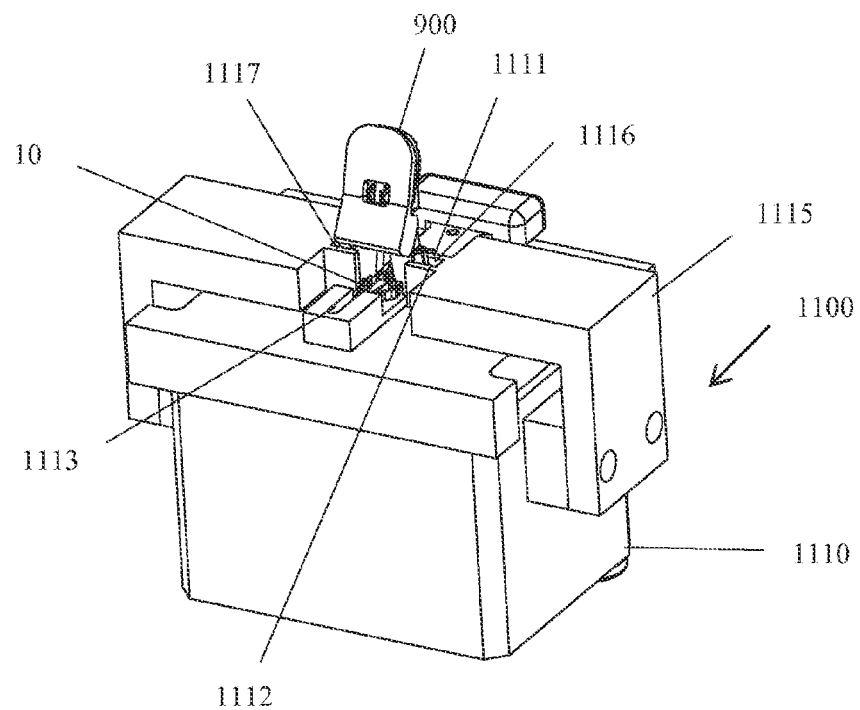
FIG. 72 is a perspective view illustrating the implant tab and the implant inserted within a loading surface of the implant tab press tool.
Figure 73:
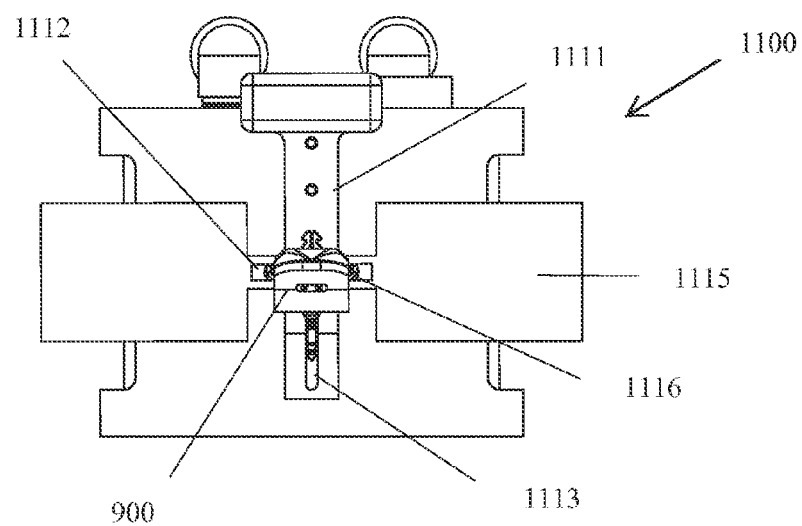
FIG. 73 is a top view illustrating the implant tab and the implant inserted within a loading surface of the implant tab press tool.
Figure 74:
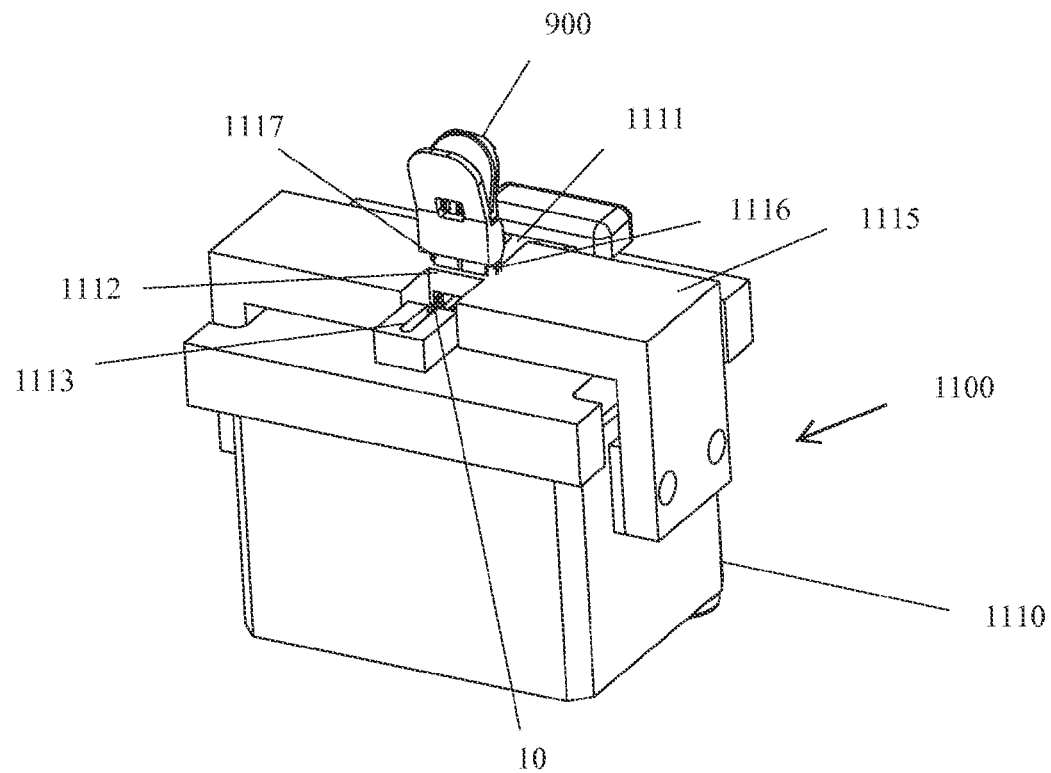
FIG. 74 is a perspective view illustrating a vice of the implant press tool engaging the implant tab.
Figure 75:
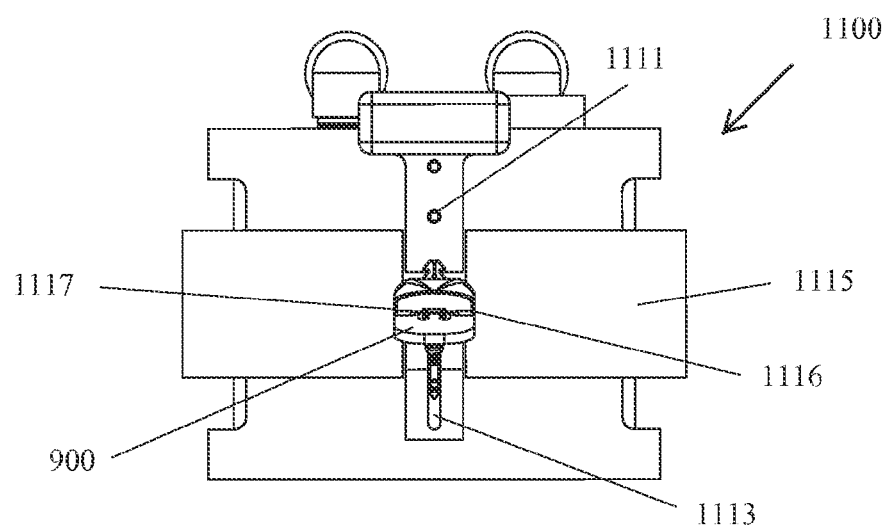
FIG. 75 is a top view illustrating the vice of the implant press tool engaging the implant tab.
Figure 76:
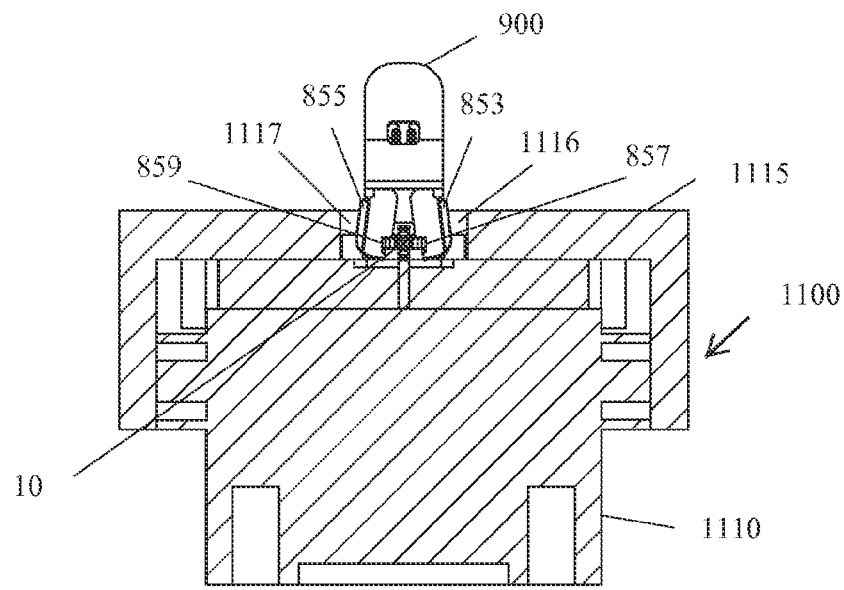
FIGS. 76 and 77 are cross sectional front views illustrating the vice of the implant press tool engaging the implant tab.
Figure 77:
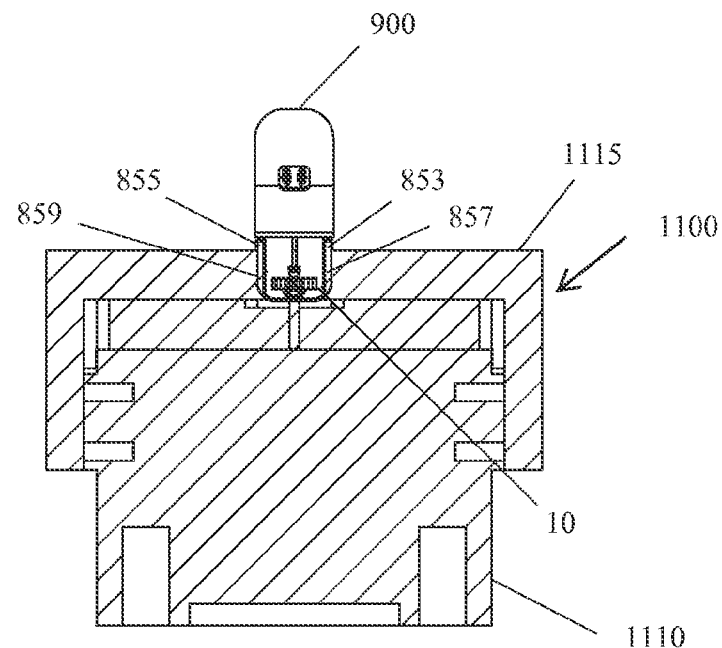

To load the implant tab 900 with the implant 10, the implant tab 900 first receives therein the implant 10 in its first implanted shape. In particular, as illustrated in FIGS. 69-71, the implant tab 900 with its tab legs 853 and 855 in the normally open position, surround a portion of the legs 130 and 131 of the implant 10. Specifically, the tab engagement surfaces 857 and 859 contact a portion of the legs 130 and 131 of the implant 10 to hold the implant 10 engaged with the implant tab 900. After the implant tab 900 engages the implant 10, the implant tab 900 and the implant 10 insert within the loading surface 1111 of the implant tab press tool 1100.

In order to properly insert the implant tab 900 and the implant 10 within the loading surface 1111 of the implant tab press tool 1100, the implant 10 is placed within the implant retention slot 1113 and the implant tab 900 is placed within the tab retention slot 1112. After the implant 10 and the implant tab 900 are placed within the implant retention slot 1113 and tab retention slot 1112, respectively, the vice 1115 is pneumatically activated to load the implant tab 900 with the implant 10. Specifically, the press faces 1116 and 1117 of the vice 1115 contact a respective tab leg 853 and 855 and move the tab legs 853 and 855 of the implant tab 900 to the closed position. Moving the tab legs 853 and 855 to the closed position constrains the legs 130 and 131 of the implant 10 into their insertion shape thereby loading the implant tab 900 with the implant 10. After the tab legs 853 and 855 move to the closed position, a press tool operator moves the implant tab 900 to its locked position. In particular, the implant tab front 875 is moved to its engaged position such that the tab constraining flaps 879 and 880 grasp the tab legs 853 and 855. The grasping of the tab legs 853 and 855 by the tab constraining flaps 879 and 880 holds the tab legs 853 and 855 in the closed position thereby coupling the implant 10 to the implant tab 900. After coupling the implant tab 900 with the implant 10, the press tool operator deactivates the implant tab press tool 1100 releasing the implant tab 900 with the now coupled implant 10 from the implant tab press tool 1100. The implant tab 900 with the now coupled implant 10 is prepared for engagement with the implant inserter 800.

FIGS. 78-85 illustrate a method of loading the implant inserter 800 with the implant tab 900 and its coupled implant 10 according to the present invention. The method includes an inserter press tool 1500 to load the implant inserter 800 with the implant tab 900 and its coupled implant 10. Each method step of the preferred embodiment at any given time normally involves multiple implant tabs 900 (with coupled implants 10) and multiple implant inserters 800, however, for the sake of disclosure and in order to aid in the understanding of the present invention, the method described herein will included only one implant tab 900, one implant 10, and one implant inserter 800.

Figure 78:
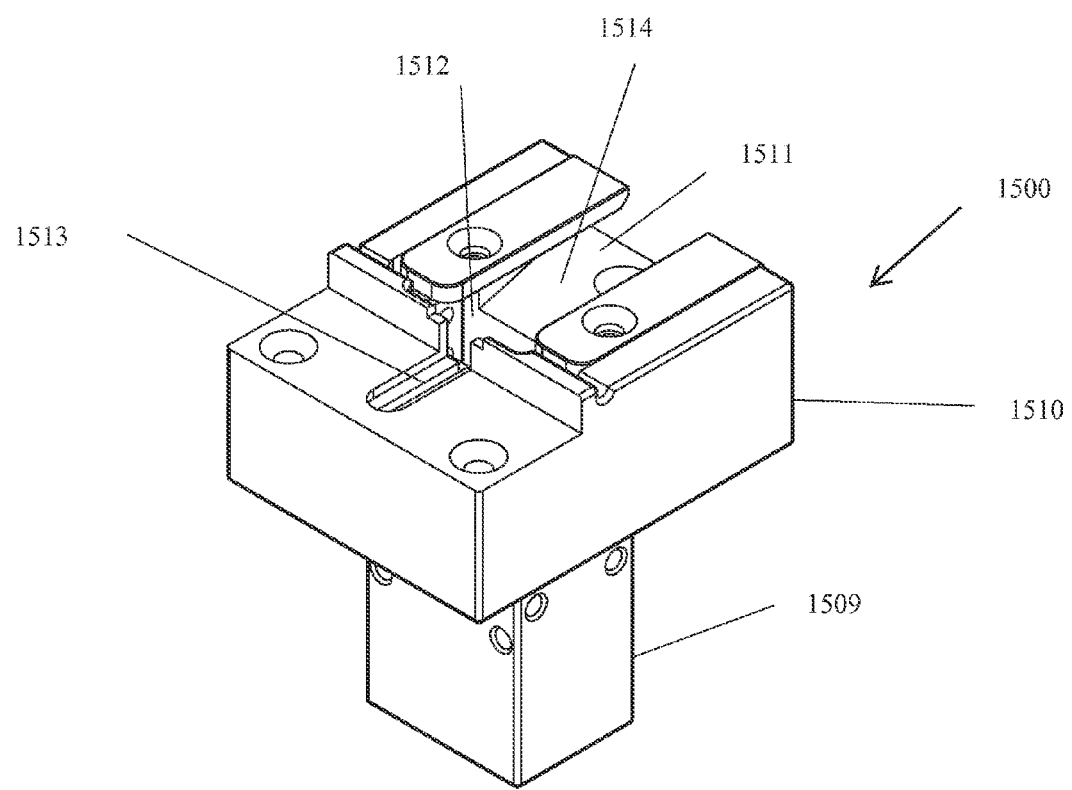
FIG. 78 is a perspective view illustrating an inserter press tool.
Figure 79:
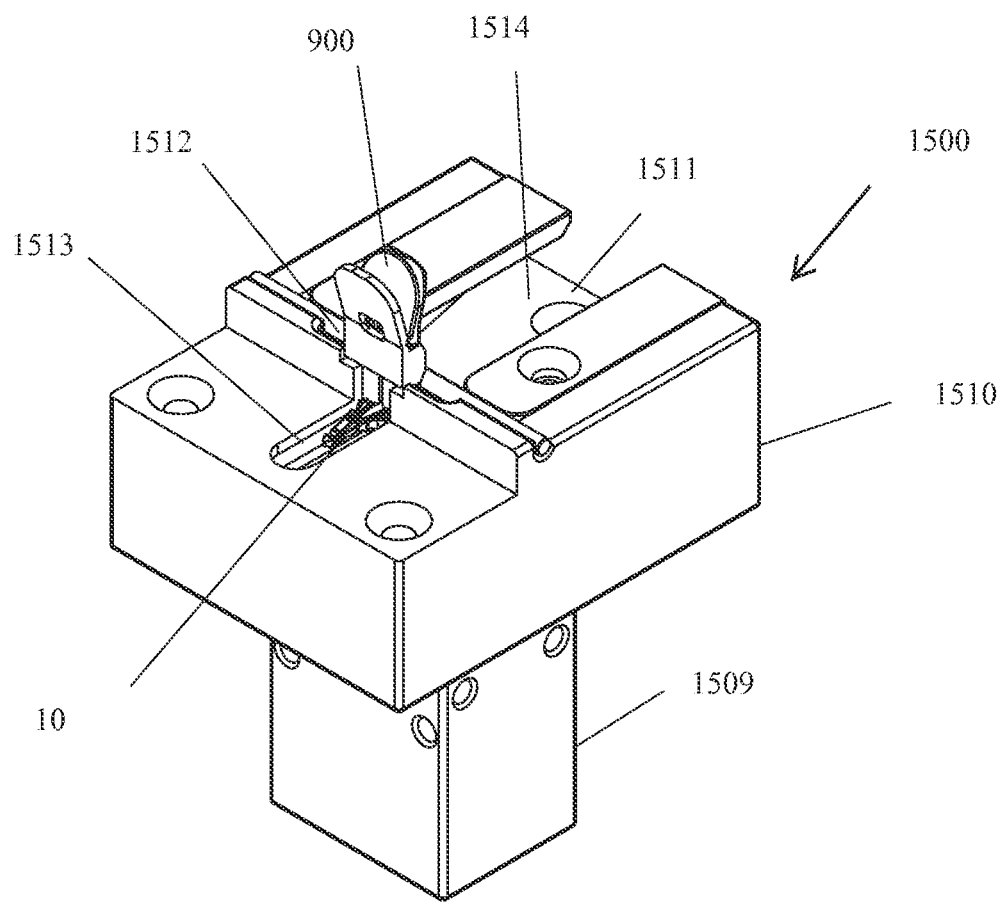
FIG. 79 is a perspective view illustrating the implant tab and the implant inserted within a loading surface of the inserter press tool.
Figure 80:
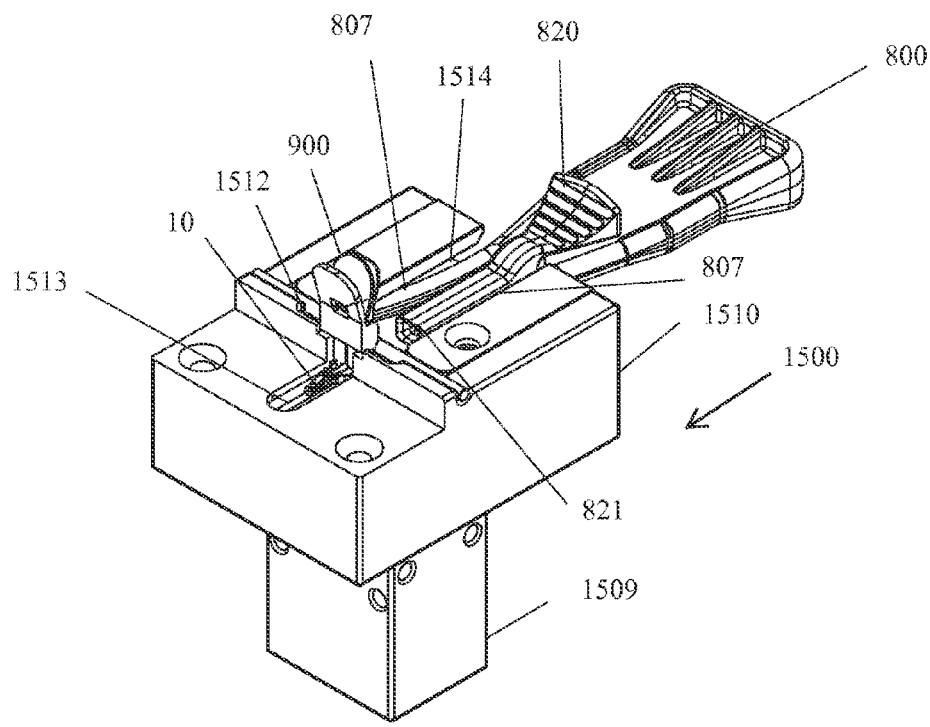
FIG. 80 is a perspective view illustrating an implant inserter inserted within a loading surface of the inserter press tool.
Figure 81:
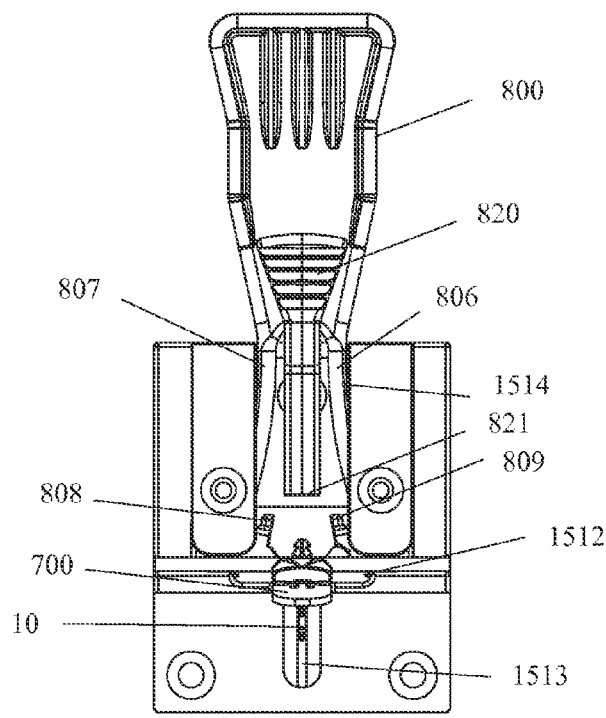
FIG. 81 is a top view illustrating the implant inserter inserted within a loading surface of the inserter press tool.
Figure 82:
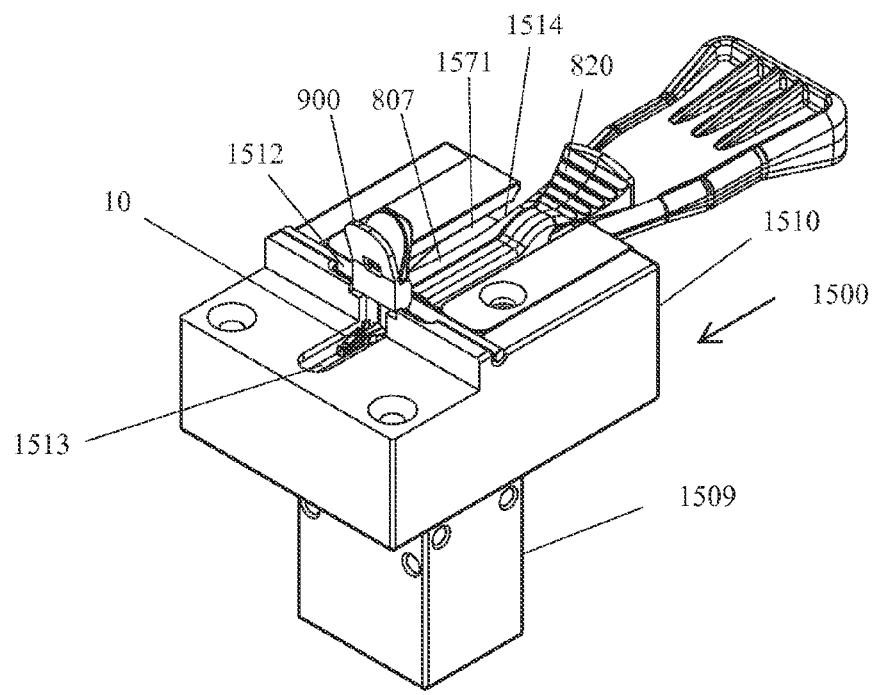
FIG. 82 is a perspective view illustrating a vice of the inserter press tool engaging the implant inserter.
Figure 83:
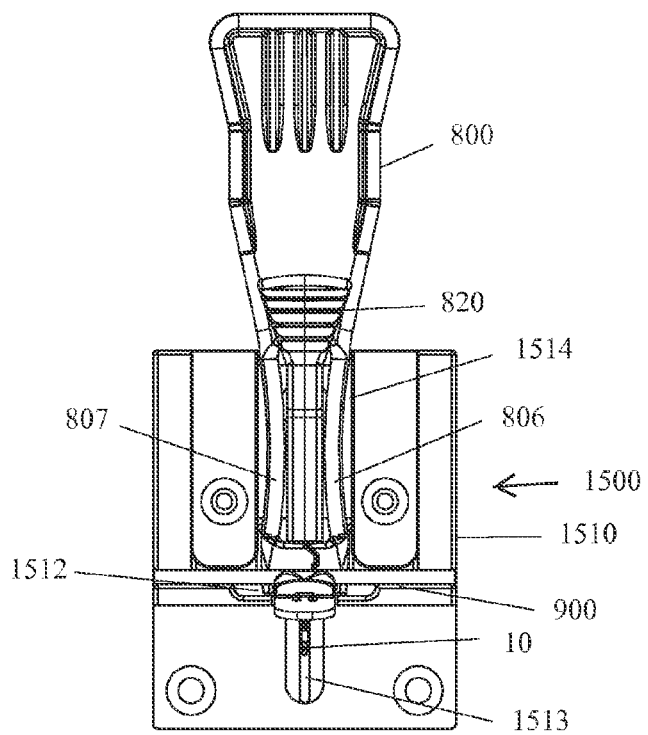
FIG. 83 is a top view illustrating the vice of the inserter press tool engaging the implant inserter.
Figure 84:
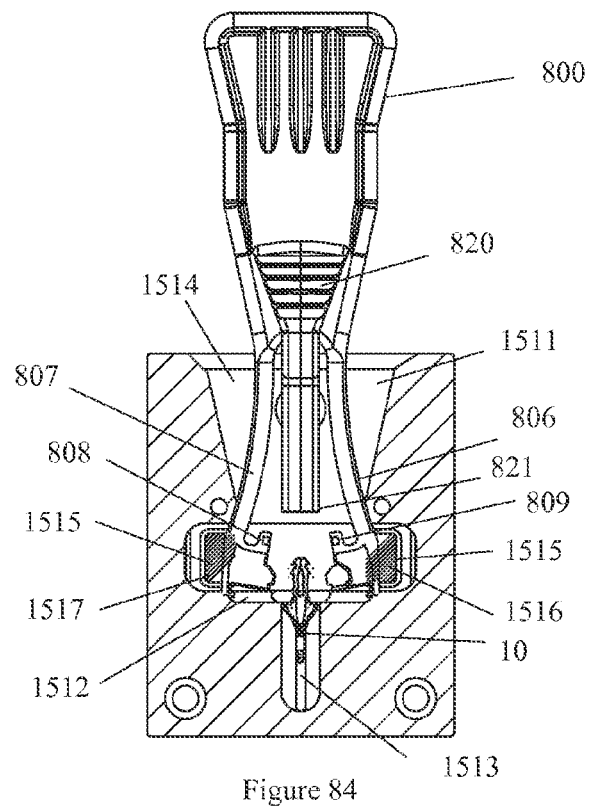
FIGS. 84 and 85 are cross sectional top views illustrating the vice of the inserter press tool engaging the inserter.
Figure 85:
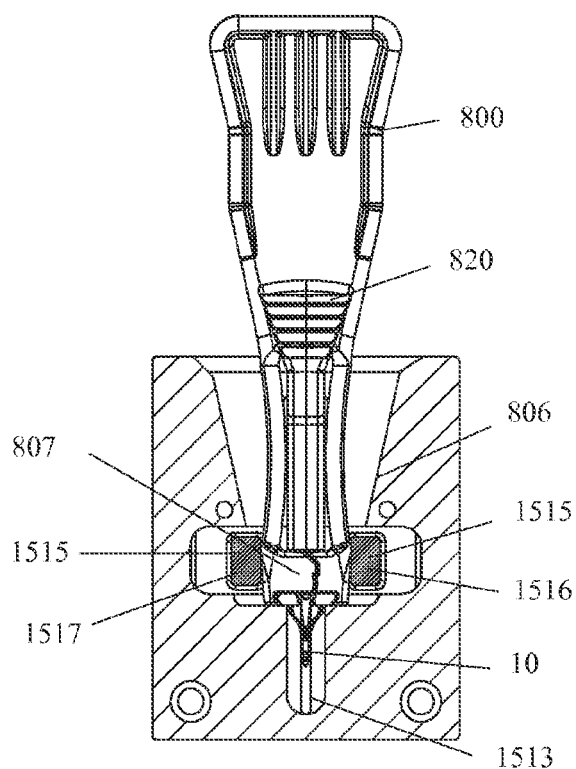

FIGS. 78, 84, and 85 illustrate the inserter press tool 1500 that includes a press tool base 1509, a press tool body 1510, and a vice 1515. The press tool body 1510 defines a loading surface 1511 including an implant tab retention slot 1512, an implant retention slot 1513, and an inserter retention slot 1514. The vice 1515 resides within the inserter retention slot 1514 and defines press faces 1516 and 1517. The inserter press tool 1500 in the present invention is a pneumatic press; however, one of ordinary skill in the art will recognize that any form of inserter press tool may be implemented.

To load the implant inserter 800 with the implant tab 900 and the implant 10, the implant tab 900 with the coupled implant 10 inserts within the loading surface 1511 of the inserter press tool 1500. In particular, the implant tab 900 inserts within the tab retention slot 1512, the first and second body sections 150 and 151 of the implant 10 insert within the implant retention slot 1513. In addition, the legs 130 and 131 extend into the inserter retention slot 1514. After the implant tab 900 and the implant 10 insert within the tab retention slot 1512 and implant retention slot 1513, respectively, the implant inserter 800 in its open position inserts within the inserter retention slot 1514. Specifically, the inserter arms 806 and 807 in their normally splayed position insert within the inserter retention slot 1514. Furthermore, once the implant inserter 800 inserts within the inserter retention slot 1514, a portion of the inserter arms 806 and 807 reside within the tab retention slot 1512.

After the implant inserter 800 inserts within the inserter retention slot 1514, the vice 1515 engages the implant inserter 800 to load the implant inserter 800 with the implant tab 900 and the implant 10. Specifically, the press faces 1516 and 1517 of the vice 1515 contact a respective end of each inserter arm 806 and 807 and move the inserter arms 806 and 807 to their implant engagement position. In the implant engagement position, the inserter arms 806 and 807 grasps a respective tab leg 853 and 855 to maintain the implant tab 900 engaged with the implant inserter 800. Furthermore, the implant engagement surfaces 814 and 815 of the inserter arms 806 and 807 encompass and engage the ends of the legs 130 and 131 of the implant 10 to assist in maintaining the legs 130 in their insertion shape. After the inserter arms 806 and 807 travel to their implant engagement position, the implant inserter 800 is moved to its locked position. In particular, a press tool operator moves the inserter slider 820 forward such that the slider hole 821 maintains contact with the grasping projections 808 and 809. With the slider hole 821 engaged with the grasping projections 808 and 809, the inserter arms 806 and 807 remain constrained in their implant engagement position. After the implant inserter 800 is moved to its locked position, the press tool operator deactivates the inserter press tool 1500 releasing the implant inserter 800 with the loaded implant tab 900 and the implant 10 from the inserter press tool 1500. The implant 10 is now preloaded onto the implant inserter 800 with the implant tab 900 in place, and is ready for packaging or implantation into tissue or bone.

Although the present invention has been described in terms of the foregoing preferred embodiments, such description has been for exemplary purposes only and, as will be apparent to those of ordinary skill in the art, many alternatives, equivalents, and variations of varying degrees will fall within the scope of the present invention. That scope, accordingly, is not to be limited in any respect by the foregoing detailed description; rather, it is defined only by the claims that follow.

The invention claimed is:
1. A method of loading an implant inserter with an implant tab and an intramedullary orthopedic implant, comprising:
    providing an intramedullary orthopedic implant, comprising:

a body section including a first end that provides a point of insertion for the body section and a second end, and first and second legs extending from the second end of the body section, wherein the first and second legs begin in a first implanted shape and are movable to a second insertion shape;

providing an implant tab movable between an unlocked and a locked position;

providing an implant inserter movable between an open and a locked position;

engaging the first and second legs of the intramedullary orthopedic implant in their first implanted shape with the implant tab when the implant tab resides in its unlocked position;

placing the intramedullary orthopedic implant engaged with the implant tab in an implant tab press tool;

activating the implant tab press tool to close the implant tab such that the first and second legs of the intramedullary orthopedic implant move to their second insertion shape;

moving the implant tab to its locked position, wherein the intramedullary orthopedic implant is coupled with the implant tab such that the first and second legs of the intramedullary orthopedic implant are constrained in their second insertion shape;

deactivating the implant tab press tool and removing the implant tab loaded with the intramedullary orthopedic implant from the implant tab press tool;

placing the implant tab coupled with the intramedullary orthopedic implant in an inserter press tool;

placing the implant inserter in its open position in the inserter press tool;

activating the inserter press tool to close the implant inserter such that the implant inserter grasps the implant tab;

moving the implant inserter to its locked position, wherein the implant inserter is loaded with the implant tab and the intramedullary orthopedic implant coupled therewith; and deactivating the inserter press tool and removing the implant inserter loaded with the implant tab and the intramedullary orthopedic implant coupled therewith from the inserter press tool.

2. The method of loading an implant inserter with an implant tab and an intramedullary orthopedic implant according to claim 1, wherein the implant tab comprises:

first and second tab legs having a normally open position and a closed position, wherein the first and second tab legs in their normally open position are adapted to engage the first and second legs of the intramedullary orthopedic implant in their implanted shape, further wherein the first and second tab legs in their closed position are adapted to constrain the first and second leg of the intramedullary orthopedic implant in their insertion shape; and an implant tab lock comprising first and second tab constraining flaps, the implant tab lock being movable from a disengaged position to an engaged position whereby the first tab constraining flap grasps the first tab leg and the second tab constraining flap grasps the second tab leg.

3. The method of loading an implant inserter with an implant tab and an intramedullary orthopedic implant according to claim 2, wherein the implant inserter, comprises:

first and second inserter arms having a normally splayed position and an implant engagement position, the first and second inserter arms each including a grasping projection;

an inserter slider having a slider hole, wherein, when the first and second inserter arms reside in their implant engagement position, the slider is movable such that its slider hole engages the grasping projections to lock the inserter arms in their implant engagement position.

4. The method of loading an implant inserter with an implant tab and an intramedullary orthopedic implant according to claim 3, wherein the implant tab press tool, comprises:

a loading surface, comprising;
a tab retention slot adapted to receive the implant tab, and
an implant retention slot adapted to receive the intramedullary orthopedic implant; and a vice, comprising;
a first press face adapted to engage the first tab leg of the implant tab, and
a second press face adapted to engage the second tab leg of the implant tab.

5. The method of loading an implant inserter with an implant tab and an intramedullary orthopedic implant according to claim 4, comprising inserting the implant tab and the intramedullary orthopedic implant within the loading surface of the implant tab press tool.

6. The method of loading an implant inserter with an implant tab and an intramedullary orthopedic implant according to claim 5, wherein the vice of the implant tab press tool is pneumatically activated to couple the implant tab with the intramedullary orthopedic implant.

7. The method of loading an implant inserter with an implant tab and an intramedullary orthopedic implant according to claim 5, wherein the first press face of the vice contacts the first tab leg and the second press face of the vice contacts the second tab leg, further wherein activation of the vice moves the first and second tab legs of the intramedullary orthopedic implant such that the first and second tab legs constrain the first and second legs of the intramedullary orthopedic implant.

8. The method of loading an implant inserter with an implant tab and an intramedullary orthopedic implant according to claim 7, wherein constraining the first and second legs moves the intramedullary orthopedic implant to the second insertion shape.

9. The method of loading an implant inserter with an implant tab and an intramedullary orthopedic implant according to claim 7, wherein, after activation of the vice, the implant tab lock is moved from its disengaged position to its engaged position such that the first and second tab constraining flaps grasp and hold a respective first and second tab leg thereby coupling the intramedullary orthopedic implant with the implant tab.

10. The method of loading an implant inserter with an implant tab and an intramedullary orthopedic implant according to claim 9, wherein deactivation of the implant tab press tool releases the implant tab and the intramedullary orthopedic implant from the implant tab press tool.

11. The method of loading an implant inserter with an implant tab and an intramedullary orthopedic implant according to claim 4, comprising inserting the implant tab within the tab retention slot of the implant tab press tool and the intramedullary orthopedic implant within the implant retention slot of the implant tab press tool.

12. The method of loading an implant inserter with an implant tab and an intramedullary orthopedic implant according to claim 3, wherein the inserter press tool comprises:
- a loading surface, comprising;
  - a tab retention slot adapted to receive the implant tab and a portion of the implant inserter,
  - an implant retention slot adapted to receive the intramedullary orthopedic implant, and
  - an inserter retention slot adapted to receive the implant inserter; and
- a vice, comprising:
  - a first press face adapted to engage the first inserter arm of the implant inserter, and
  - a second press face adapted to engage the second inserter arm of the implant inserter.

13. The method of loading an implant inserter with an implant tab and an intramedullary orthopedic implant according to claim 12, comprising inserting the implant tab within the tab retention slot of the inserter press tool and the intramedullary orthopedic implant within the implant retention slot of the inserter press tool.

14. The method of loading an implant inserter with an implant tab and an intramedullary orthopedic implant according to claim 13, wherein the first and second legs of the intramedullary implant extend into the inserter retention slot.

15. The method of loading an implant inserter with an implant tab and an intramedullary orthopedic implant according to claim 14, wherein, after the implant tab with the coupled intramedullary orthopedic implant inserts within the loading surface of the inserter press tool, the implant inserter inserts within the inserter retention slot of the inserter press tool.

16. The method of loading an implant inserter with an implant tab and an intramedullary orthopedic implant according to claim 15, wherein the implant inserter inserts within the inserter retention slot of the inserter press tool such that the first and second inserter arms in their normally splayed position reside within the tab retention slot.

17. The method of loading an implant inserter with an implant tab and an intramedullary orthopedic implant according to claim 16, wherein the vice of the inserter press tool is pneumatically activated to load the implant inserter with the implant tab and the intramedullary orthopedic implant.

18. The method of loading an implant inserter with an implant tab and an intramedullary orthopedic implant according to claim 16, wherein the first and second press faces of the vice contact a respective first and second inserter arm to move the inserter arms from their normally splayed position to their implant engagement position such that the inserter arms grasp a respective tab leg of the implant tab to maintain the implant tab engaged with the implant inserter.

19. The method of loading an implant inserter with an implant tab and an intramedullary orthopedic implant according to claim 18, wherein moving the inserter arms to their implant engagement position causes a portion of the inserter arms to encompass and engage the ends of the first and second leg of the intramedullary orthopedic implant thereby assisting the implant tab in maintaining the first and second legs of the intramedullary orthopedic implant in their insertion shape.

20. The method of loading an implant inserter with an implant tab and an intramedullary orthopedic implant according to claim 18, wherein, after the inserter arms move to their implant engagement position, the inserter slider is moved such that the slider hole engages and maintains contact with the grasping projections thereby locking the inserter arms in their implant engagement position and loading the implant tab and the intramedullary orthopedic implant with the implant inserter.

21. The method of loading an implant inserter with an implant tab and an intramedullary orthopedic implant according to claim 20, wherein the inserter press tool is deactivated to release the implant inserter with the loaded implant tab and the intramedullary orthopedic implant.

\* \* \* \* \*

UNITED STATES PATENT AND TRADEMARK OFFICE
CERTIFICATE OF CORRECTION

PATENT NO. : 9,636,155 B2  
APPLICATION NO. : 14/804826  
DATED : May 2, 2017  
INVENTOR(S) : Joseph H. Taber et al.

Page 1 of 1

It is certified that error appears in the above-identified patent and that said Letters Patent is hereby corrected as shown below:

In Item (72) Inventors, the inventor name "Peterson" should be changed to --Petersen--.

Signed and Sealed this  
Twenty-sixth Day of September, 2017

Joseph Matal  
*Performing the Functions and Duties of the*  
*Under Secretary of Commerce for Intellectual Property and*  
*Director of the United States Patent and Trademark Office*